(12) United States Patent
Dervan et al.

(10) Patent No.: US 8,835,480 B2
(45) Date of Patent: Sep. 16, 2014

(54) INHIBITORS FOR STEROID RESPONSE ELEMENTS AND RELATED METHODS

(75) Inventors: Peter B. Dervan, San Marino, CA (US); Nicholas G. Nickols, Van Nuys, CA (US)

(73) Assignee: California Institute of Technology, Pasadena, CA (US)

( * ) Notice: Subject to any disclaimer, the term of this patent is extended or adjusted under 35 U.S.C. 154(b) by 710 days.

(21) Appl. No.: 12/148,943

(22) Filed: Apr. 22, 2008

(65) Prior Publication Data

US 2009/0042965 A1 Feb. 12, 2009

Related U.S. Application Data

(60) Provisional application No. 60/926,080, filed on Apr. 23, 7.

(51) Int. Cl.
| | | |
|---|---|---|
| *A61K 31/4164* | (2006.01) | |
| *C07D 233/54* | (2006.01) | |
| *A61K 31/40* | (2006.01) | |
| *C07D 207/50* | (2006.01) | |
| *A61K 31/785* | (2006.01) | |
| *C07D 403/14* | (2006.01) | |
| *C07D 233/88* | (2006.01) | |
| *A61K 31/4025* | (2006.01) | |

(52) U.S. Cl.
CPC .......... *A61K 31/785* (2013.01); *C07D 233/54* (2013.01); *A61K 31/40* (2013.01); *C07D 207/50* (2013.01); *A61K 31/4164* (2013.01); *C07D 403/14* (2013.01); *C07D 233/88* (2013.01); *A61K 31/4025* (2013.01)
USPC ........... 514/400; 514/423; 514/426; 514/427; 548/311.1; 548/314.7; 548/326.5; 548/335.1; 548/557; 548/560

(58) Field of Classification Search
None
See application file for complete search history.

(56) References Cited

U.S. PATENT DOCUMENTS

| 5,998,140 | A | 12/1999 | Dervan |
|---|---|---|---|
| 6,090,947 | A | 7/2000 | Dervan |
| 6,143,901 | A | 11/2000 | Dervan |
| 6,303,312 | B1 | 10/2001 | Dervan |
| 6,472,537 | B1 | 10/2002 | Baird |
| 6,506,906 | B1 | 1/2003 | Dervan |
| 6,545,162 | B1 | 4/2003 | Dervan |
| 6,555,692 | B1 | 4/2003 | Dervan |
| 6,559,125 | B1 | 5/2003 | Dervan |
| 6,635,417 | B1 | 10/2003 | Dervan |
| 6,660,255 | B1 | 12/2003 | Gottesfeld |
| 6,673,940 | B1 | 1/2004 | Dervan |
| 6,958,240 | B1 | 10/2005 | Baird |
| 7,049,061 | B1 | 5/2006 | Baird |
| 7,087,378 | B1 | 8/2006 | Baird |
| 7,452,730 | B2 | 11/2008 | Dervan |
| 7,589,171 | B2 * | 9/2009 | Bashkin et al. ............... 530/323 |
| 2003/0109448 | A1 | 6/2003 | Crowley |
| 2005/0026174 | A1 | 2/2005 | Dervan |
| 2006/0014163 | A1 | 1/2006 | Dervan |
| 2006/0019972 | A1 | 1/2006 | Dervan |
| 2006/0025429 | A1 | 2/2006 | Dervan |
| 2006/0270727 | A1 | 11/2006 | Melander |

FOREIGN PATENT DOCUMENTS

| WO | WO 97/30975 | 8/1997 |
|---|---|---|
| WO | WO 98/35702 | 8/1998 |
| WO | WO 98/37066 | 8/1998 |
| WO | WO 98/37087 | 8/1998 |
| WO | WO 98/45284 | 10/1998 |
| WO | WO 98/49142 | 11/1998 |
| WO | WO 98/50058 | 11/1998 |
| WO | WO 03/041128 | 5/2003 |

OTHER PUBLICATIONS

Osteoporosis from http://www.nof.org/osteoporosis/index.htm, p. 1. Accessed Jul. 6, 2009.*
Minoxidil from http://www.mayoclinic.com/health/hair-loss/DS00278/DSECTION=treatments%2Dand%2Ddrugs, pp. 1-4. Accessed Jul. 6, 2009.*
Mrksich, Milan and Dervan, Peter B.; "Recognition in the minor groove of DNA at 5'-(a,t)gcgc(a,t)-3 by a four ring tripeptide dimer. Reversal of the specificity of the natural product distamycin." J. Am. Chem. Soc. (1995) 117 p. 3325-3332.*
Almarsson et al., 1993, "Molecular mechanics calculations of the structures of polyamide nucleic acid DNA duplexes and triple helical hybrids," Proc. Natl. Acad. Sci. USA 90:7518-7522.
Baird et al., 1996, "Solid Phase Synthesis of Polyamides Containing Imidazole and Pyrrole Amino Acids," J. Am. Chem. Soc. 118:6141-6146.
Best et al., 2003, "Nuclear localization of pyrrole-imidazole polyamide-fluorescein conjugates in cell culture," Proc. Natl. Acad. Sci. USA 100(21):12063-12068.
Burnett et al., 2006, "DNA sequence-specific polyamides alleviate transcription inhibition associated with long GAA•TTC repeats in Friedrich's ataxia," Proc. Natl. Acad. Sci. USA 103(31):11497-11502.
Chen et al., 2004, "Molecular determinants of resistance to antiandrogen therapy," Nature Medicine 10(1):33-39.
Cheng et al., 2006, "Short Hairpin RNA Knockdown of the Androgen Receptor Attenuates Ligand-Independent Activation and Delays Tumor Progressions," Cancer Res. 66(21):10613-10620.
Cherny et al., 1993, "DNA unwinding upon strand-displacement binding of a thymine-substituted polyamide to double-stranded DNA," Proc. Natl. Acad. Sci. USA 90:1667-1670.
Chiang et al., 2000, "Targeting the Ets Binding Site of the HER2/neu Promoter with Pyrrole-Imidazole Polyamides," J. Biol. Chem. 275(32):24246-24254.

(Continued)

*Primary Examiner* — James H Alstrum Acevedo
*Assistant Examiner* — Fred Reynolds
(74) *Attorney, Agent, or Firm* — Stahl Law Firm

(57) ABSTRACT

The present invention relates to polyamides capable of inhibiting ARE-, GRE- and ERE-mediated gene regulation in cells. The invention also relates to methods to treat diseases related to ARE-, GRE- and ERE-mediated gene regulation.

8 Claims, 35 Drawing Sheets

(56) References Cited

OTHER PUBLICATIONS

Coull et al., 2002, "Targeted Derepression of the Human Immunodeficiency Virus Type 1 Long Terminal Repeat by Pyrrole-Imidazole Polyamides," J. Virology 76(23):12349-12354.
DePrimo et al., 2002, "Transcriptional programs activated by exposure of human prostate cancer cells to androgen," Genome Biology 3(7):research0032.1-0032.12.
Dervan, 2001, "Molecular Recognition of DNA by Small Molecules," Bioorganic & Medicinal Chem. 9:2215-2235.
Dickinson et al., 1998, "Inhibition of RNA polymerase II transcription in human cells by synthetic DNA-binding ligands," Proc. Natl. Acad. Sci. USA 95:12890-12895.
Dickinson et al., 2004, "Arresting Cancer Proliferation by Small-Molecule Gene Regulation," Chemistry & Biology 11: 1583-1594.
Dudouet et al., 2003, "Accessibility of Nuclear Chromatin by DNA Binding Polyamides," Chemistry & Biology 10:859-867.
Edelson et al., 2004, "Influence of structural variation on nuclear localization of DNA-binding polyamde-fluorophore conjugates," Nucleic Acids Res. 32(9):2802-2818.
Ehley et al., 2002, "Promoter Scanning for Transcription Inhibition with DNA-Binding Polyamides," Molecular and Cellular Biology 22(6):1723-1733.
Gottesfeld et al., 2001, "Sequence-specific Recognition of DNA in the Nucleosome by Pyrrole-Imidazole Polyamides," J. Mol. Biol. 309:615-629.
Gupta et al., 2002, "Molecular mechanisms of glucocorticoid action," Current Science 83(9):1103-1111.
Gygi et al., 2002, "Use of fluorescent sequence-specific polyamides to discriminate human chromosomes by microscopy and flow cytometry," Nucleic Acids Res. 30(13):2790-2799.
Holzbeierlein et al., "Gene Expression Analysis of Human Prostate Carcinoma during Hormonal Therapy Identifies Androgen-Responsive Genes and Mechanisms of Therapy Resistance," Am. J. of Pathology 164(1):217-227, 2004.
Hsu et al., 2007, "Completion of a Programmable DNA-Binding Small Molecule Library," Tetrahedron 63(27):6146-6151.
Hurley, 2002, "DNA and its associated processes as targets for cancer therapy," Nature Reviews 2:188-200.
Isaacs et al., 2004, "Androgen receptor outwits prostate cancer drugs," Nature Medicine 10(1):26-27.
Kelly et al., 1996, "Binding site size limit of the 2:1 pyrrole-imidazole polyamide-DNA motif," Proc. Natl. Acad. Sci. USA 93:6981-6985.
Klein et al., 1997, "Progression of metastatic human prostate cancer to androgen independence in immunodeficient SCID mice," Nature Medicine 3(4):402-408.
Lacy et al., 2002, "Recognition of T•G mismatched base pairs in DNA by stacked imidazole-containing polyamides: surface plasmon resonance and circular dichroism studies," Nucleic Acids Res. 30(8):1834-1841.
Lacy et al., 2004, "Energetic basis for selective recognition of T•G mismatched base pairs in DNA by imidazole-rich polyamides," Nucleic Acids Res. 32(6):2000-2007.
Marques et al., 2002, "Toward an Understanding of the Chemical Etiology for DNA Minor-Groove Recognition by Polyamides," Helvetica Chimica Acta 85:4485-4517.
Massie et al., 2007, "New androgen receptor genomic targets show an interaction with the ETS1 transcription factor," EMBO reports 8(9):871-878.
McGinley et al., 2007, "Circumventing Anti-Androgen Resistance by Molecular Design," J. Am. Chem. Soc.
Melander et al., 2004, "Regulation of gene expression with pyrrole-imidazole polyamides," J. Biotechnology 112:195-220.
Neamati et al., 1998, "Highly Potent Synthetic Polyamides, Bisdistamycins, and Lexitropsins as Inhibitors of Human Immunodeficiency Virus Type 1 Integrase," Molecular Pharmacology 54:280-290.

Nelson et al., 2003, "Prostate Cancer," N. Eng. J. Med. 349(4):366-381.
Nickols et al., 2006, "Improved nuclear localization of DNA-binding polyamides," Nucleic Acids Res. 35(2):363-370.
Nickols et al., 2007, "Modulating Hypoxia-Inducible Transcription by Disrupting the HF-1-DNA Interface," ACS Chemical Biology 2(8):561-571.
Nickols et al., 2007, "Suppression of androgen receptor-mediated gene expression by a sequence-specific DNA-binding polyamide," Proc. Natl. Acad. Sci. USA 104(25):10418-10423.
Norgaard et al., 1991, "Glucocorticoid receptors in human malignancies: A review," Annals of Oncology 2:541-557.
O'Hare et al., "DNA sequence recognition in the minor groove by crosslinked polyamides: The effect of N-terminal head group and linker length on binding affinity and specificity," Proc. Natl. Acad. Sci. USA 99(1):72-77, 2002.
Olenyuk et al., 2004, "Inhibition of vascular endothelial growth factor with a sequence-specific hypoxia response element antagonist," Proc. Natl. Acad. Sci. USA 101(48):16768-16773.
Philips et al., 2005, "DNA Damage Effects of a Polyamide-CBI Conjugate in SV40 Virions," Mol. Pharmacol. 67:877-882.
Pilch et al., 1996, "Binding of a hairpin polyamide in the minor groove of DNA: Sequence-specific enthalpic discrimination," Proc. Natl. Acad. Sci. USA 93:8306-8311.
Rosen et al., 2005, "The Search for Safer Glucocorticoid Receptor Ligands," Endocrine Reviews 26(3):452-464.
Sazani et al., 2001, "Nuclear antisense effects of neutral, anionic and cationic oligonucleotide analogs," Nucleic Acids Res. 29(19):3965-3974.
Schaal et al., 2003, "Inhibition of human papilloma virus E2 DNA binding protein by covalently linked polyamides," Nucleic Acids Res. 31(4):1282-1291.
Scher et al., 2005, "Biology of Progressive, Castration-Resistant Prostate Cancer: Directed Therapies Targeting the Androgen-Receptor Signaling Axis," J. Clin. Oncol. 23(32):8253-8261.
Sharifi et al., 2006, "Androgen Receptor as a Therapeutic Target for Androgen Independent Prostate Cancer," Am. J. Therapeutics 13:166-170.
Tomlins et al., 2005, "Recurrent Fusion of *TMPRSS2* and ETS Transcription Factor Genes in Prostate Cancer," Science 310:644-648.
Tomlins et al., 2006, "*TMPRSS2:ETV4* Gene Fusions Define a Third Molecular Subtype of Prostate Cancer," Cancer Res. 66(7):3396-3400.
Trauger et al., 1996, "Extension of Sequence-Specific Recognition in the Minor Groove of DNA by Pyrrole-Imidazole Polyamides to 9-13 Base Pairs," J. Am. Chem. Soc. 118:6160-6166.
Tsai et al., 2006, "Unanticipated differences between α- and γ-diaminobutyric acid-linked hairpin polyamide-alkylator conjugates," Nucleic Acids Res. 35(1):307-316.
Urbach et al., 2001, "Toward rules for 1:1 polyamide:DNA recognition," Proc. Natl. Acad. Sci. USA 98(8):4343-4348.
Urbach et al., 2002, "Structure of a β-Alanine-linked Polyamide Bound to a Full Helical Turn of Purine Tract DNA in the 1:1 Motif," J. Mol. Biol. 320:55-71.
Wang et al., 2003, "DNA crosslinking and biological activity of a hairpin polyamide-chlorambucil conjugate," Nucleic Acids Res. 31(4):1208-1215.
Warren et al., 2006, "Defining the sequence-recognition profile of DNA-binding molecules," Proc. Natl. Acad. Sci. USA 103(4):867-872.
White et al., 1996, "Effects of the A•T/T•A Degeneracy of Pyrrole-Imidazole Polyamide Recognition in the Minor Groove of DNA," Biochemistry 35:12532-12537.
Wurtz et al., 2002, "Inhibition of DNA Binding by NF-κB with Pyrrole-Imidazole Polyamides," Biochemistry 41:7604-7609.

* cited by examiner

7: 
8: 
9: 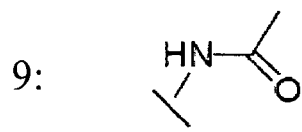
10: 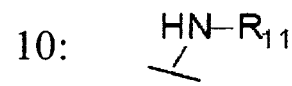
11: 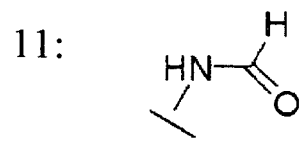
12: 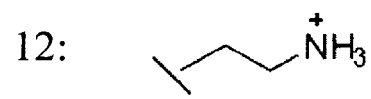
13: 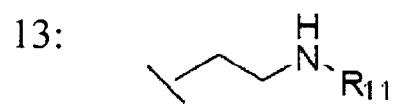
14: 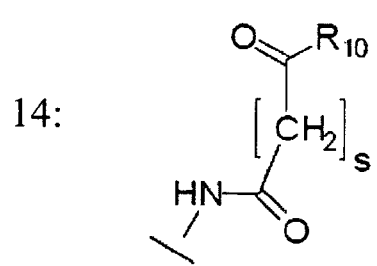
15: 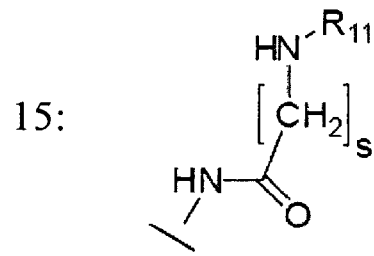
16: 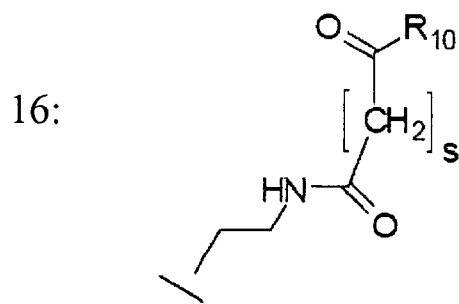
17: 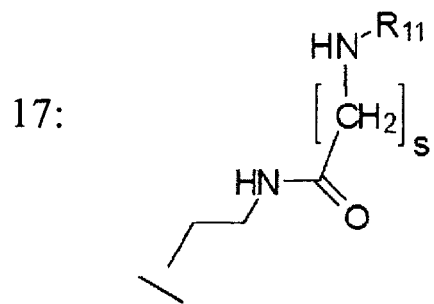
FIGURE 2B

18: 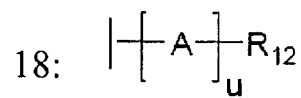   19: 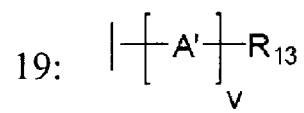
20: 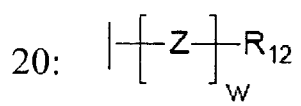
21: 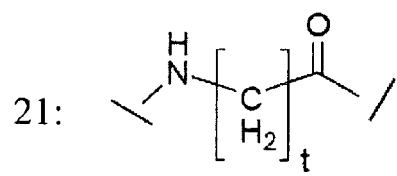   22: 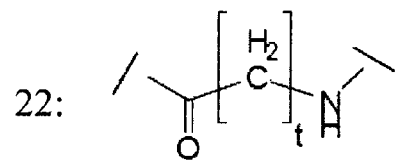
23: 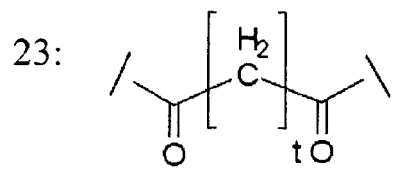
24: 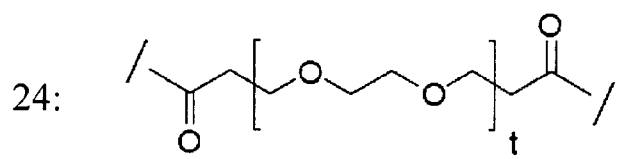
FIGURE 2C 25:  26: 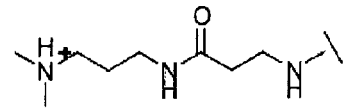
27: 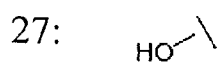 28: 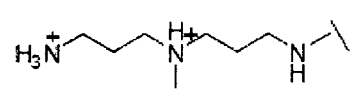
29:  30: 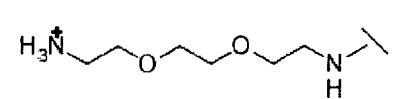
31: 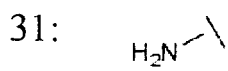 32: 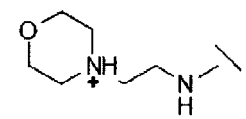
33:  34: 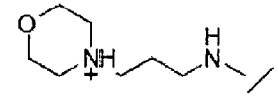
35: 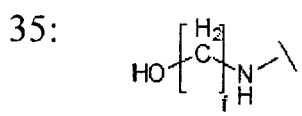 36: 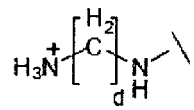
37: 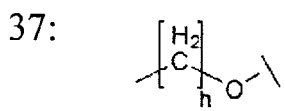 38: 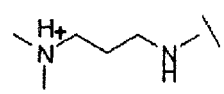
39: 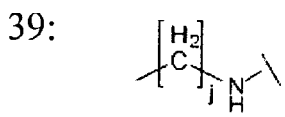
FIGURE 3A

45: 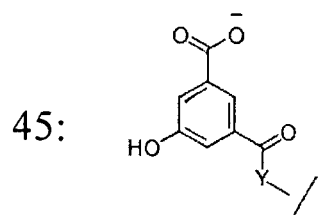   46: 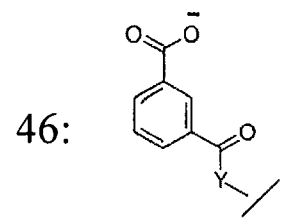
47: 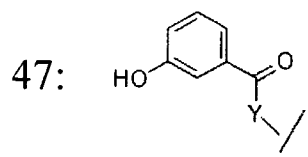   48: 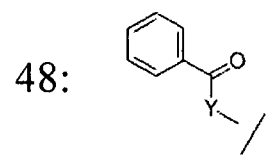
49: 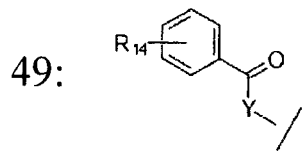   50: 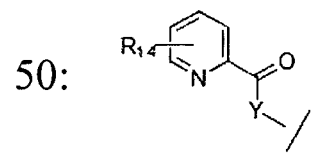
51: 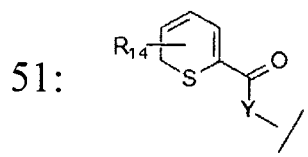   52: 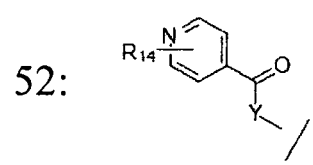
53: 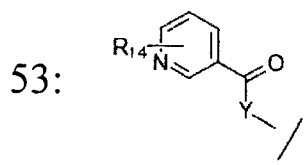   54: 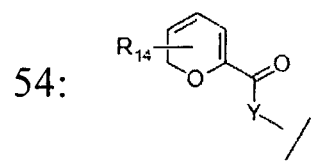
55: 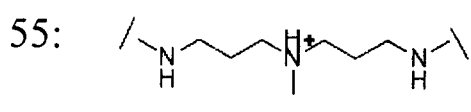   56: 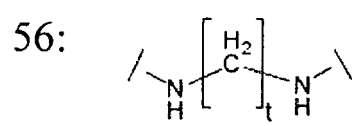
57: 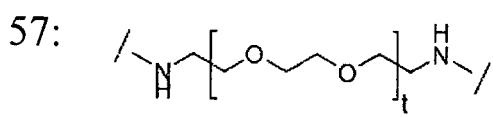
FIGURE 3C

58: 
59: 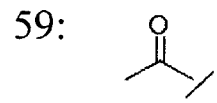
60: 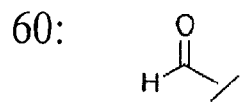
61: 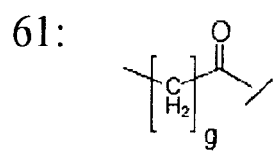
62: 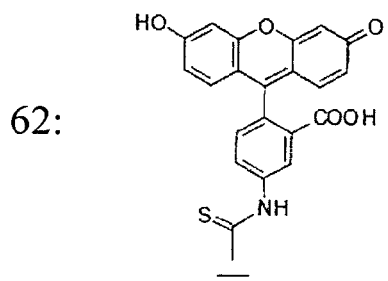
63: 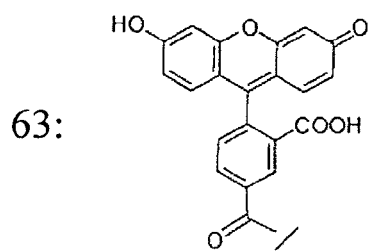
64: 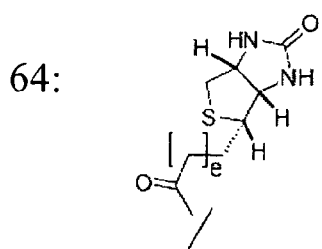
65: 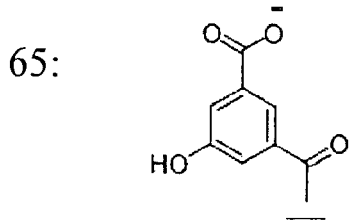
66: 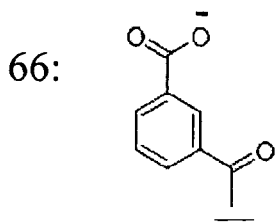
67: 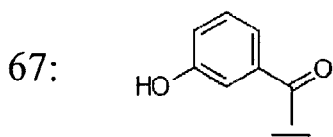
68: 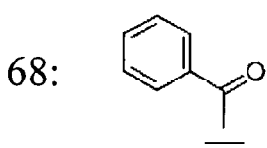
FIGURE 3D

69: 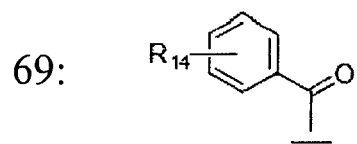 70: 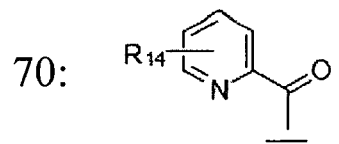
71: 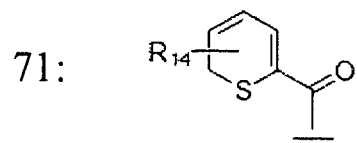 72: 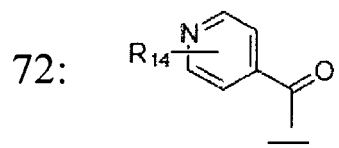
73: 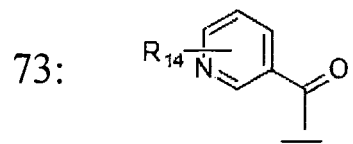 74: 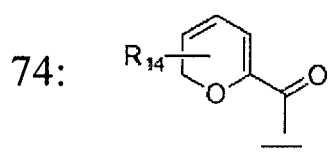
75: 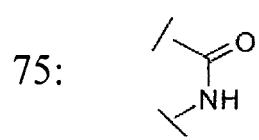 76: 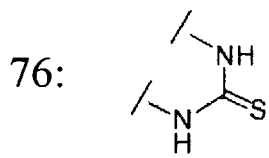
FIGURE 3E A:
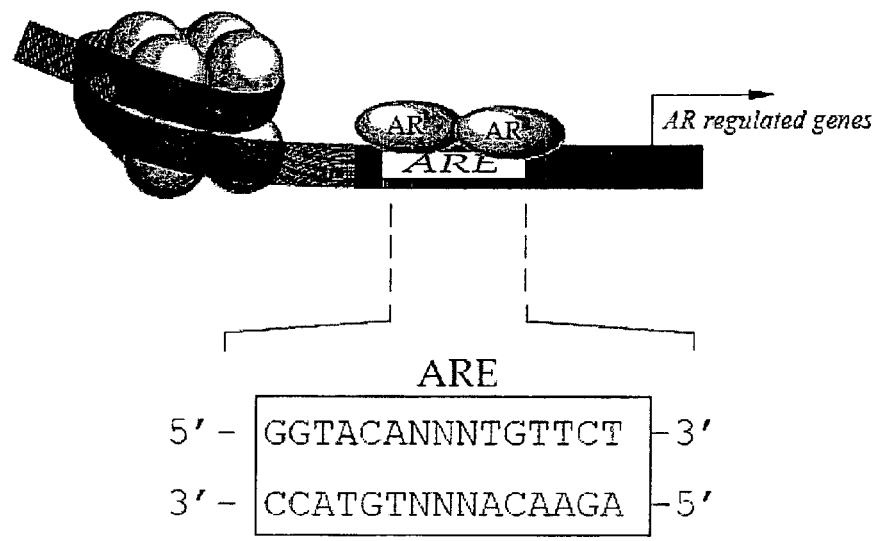
B:
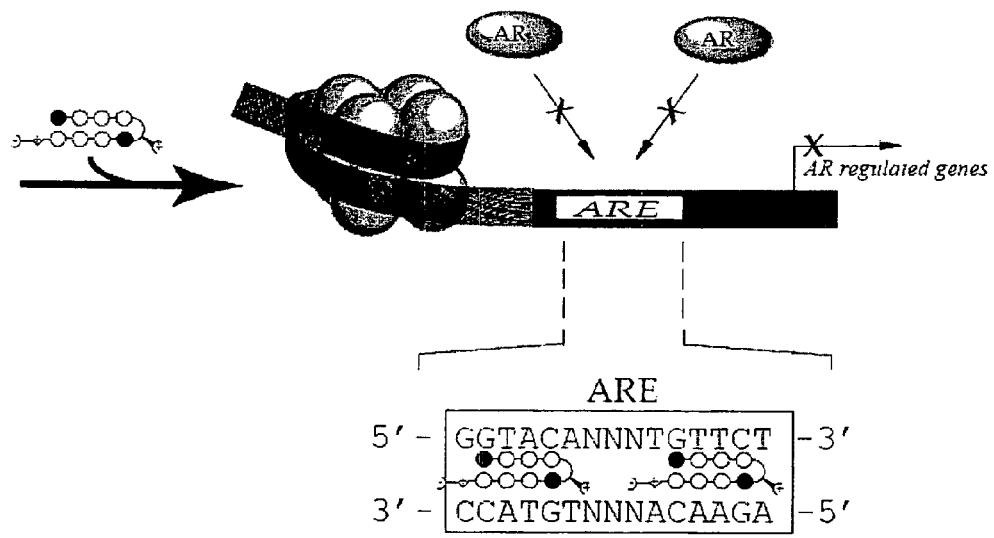
FIGURE 6A-B

A
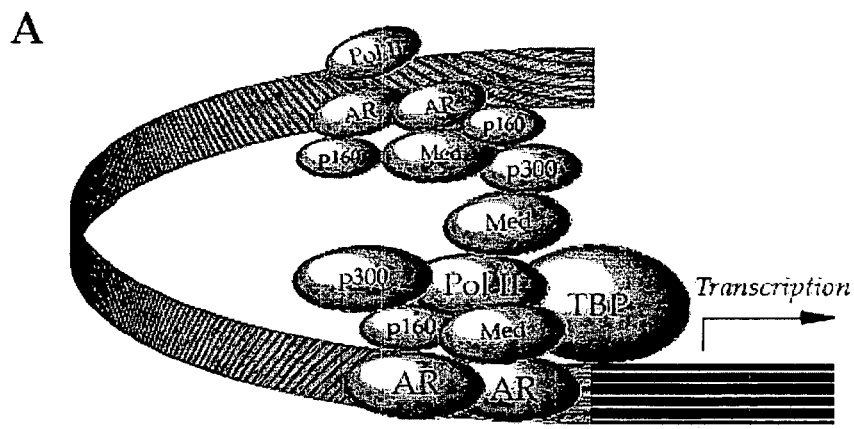
B  Consensus ARE
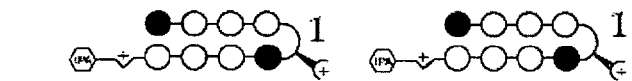
C
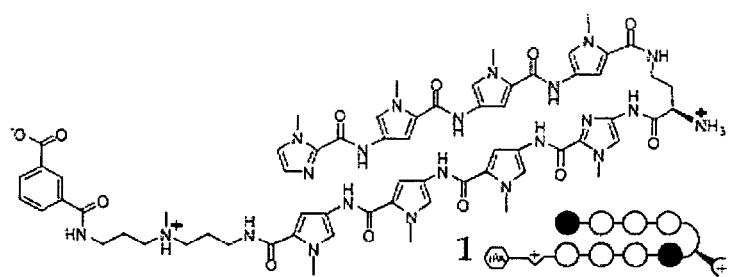
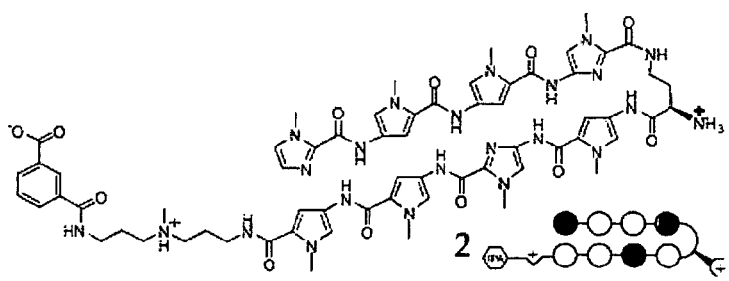
FIGURE 7A-C

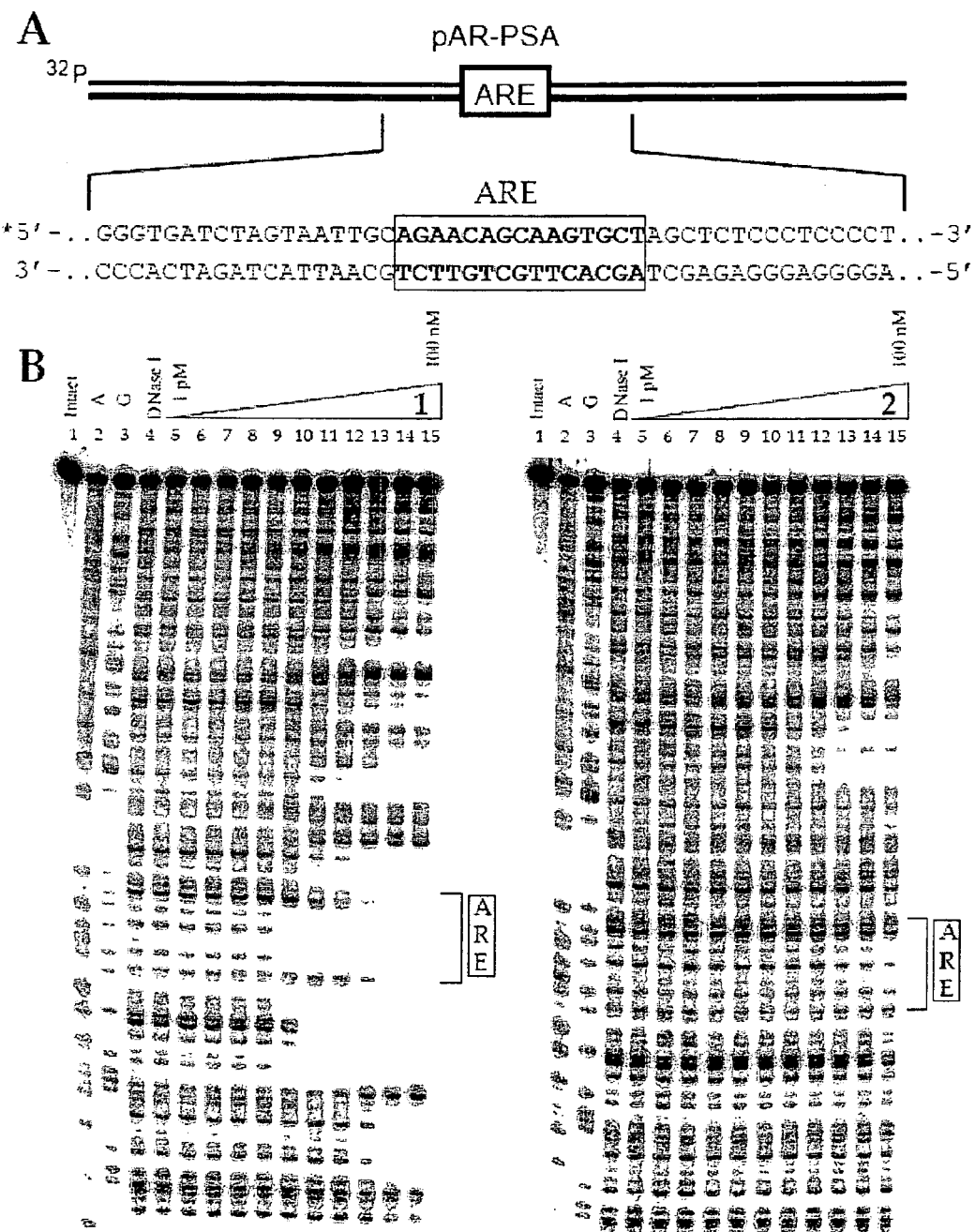
FIGURE 8A-B

C
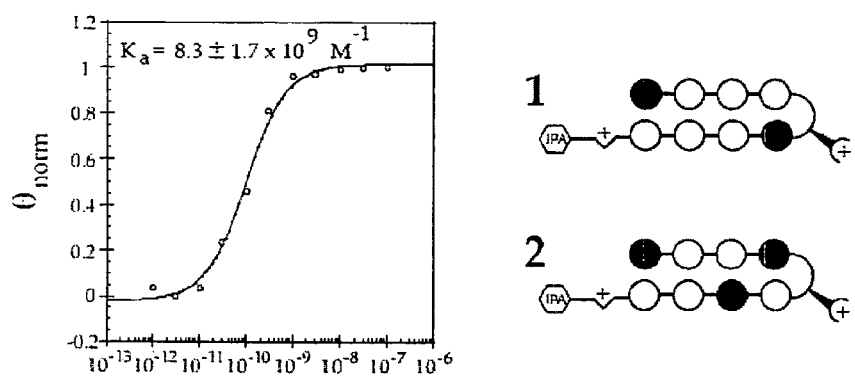
D
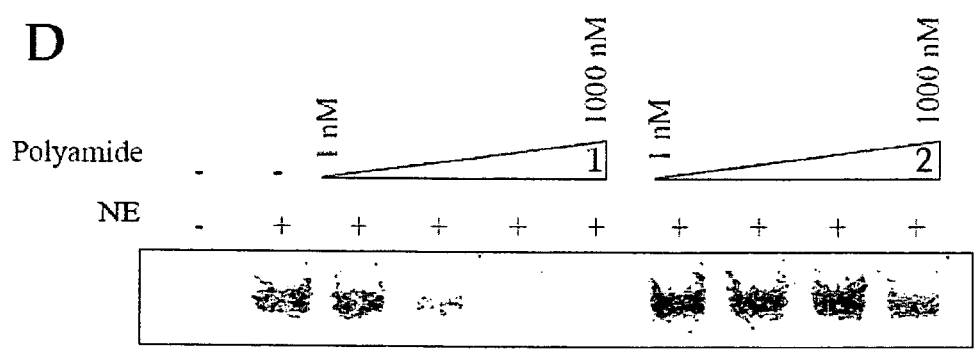
FIGURE 8C-D

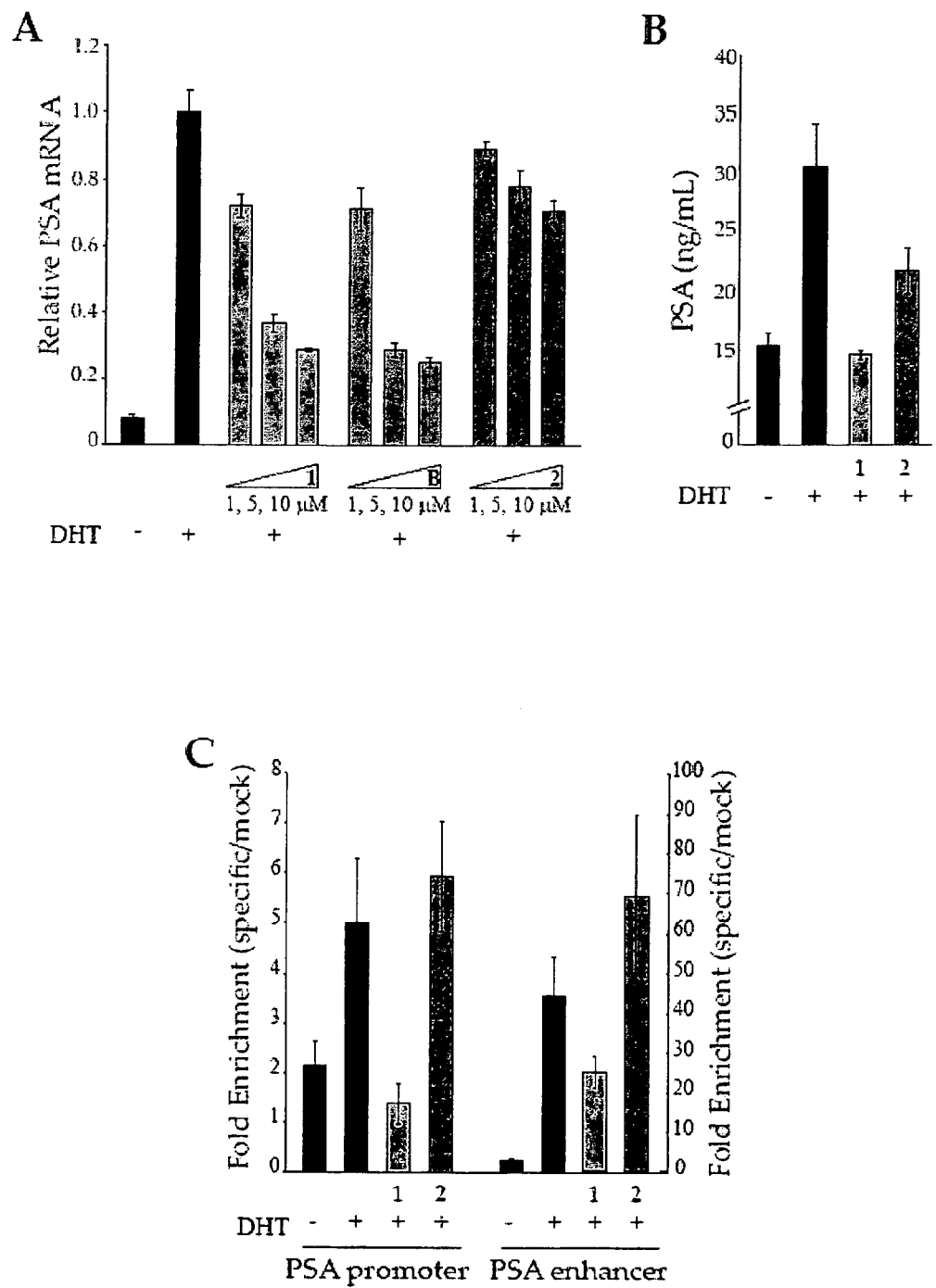
FIGURE 9A-C

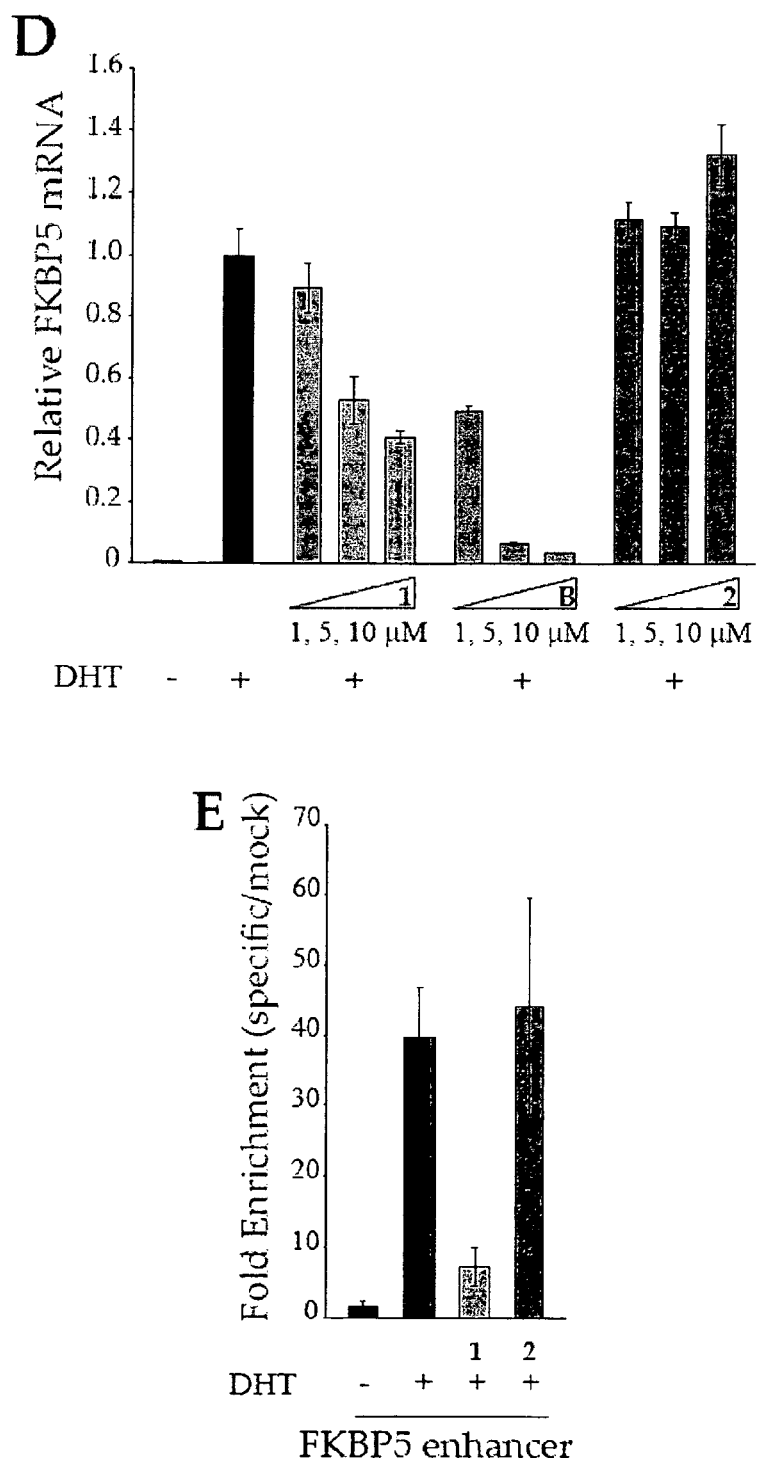
FIGURE 9D-E

B
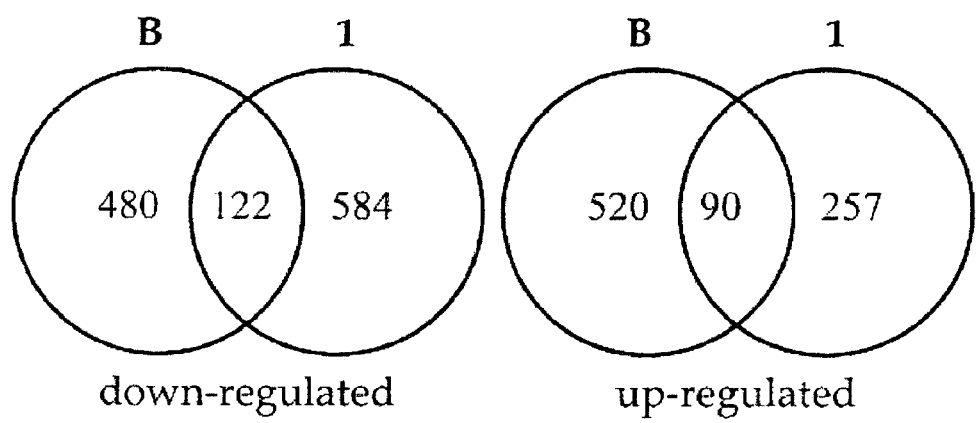
down-regulated      up-regulated
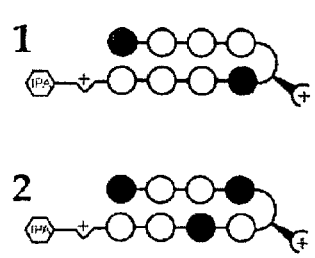
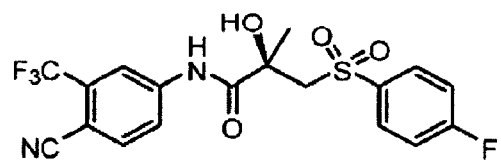
bicalutamide (*Casodex*)
FIGURE 10B

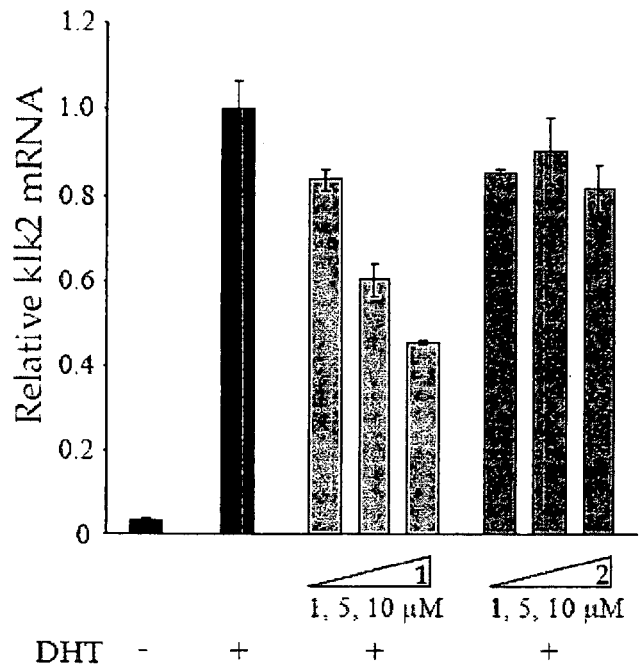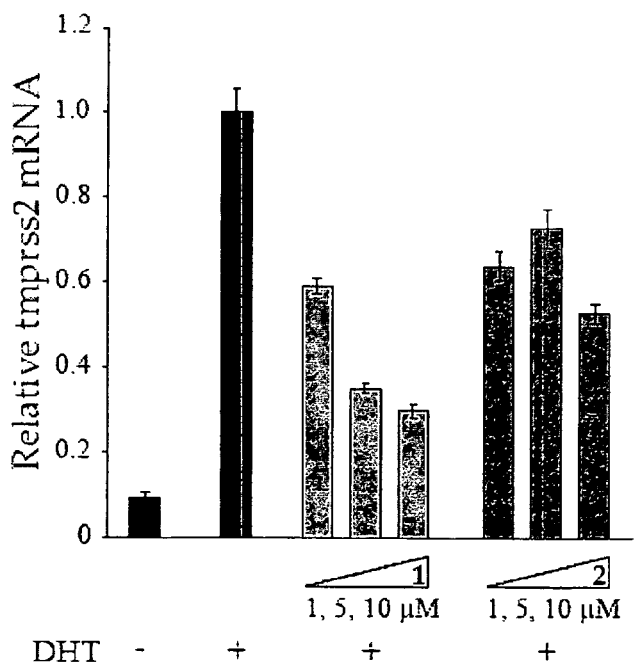
FIGURE 11A-B

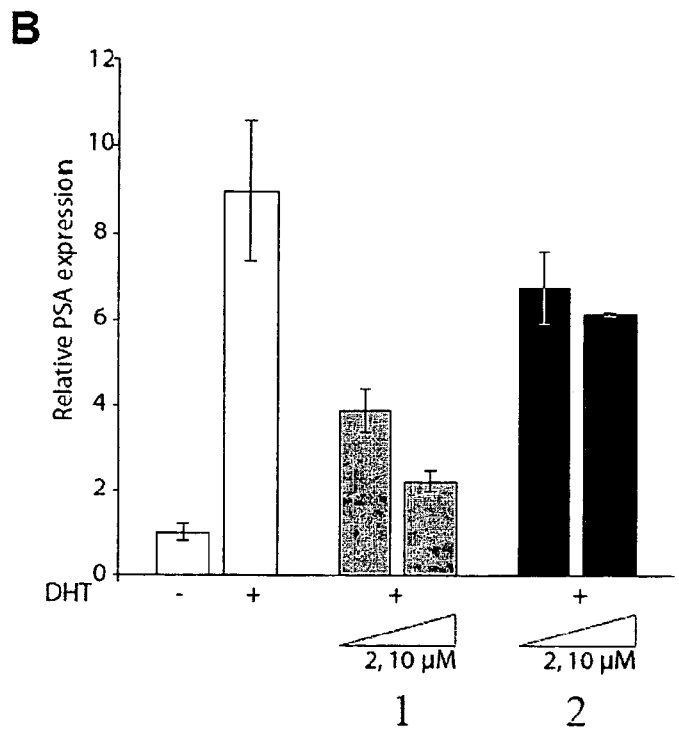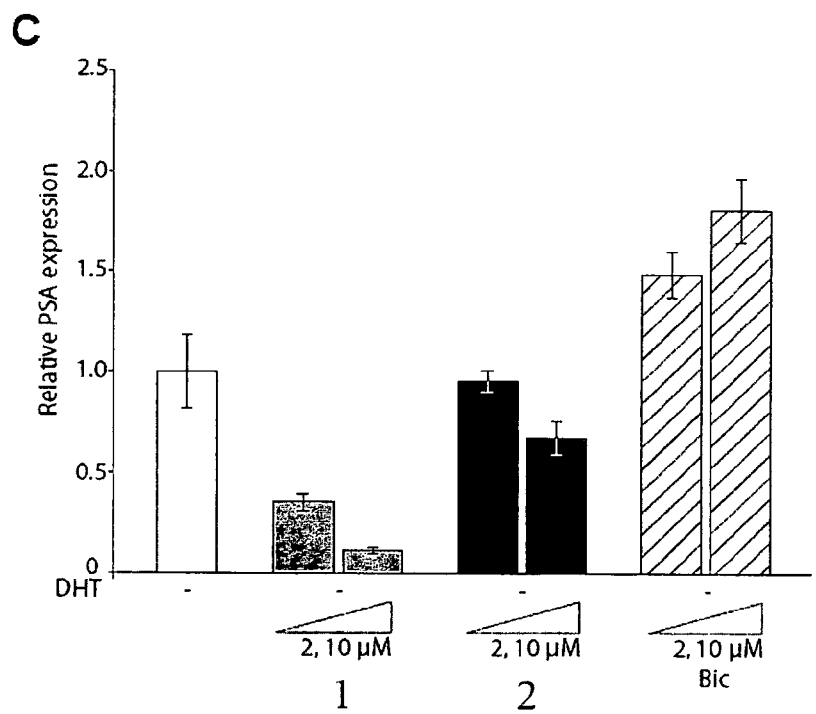
FIGURE 12B-C

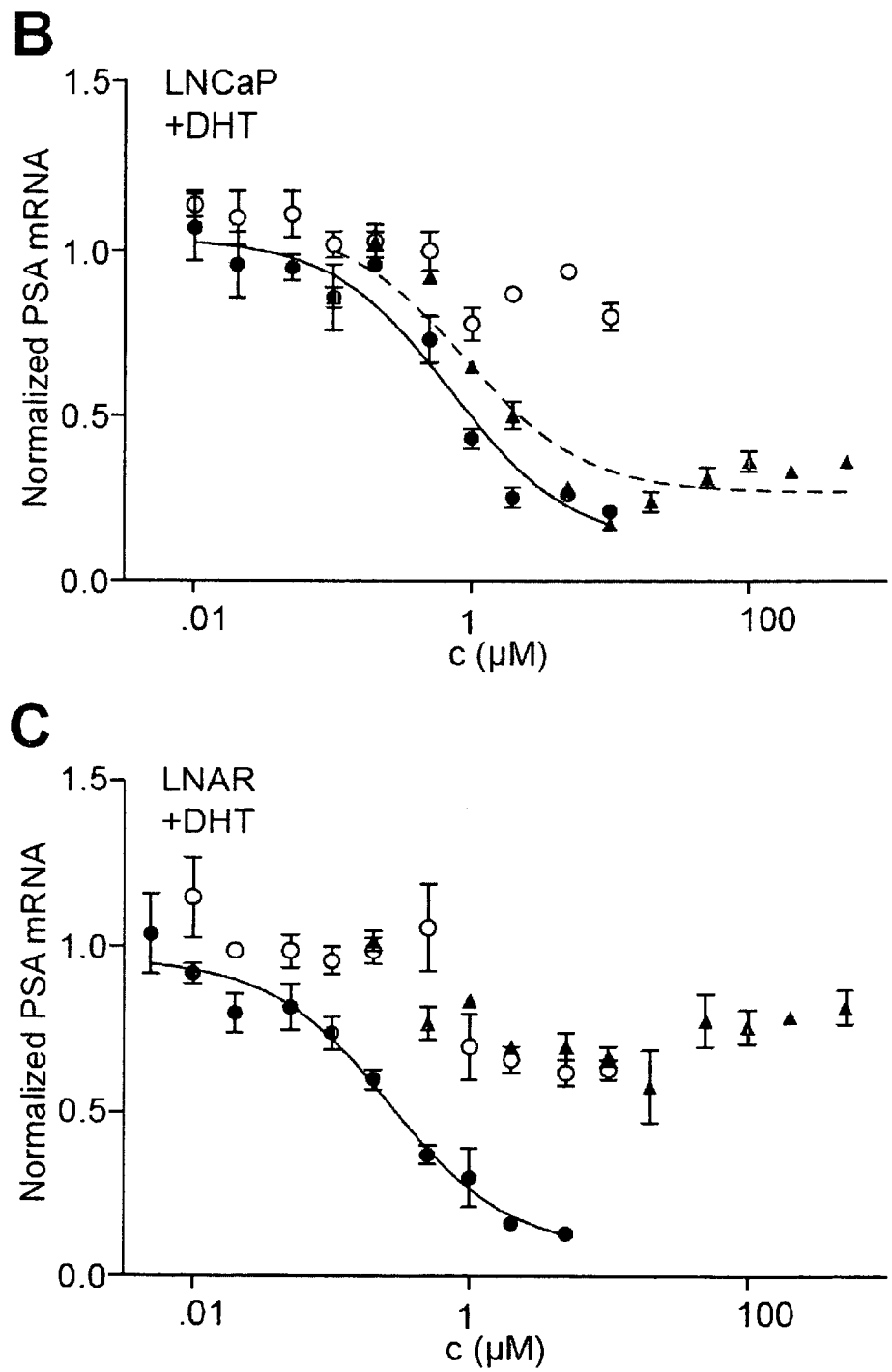
FIGURE 13B-C

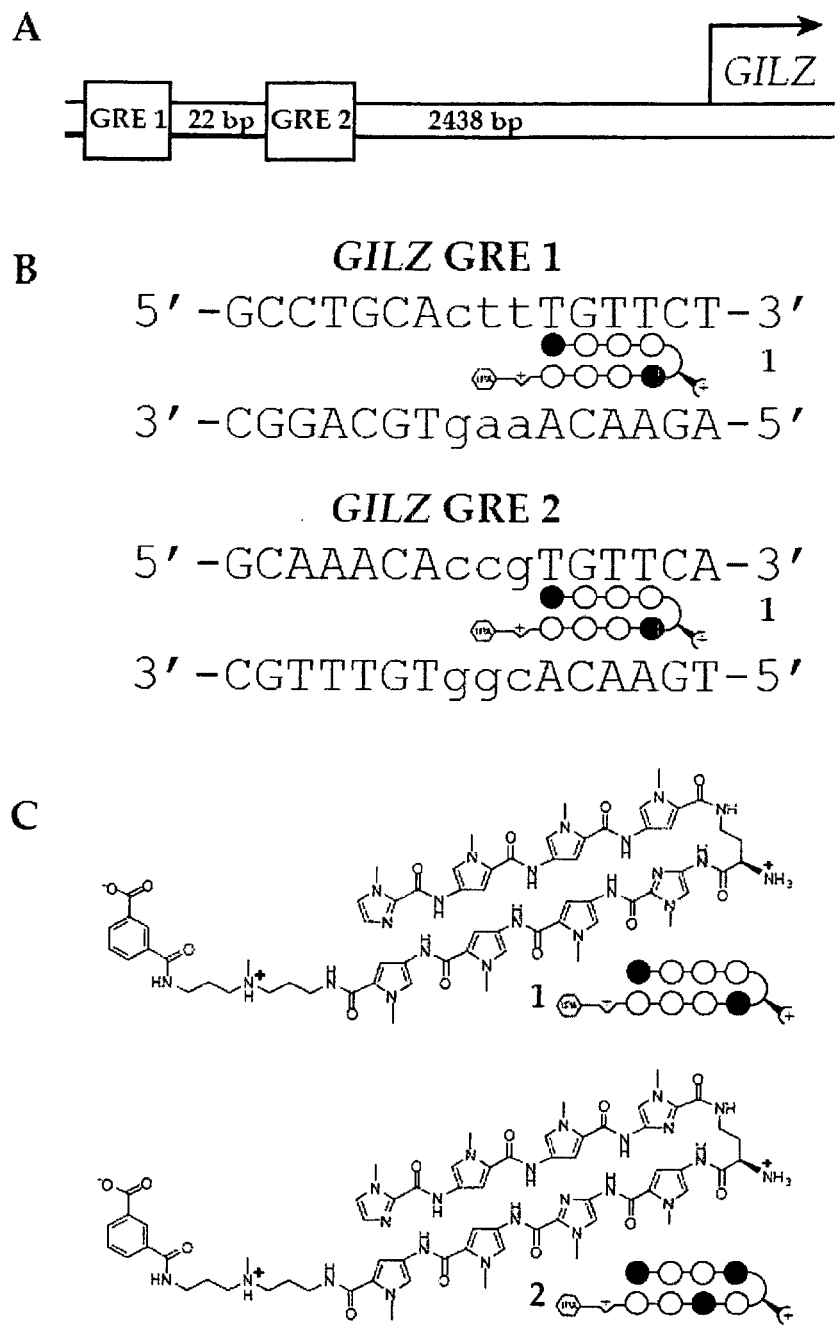
FIGURE 15A-C

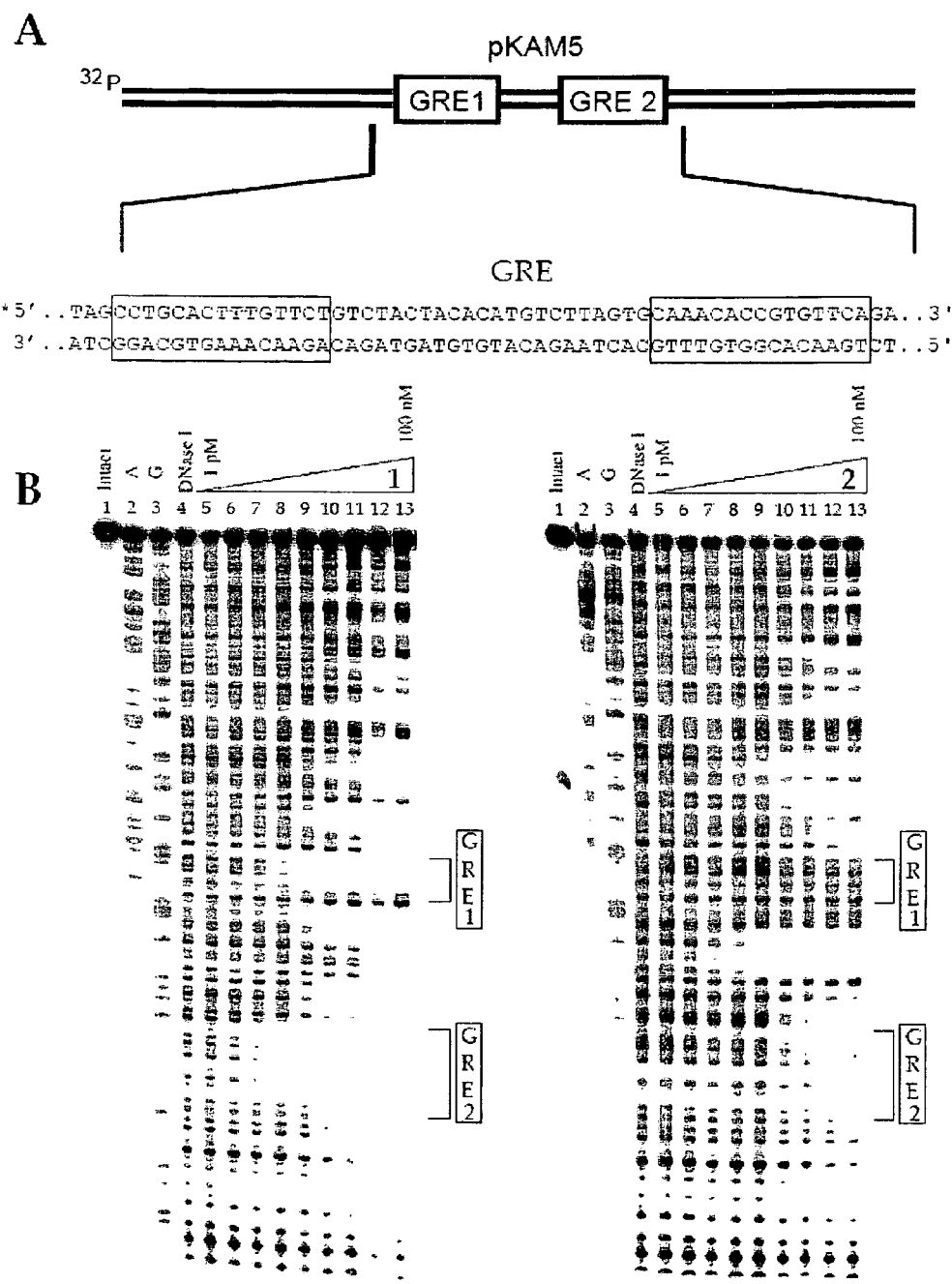
FIGURE 16A-B

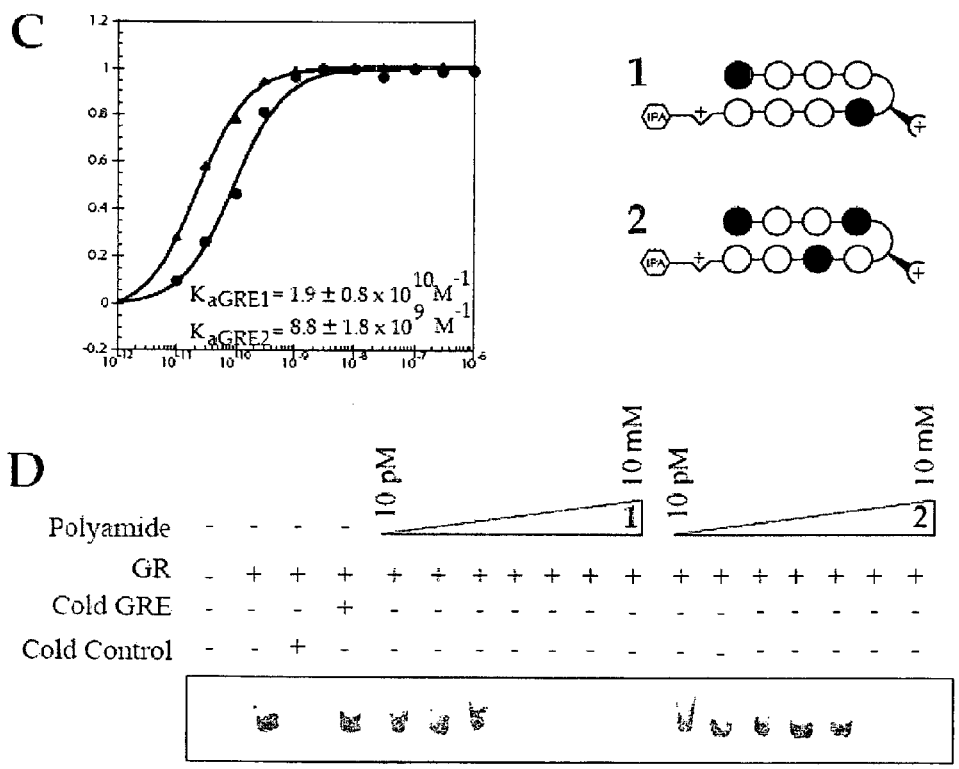
FIGURE 16C-D

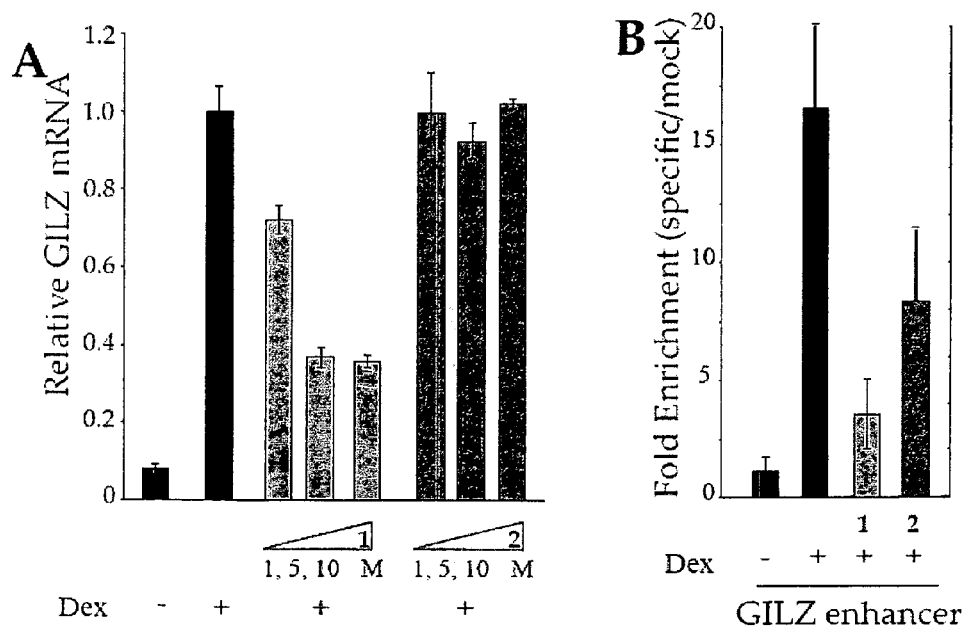
FIGURE 17A-B

A:
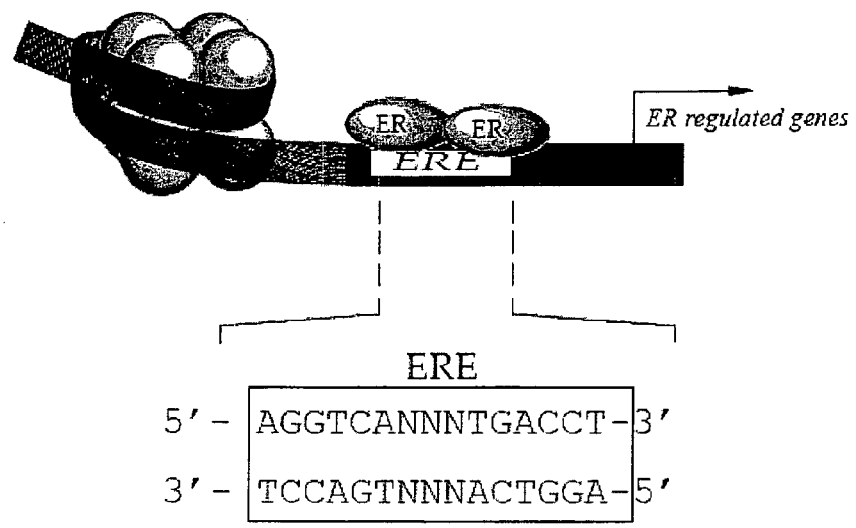
B:
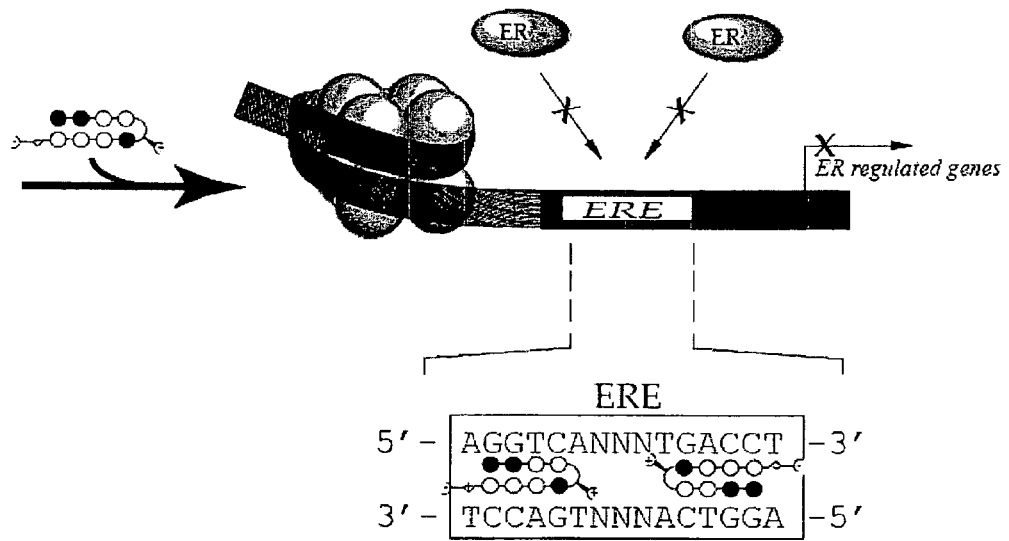
FIGURE 18A-B

US 8,835,480 B2

INHIBITORS FOR STEROID RESPONSE ELEMENTS AND RELATED METHODS

This application claims the benefit of U.S. Provisional Application No. 60/926,080, filed Apr. 23, 2007, which is incorporated herein by reference in its entirety.

The U.S. Government has certain rights in this invention pursuant to Grant No. GM051747 awarded by the National Institutes of Health.

FIELD OF THE INVENTION

Polyamides that inhibit ARE-, GRE- and ERE-mediated gene regulation are described. The polyamides are useful, for example, to down regulate gene regulation or expression modulated by AR, GR and ER, and to methods to treat related diseases.

BACKGROUND

Genes in higher organism are regulated through binding of regulatory molecules to regulatory sequences which may be in the gene or operatively linked to the gene. A variety of regulatory sequences are known. Among the gene regulatory molecules are steroids which typically bind receptor molecules to form a complex that can bind DNA to modulate gene expression. Androgens, glucocorticoids and estrogens are examples of steroids capable gene regulation through DNA sequences called androgen response element (ARE), glucocorticoid response element (GRE), and estrogen response element (ERE), respectively. Androgens form complexes with an androgen receptor (AR) to bind an ARE. Glucocorticoids form complexes with a glucocorticoid receptor (GR) to bind a GRE. Estrogens form complexes with an estrogen receptor (ER) to bind ERE. The AR, GR, and ER share a highly conserved DNA-binding domain. This domain, related to the classical Cys-2-His-2 zinc finger motifs, contains two modules of zinc coordinated by four cysteines.

AR signaling regulates for example normal prostate development and contributes to the progression of prostate cancer. Drug therapies that act to limit circulating androgen levels or directly antagonize ligand binding to AR initially slow prostate cancer growth but nearly all patients treated with such anti-androgen therapies will eventually develop hormone-refractory disease. Dysregulation of AR activity is thought to contribute to this transition. Up-regulation of AR mRNA, mutations in the AR itself, and ligand-less activation of AR through other signaling pathways contribute to this dysregulation. Direct antagonism of AR-DNA binding could inhibit androgen receptor activity in hormone-refractory conditions where androgen antagonists that target the ligand-binding pocket are ineffective.

ARE, GRE and ERE mediated gene regulation are involved in diseases including cancer. Inhibition of ARE-, GRE- and ERE-mediated gene regulation would be highly desirable in the treatment of diseases. Inhibiting ARE-, GRE- and ERE-mediated gene regulation requires, for example, selectively down-regulating the binding of natural regulators in a cell to the ARE, GRE and ERE. Inhibition of ARE and GRE mediated gene expression has been attempted through binding of small molecules to the ligand binding domains of the AR or GR to prevent binding of the AR or GR to AREs or GREs, or to prevent a transcriptionally active complex of AR or GR at AREs or GREs. Examples of such attempts are anti-androgen drugs (for example, flutamide and bicalutamide).

A different approach involves inhibiting the binding of AR, GR or ER to the ARE, GRE or ERE by occupying ARE, GRE or ERE with a molecule capable of specifically recognizing an ARE, GRE or ERE. Inhibition through specific binding of ARE, GRE or ERE would be an effective way to modulate gene expression, for example, to treat diseases like cancer. Inhibitors of ARE-, GRE-, and ERE-mediated gene regulation should be able to enter cells and to enter the nucleus of the cells. Such inhibitors should also be capable of accessing ARE, GRE and ERE sequences in the genome and they should not bind other sequences or molecules to a degree that would render them ineffective. Also, inhibitors should not accumulate in other organelles, for example lysosomes, to a degree that renders them ineffective.

Compounds capable of inhibiting ARE-, GRE- and ERE-mediated gene regulation would therefore be highly desirable. The present invention provides such compounds.

SUMMARY OF THE INVENTION

The present invention relates to polyamides capable of modulating ARE-, GRE-, and ERE-mediated gene regulation in a cell. Polyamides of the current invention, in certain embodiments, are capable of entering a cell and of binding ARE, GRE and ERE in the genome of the cell to inhibit binding of other molecules to the ARE, GRE and ERE.

Polyamides of the invention in certain embodiments comprise a structure 1, wherein each X is independently selected from CH, N, or COH (each p independently selected from 0 and 1), wherein each $R_2$ is independently selected from H, a $C_{1-10}$ alkyl, a $C_{1-10}$ alkenyl, a $C_{1-10}$ alkynyl, —$(CH_2)_q$—NH—$R_6$ (each q independently selected from 1-10). In structure 1, each pyrrole unit of structure 2 may be independently replaced by a beta-alanine of structure 3. Each $R_3$ and $R_4$, and/or each $R_1$ and $R_5$ in structure 1 may be covalently linked by a turn of any one of structures 4-6 to form a hairpin- or a cyclic-shaped molecule. Any $R_2$ may be covalently linked to another $R_2$ to form an H- or U-shaped molecule. Each $R_7$, $R_8$ and $R_9$ in structures 4 and 5 may be independently selected from an R or S isomer, and is independently selected from structures 7-17 (each s independently selected from 1-10). Each $R_1$ and $R_4$ (e.g., in structure 1), and each $R_{10}$ (e.g., in structures 14 and 16), is independently selected from structures 18 (each u independently selected from 0 and 1), with each A independently selected from structure 21. Each $R_3$ and $R_5$ (e.g., in structure 1), each $R_6$ (e.g., in $R_2$), and each $R_1$, (e.g., in structures 15 and 17), is independently selected from structures 19 and 20 (each v and w independently selected from 0 and 1), with each A' independently selected from structure 22, and with each Z independently selected from structures 23 and 24. Each $R_{12}$ is independently selected from structures 25-54 (each d, e, f, h and j independently selected from 1-10), with each y independently selected from structures 55-57. Each t is independently selected from 1-10. Each $R_{13}$ is independently selected from structures 58-74 (each g and e independently selected from 1-10). In $R_{12}$ and $R_{13}$, each $R_{14}$ represents one, two, three, four, or five sidechains of the ring (up to the maximum number) with each $R_{14}$ being independently selected from H, OH, SH, $CH_3$, $NH_2$, halogen, F, Cl, Br, or I, and each amide linkage of structure 75 that occurs in structures 42-59 may be independently replaced by a thiourea linkage of structure 76. Polyamides of the current invention, in certain preferred embodiments, comprise any one or more of structures 77-84.

The present invention also comprises methods to inhibit ARE-, GRE-, and ERE-mediated gene regulation, for example, by inhibiting the binding of ARE, GRE and/or ERE by another molecule, for example, a complex comprising an androgen and an AR, a complex comprising a glucocorticoid and a GR, a complex comprising an estrogen and an ER, or an AR, a GR or an ER not complexed to an androgen, a glucocorticoid, or an estrogen. In certain embodiments, a method of the invention is useful for the treatment of cancer.

The invention further provides methods of using a polyamide of the invention as a research tool and for therapeutic methods in humans, animals, and/or plants. Methods of the current invention preferably comprise administering a polyamide of the invention to a cell, a human, an animal and/or a plant to modulate the expression of a gene that is regulated through an ARE, a GRE, and/or an ERE and/or to modulate physiological processes linked to the expression of such a gene.

BRIEF DESCRIPTION OF THE DRAWINGS

FIG. 2: Structural elements of a polyamide shown in FIG. 1 are exemplified. FIG. 2B: Each $R_7$, $R_8$ and $R_9$ in structures 4 and 5 may be an R or S isomer, and is independently selected from structures 7-17 (each s independently selected from 1-10). FIG. 2C: Each $R_1$ and $R_4$ in structure 1, and each $R_{10}$ in structures 14 and 16, is structure 18 (each u independently selected from 0 and 1), with each A having structure 21. Each $R_3$ and $R_5$ in structure 1, each $R_2$ in $R_6$, and each $R_{11}$ in structures 15 and 17, is independently selected from structures 19 and 20 (each v and w independently selected from 0 and 1), with each A' having structure 22, and with each Z independently selected from structures 23 and 24 (each t independently selected from 1-10).

FIG. 3: Structural elements of a polyamide shown in FIGS. 1 and 2 are exemplified. FIGS. 3A-C: Each $R_{12}$ is independently selected from structures 25-54 (each d, e, f, h and j independently selected from 1-10), with each y independently selected from structures 55-57. FIGS. 3D-E: Each $R_{13}$ is independently selected from structures 58-74 (each g and e independently selected from 1-10). In $R_{12}$ and $R_{13}$, each $R_{14}$ represents one, two, three, four, or five sidechains of the ring (up to the maximum number) with each $R_{14}$ being independently selected from H, OH, SH, $CH_3$, $NH_2$, halogen, F, Cl, Br, or I, and each amide linkage of structure 75 in structures 42-59 may be independently replaced by a thiourea linkage of structure 76. Each t is independently selected from 1-10.

FIG. 6: Illustration of the binding of androgen receptor (AR) to androgen response elements (ARE) (SEQ ID NOS:1, 2) in the promoters and enhancers of target genes resulting in a modulation of the level of gene expression. The ARE is targeted and bound by one or more pyrrole-imidazole containing polyamides that prevent or displace androgen receptor, modifying the expression of androgen receptor regulated genes.

FIG. 7: (A) Model of the androgen receptor (AR) transcription complex. (B) Consensus androgen response element (SEQ ID NOS:1, 2). (C) Structures and ball-and-stick models of polyamide 1 (structure 77, FIG. 4), designed to bind the consensus ARE, and 2, a mismatch. Imidazole and pyrrole units are represented by closed and open circles, respectively. The isophthalic acid tail moiety is represented by a hexagon.

FIG. 8: Binding of 1 and 2 to the ARE in the PSA promoter. (A) Illustration of pAR and partial sequence of the PSA promoter (SEQ ID NOS:3, 4). (B) Quantitative DNase I footprint titration experiments for polyamides 1 and 2 on the 5'-end-labeled PCR product of plasmid pAR-PSA: lane 1, intact DNA; lane 2, A reaction; lane 3, G reaction; lane 4, DNAse I standard; lanes 5-15, 1 pM, 3 pM, 10 pM, 30 pM, 100 pM, 300 pM, 1 nM, 3 nM, 10 nM, 30 nM, 100 nM polyamide, respectively. (C) Isotherm for 1 binding to the ARE half site 5'-AGAACA-3'. Polyamide 1 has a $K_a=8.3\pm1.7\times10^9$ for this site. Polyamide 2 shows no measurable binding in the footprinted region. (D) EMSA of DHT-stimulated LNCaP cell nuclear extract (NE) binding to a 31 base pair oligonucleotide duplex containing the PSA promoter ARE in the presence of 1 and 2.

FIG. 9: Inhibition of DHT-induced PSA and FKBP5 expression by 1 and 2. (A) Induction of PSA mRNA in the presence of 1, 2, and bicalutamide, B, measured by quantitative real-time PCR. 1 and bicalutamide inhibit expression of PSA in a dose-dependent manner up to approximately 70% at 10 μM. 2 has a more modest effect. (B) Secreted PSA protein measured by ELISA. (C) Chromatin immunoprecipitation assays with anti-AR or mock antibody treatment expressed as fold-enrichment (specific/mock) of DNA sequences at the PSA promoter and enhancer. AR occupancy at the PSA promoter and enhancer is decreased in the presence of 1 (10 μM) but not 2. (D) Induction of FKBP5 mRNA in the presence of 1, 2, and bicalutamide, B. (E) Chromatin immunoprecipitation assays with anti-AR at the FKBP5 fifth intron enhancer. Polyamide concentrations are 10 μM.

FIG. 11: DHT-induction of KLK2 mRNA (A) and TMPRSS2 mRNA (B) in the presence of 1, 2 measured by quantitative real-time PCR.

FIG. 15. (A) Model of the glucocorticoid receptor response elements in the GILZ enhancer. (B) ball-and-stick models of polyamide 1, expected to bind the consensus GRE (SEQ ID NOS:5, 6), and 2, a mismatch (SEQ ID NOS:7, 8). (C) Structures of polyamide 1 and 2. Imidazole and pyrrole units are represented by closed and open circles, respectively. The isophthalic acid tail moiety is represented by a hexagon.

FIG. 16. Binding of 1 and 2 to the GRE in the GILZ enhancer. (A) Illustration of pKAM5 and partial sequence of the GILZ enhancer (SEQ ID NOS:9, 10). (B) Quantitative DNase I footprint titration experiments for polyamides 1 and 2 on the 5'-end-labeled PCR product of plasmid pKAM5: lane 1, intact DNA; lane 2, A reaction; lane 3, G reaction; lane 4, DNAse I standard; lanes 5-15, 1 pM, 3 pM, 10 pM, 30 pM, 100 pM, 300 pM, 1 nM, 3 nM, 10 nM, 30 nM, 100 nM polyamide, respectively. (C) Isotherm for 1 binding to the GRE1 and GRE2 sites. Polyamide 1 has a $K_a=1.9\pm0.8\times10^{10}$ for GRE1 and $K_a=8.8\pm1.8\times10^9$ for GRE2. (D) EMSA of glucocorticoid receptor binding to an oligonucleotide duplex containing the GILZ enhancer GRE1 and GRE2 in the presence of 1 and 2.

FIG. 17. Inhibition of dexamethasone-induced GILZ expression by 1 and 2. (A) Induction of GILZ mRNA in the presence of 1, 2, measured by quantitative real-time PCR. 1 inhibits expression of GILZ in a dose-dependent manner up to approximately 60% at 10 µM. 2 has a more modest effect. (B) Chromatin immunoprecipitation assays with anti-GR or mock antibody treatment expressed as fold-enrichment (specific/mock) of DNA sequences at the GILZ enhancer. GR occupancy at the GILZ enhancer is decreased in the presence of 1 (10 µM).

FIG. 18: (A) Illustration of the binding of an estrogen receptor (ER) to estrogen response elements (ARE) in the promoters and enhancers of target genes resulting in a modulation of the level of gene expression. (B) The ERE is targeted and bound by one or more pyrrole-imidazole containing polyamides that prevent or displace the receptor, modifying the expression of estrogen receptor regulated genes.

DETAILED DESCRIPTION OF THE INVENTION

The present invention relates to compositions capable of modulating the activity of an ARE, a GRE and/or an ERE. In certain embodiments, a composition of the invention comprises a polyamide, preferably a polyamide capable of binding an ARE, a GRE and/or an ERE in DNA, for example, in genomic DNA. A polyamide of the invention, in certain embodiments, is capable of modulating the expression of a gene that is regulated by an ARE, a GRE and/or an ERE. In certain preferred embodiments, a polyamide of the invention is capable of entering a cell and modulating the expression of a gene that regulated by an ARE, a GRE and/or an ERE.

5.1 Polyamides of the Invention

Figure 1:
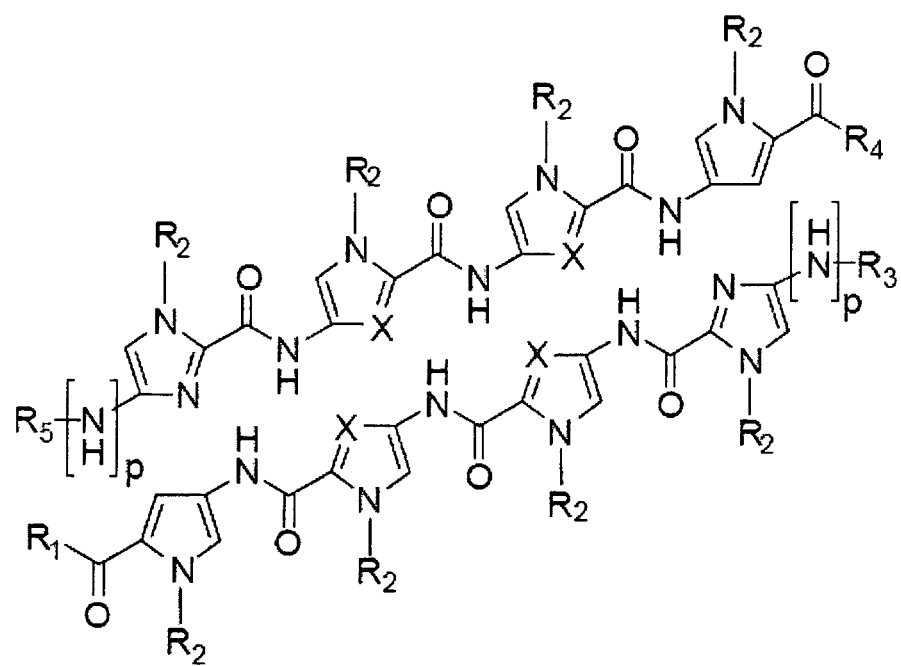
FIG. 1: Polyamides of certain embodiments of the invention are shown as structure 1.
Figure 2A:
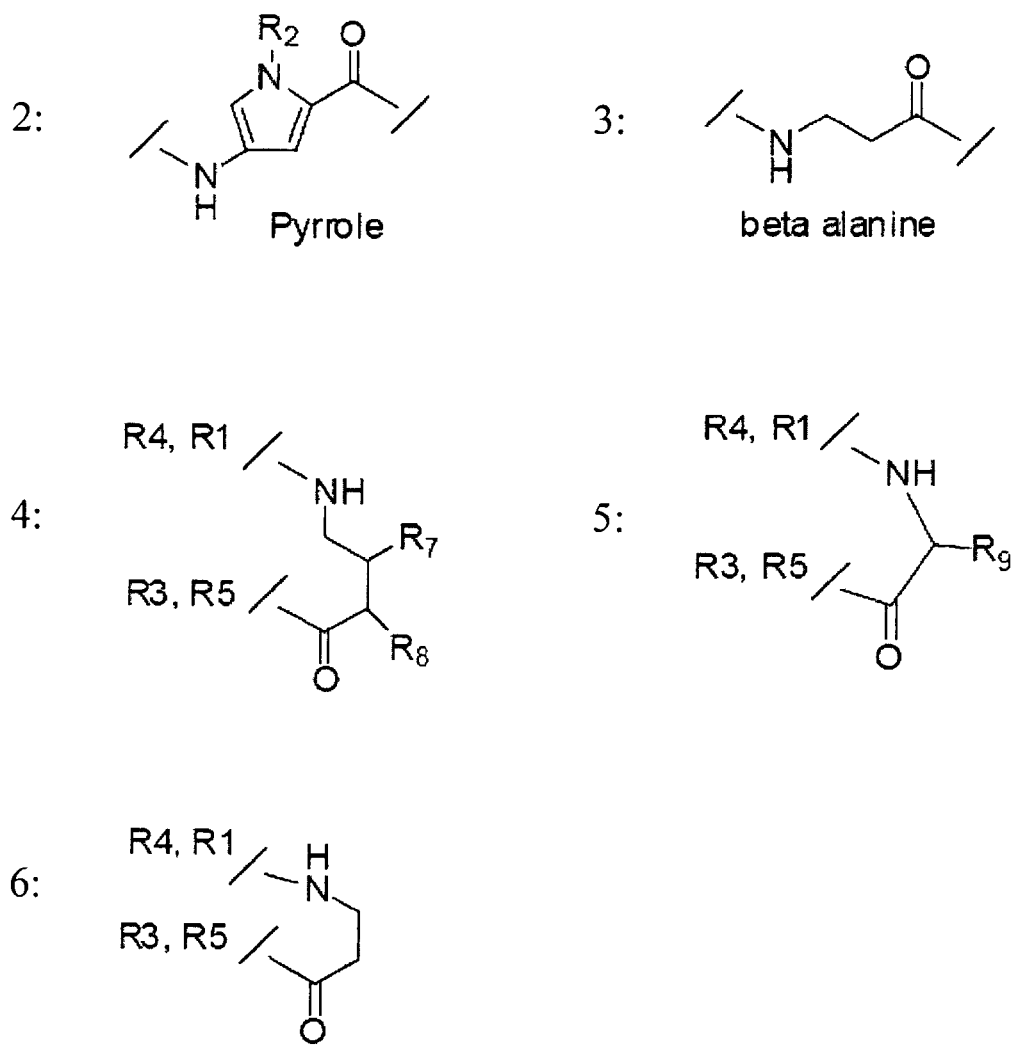
FIG. 2A: Any pyrrole unit of structure 2 in structure 1 may be independently replaced by beta alanine structure 3. Any turn in structure 1 may be independently selected from structures 4-6.
Figure 3B:
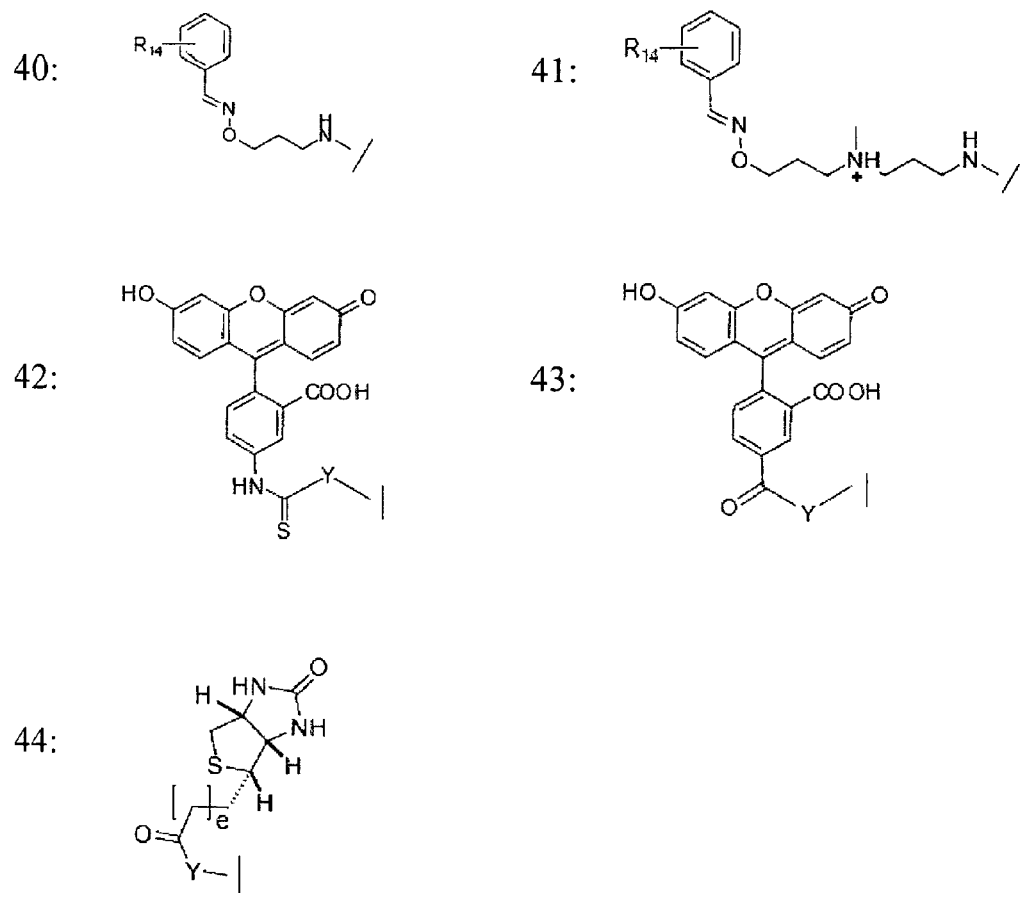
Figure 4A:
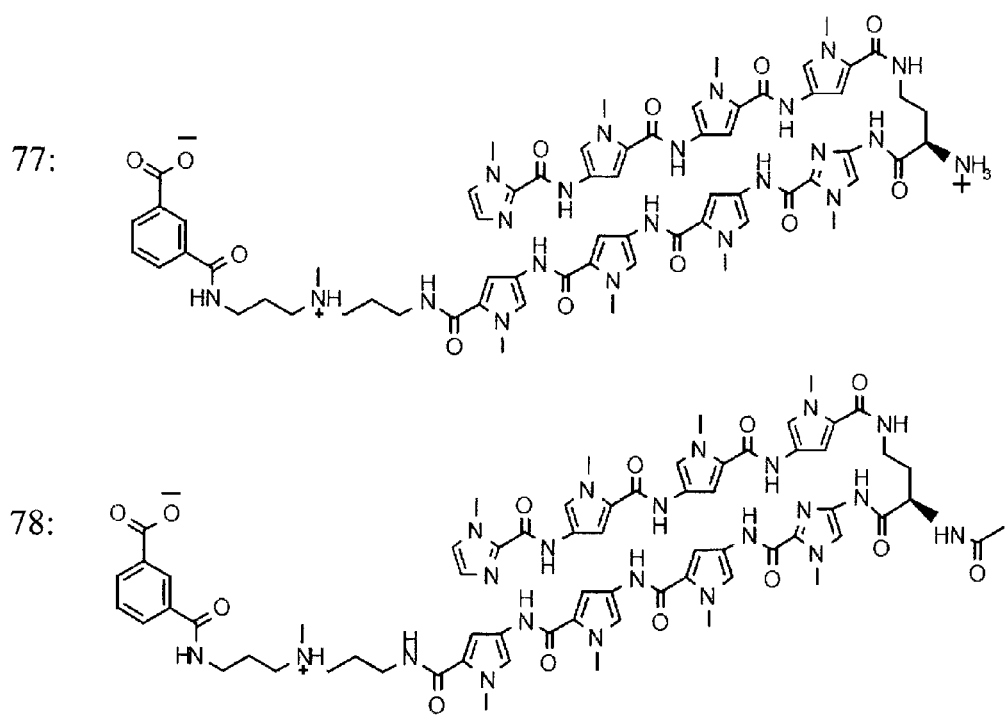
FIG. 4: Polyamides of certain embodiments of the invention are shown in FIGS. 4A-D as structures 77-84.
Figure 4B:
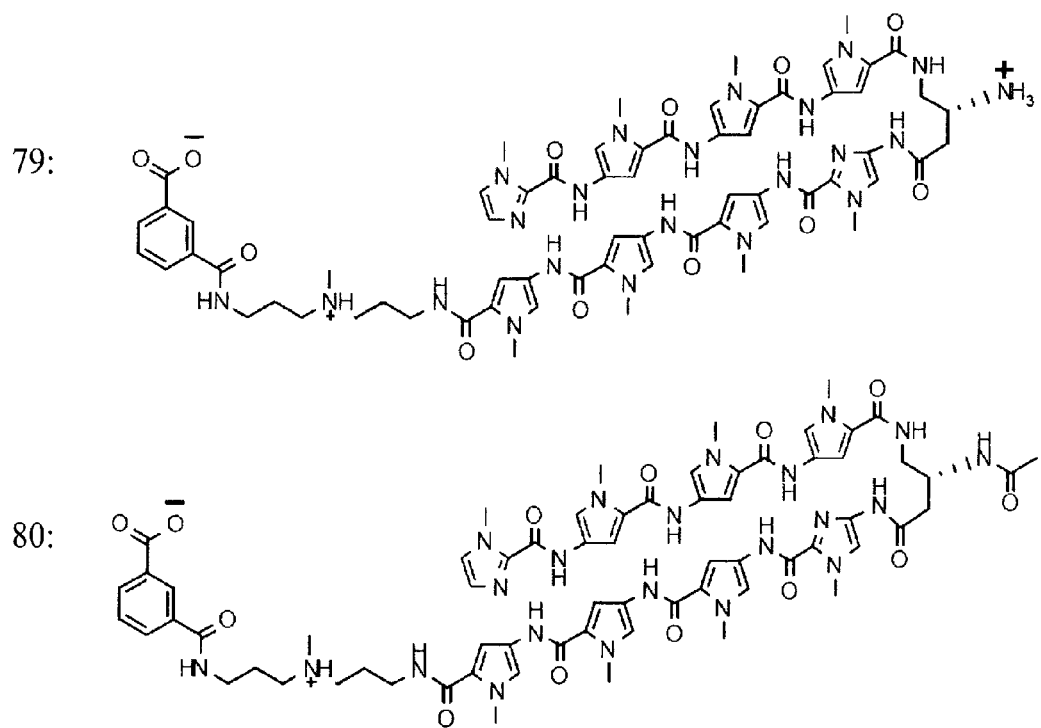
Figure 4C:
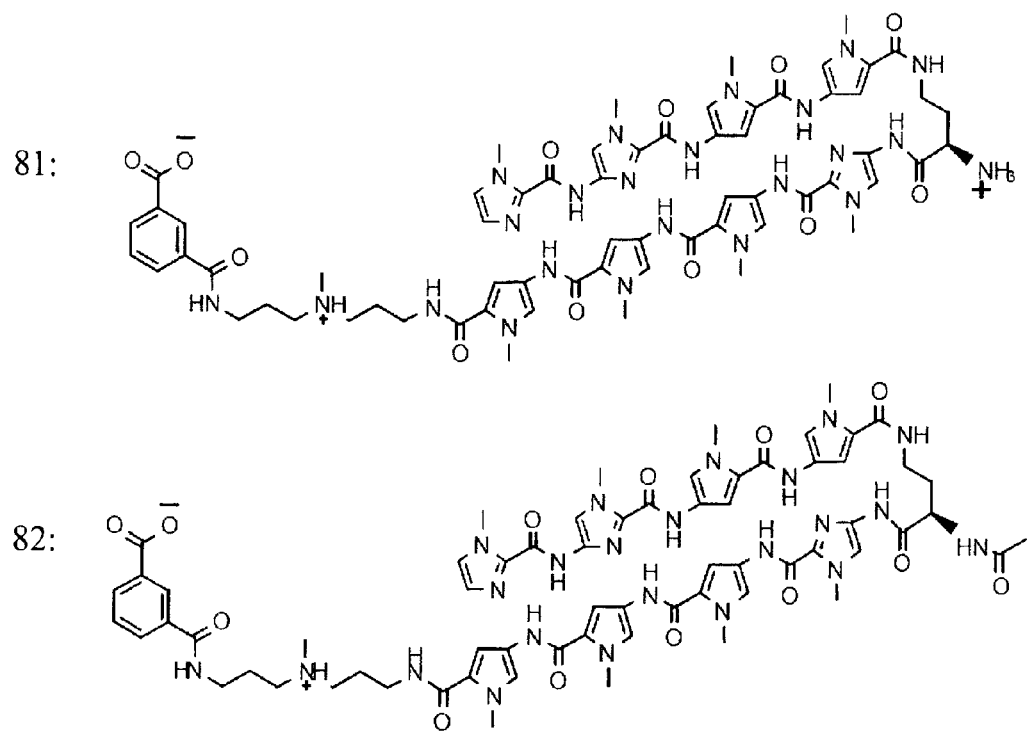
Figure 4D:
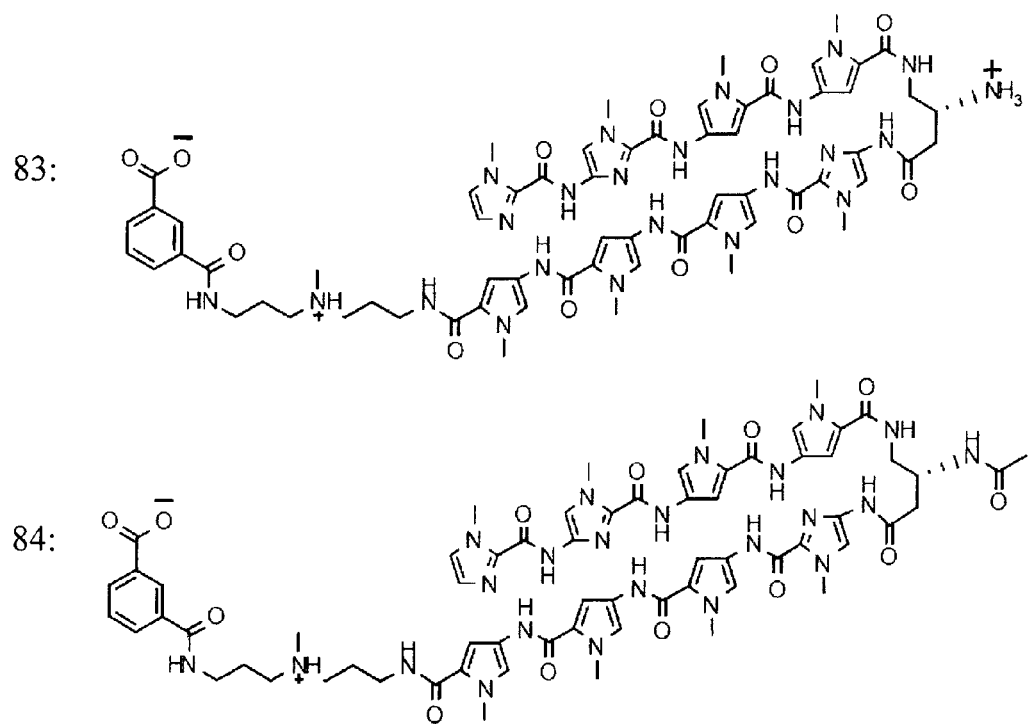
Figure 5:
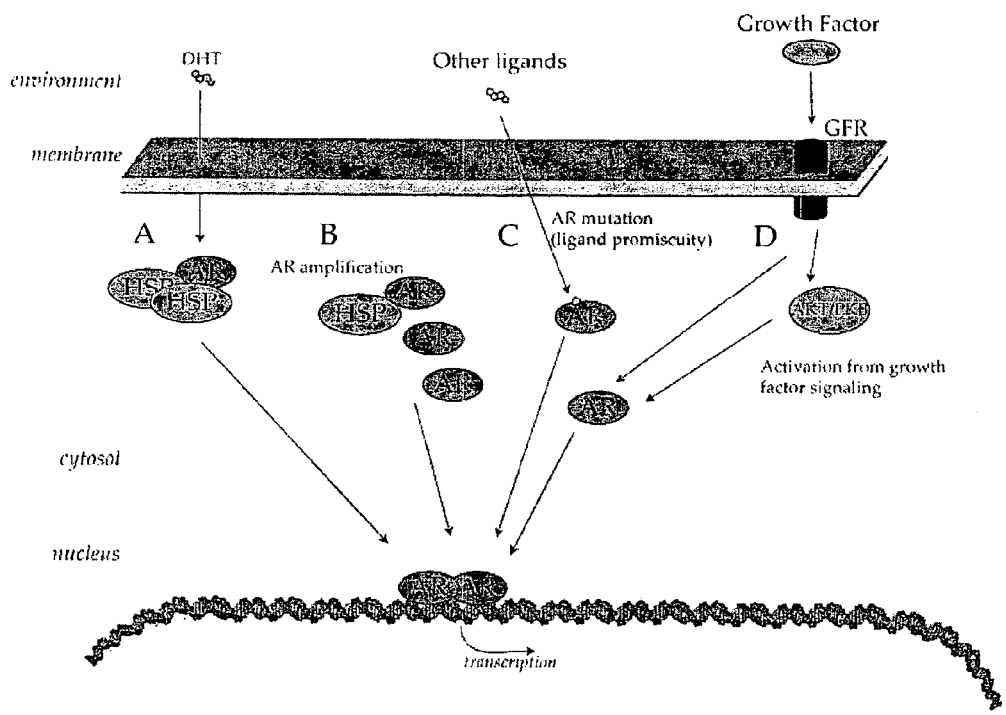
FIG. 5: Androgen receptor activation in androgen independent prostate cancer (A) Normal activation of AR by DHT. (B) AR amplification leads to activation. (C) Mutations in AR leads to promiscuity for other ligands. (D) Ligand-independent activation by upstream signaling.

A polyamide of the invention, in certain embodiments, has structure 1 (FIG. 1). A polyamide of structure 1 may be one molecule, for example, if R1, R5, R3, R4 are linked through a turn of any one of structures 4-6, or two molecules, for example, a homodimer or a heterodimer. A monomer of a polyamide of structure 1 is capable of binding DNA independently of another monomer of a polyamide of structure 1 but preferably as part of a homodimer or heterodimer with another monomer of a polyamide of structure 1. Monomers of a homodimer or heterodimer of structure 1 are capable of binding DNA so that the monomers bind DNA side-by-side to each other, or within close proximity (for example, at sites that are separated by less than 10 base pairs, or by less than 50 base pairs).

Polyamides of the invention in certain embodiments comprise a structure 1, wherein each X is independently selected from CH, N, or OH (each p independently selected from 0 and 1), wherein each $R_2$ is independently selected from H, a $C_{1-10}$ alkyl, a $C_{1-10}$ alkenyl, a $C_{1-10}$ alkynyl, —(CH2)$_q$—NH—$R_6$ (each q independently selected from 1-10). In structure 1, each pyrrole unit of structure 2 may be independently replaced by a beta-alanine of structure 3. Each $R_3$ and $R_4$, and/or each $R_1$ and $R_5$ in structure 1 may be covalently linked by a turn of any one of structures 4-6 to form a hairpin- or a cyclic-shaped molecule. Any $R_2$ may be covalently linked to another $R_2$ to form an H- or U-shaped molecule. Each $R_7$, $R_8$ and $R_9$ in structures 4 and 5 may be independently selected from an R or S isomer, and is independently selected from structures 7-17 (each s independently selected from 1-10). Each $R_1$ and $R_4$ (e.g., in structure 1), and each $R_{10}$ (e.g., in structures 14 and 16), is independently selected from structures 18 (each u independently selected from 0 and 1), with each A independently selected from structure 21. Each $R_3$ and $R_5$ (e.g., in structure 1), each $R_6$ (e.g., in $R_2$), and each $R_{11}$ (e.g., in structures 15 and 17), is independently selected from structures 19 and 20 (each v and w independently selected from 0 and 1), with each A' independently selected from structures 22, and with each Z independently selected from structures 23 and 24. Each $R_{12}$ is independently selected from structures 25-54 (each d, e, f, h and j independently selected from 1-10), with each y independently selected from structures 55-57. Each t is independently selected from 1-10. Each $R_{13}$ is independently selected from structures 58-74 (each g and e independently selected from 1-10). In $R_{12}$ and $R_{13}$, each $R_{14}$ represents one, two, three, four, or five sidechains of the ring (up to the maximum number) with each $R_{14}$ being independently selected from H, OH, SH, $CH_3$, $NH_2$, halogen, F, Cl, Br, or I, and each amide linkage of structure 75 that occurs in structures 42-59 may be independently replaced by a thiourea linkage of structure 76. Polyamides of the current invention, in certain preferred embodiments, comprise any one or more of structures 77-84.

Polyamides of the present invention may be synthesized by any method known in the art, for example, by solid phase methods using compounds such as Boc-protected 3-methoxypyrrole, imidazole, pyrrole aromatic amino acids, and alkylated derivatives thereof, which are cleaved from the support by aminolysis, deprotected (e.g., with sodium thiophenoxide), and purified by reverse-phase HPLC, as well known in the art. The identity and purity of the polyamides may be verified using any of a variety of analytical techniques available to one skilled in the art such as $^1$H-NMR, analytical HPLC, and/or matrix-assisted laser-desorption ionization time-of-flight mass spectrometry (MALDI-TOF MS-monoisotropic). A tail-polyamide of the invention, in certain embodiments, may also comprise a protective group useful for purposes of polyamide synthesis, in certain other embodiments, a tail-polyamide does not comprise a protective group. Useful protective groups are known to those of skill in the art.

The aliphatic functionalities of linkable units can be provided, for example, by condensation of β-alanine or dimethylaminopropylamine during synthesis of the polyamide by methods well known in the art. Linkable units are typically supplied as amino acids, desamino acids, or descarboxy amino acids prior to amide bond formation by condensation methods well known in the art to form linking amide groups. The term "amino acid" refers to an organic molecule containing both an amino group ($NH_2$) and a carboxylic acid (COOH). The term "desamino" refers to an amino acid from which the amino functionality has been removed. The term "descarboxy" refers to an amino acid from which the carboxylic acid functionality has been removed. The term "chemical probe" refers to chemical functionalities having properties that facilitate location and identification of polyamides functionalized (i.e., covalently bonded) by such chemical probes. A chemical probe does not include fluorescein. Methods of conjugating chemical probes to polyamides of the invention are well known in the art.

Tail-polyamides may be synthesized by any method known in the art, including methods discussed herein. Methods of synthesizing organic compounds that are useful in synthesizing a tail-polyamide of the invention are discussed, for example, in U.S. Pat. Nos. 7,087,378; 7,049,061; 6,958,240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are incorporated herein by reference in their entirety.

5.2 Modulation of Gene Expression Using Polyamides of the Invention

A polyamide of the invention is useful for modulating the expression of a gene. A polyamide of the invention in certain embodiments is capable of modulating the expression of a gene in a cell, preferably a living cell, and most preferably a cell in a higher organism, for example, a human, an animal, a dog, a cat, a pet, a farm animal, a cow, a pig, a chicken, a fish, or any other animal, or a plant. A polyamide of the invention in certain embodiments is capable of entering a cell and preferably the nucleus of the cell. In certain embodiments, a polyamide of the invention is useful for modulating gene expression in a cell in culture. In certain other embodiments, a polyamide of the invention is useful for modulating gene expression in a patient to ameliorate a disease symptom and/or to modulate a physiological process, for example, cell behavior, cell growth, cell secretion, cell signaling, cell death, or any other process.

A polyamide of the present invention is capable of binding double stranded (i.e., duplex) DNA at a specific sequence (i.e., the target DNA sequence or target sequence or target site) with high affinity and selectivity. A recitation of a sequence of DNA herein contemplates the recited single-stranded DNA, the complementary (i.e., Watson-Crick) sequence, and the duplex molecule comprising the recited and complementary strands of DNA.

A target site for a polyamide of the invention is an ARE, a GRE and/or an ERE. An ARE, in certain embodiments, comprises a consensus sequence of 5'-GGWACANNNTGTTCT-3' (SEQ ID NO:12) (with N=A, T, C, or G; and W=A or T) that is typically 15 base pairs in length and that is typically nearly palindromic. An ARE, in certain embodiments, comprises of two six base pair segments separated by a 3 base pair spacer. In certain other embodiments, an ARE comprises a consensus sequence of 5'-NGWACWNNNTGTYCN-3' (SEQ ID NO:13) (with N=A, T, C, or G; and W=A or T; and Y=T, G or A). In certain other embodiments, an ARE comprises six base pair half sites of the sequences 5'-TGTTCT-3', 5'-NGWACW-3' and 5'-TGTYCN-3' (with N=A, T, C, or G; and W=A or T; and Y=G or A), which may be a functional ARE without the presence of the full 15 base pair ARE present. Background on the ARE can be found in Roche P J et al., A consensus DNA-binding site for the androgen receptor. Mol Endocrinol. 1992 December; 6(12):2229-35; Massie C E et al., New androgen receptor genomic targets show an interaction with the ETS1 transcription factor. EMBO Rep. 2007 September; 8(9):871-8, which are incorporated herein by reference.

A GRE, in certain embodiments, comprises the sequence 5'-GGTACANNNTGTTCT-3' (SEQ ID NO:1) or a half-site of the sequence 5'-TGTTCT-3'. An ERE, in certain embodiments, comprises a 13 base pair sequence 5'-GGTCANNNT-GACC-3' or a half site of the sequence 5'-NGGTCA-3' (with N=A, T, C, or G). ER can also bind to six base pair half sites of the sequences, which can still be a functional ERE without the presence of a full 13 base pair ERE sequence. Background on the ERE can be found in Peale F V Jr et al., Properties of a high-affinity DNA binding site for estrogen receptor. Proc Natl Acad Sci USA. 1988 February; 85(4):1038-42, and Carroll J S et al., Genome-wide analysis of estrogen receptor binding sites. Nat Genet. 2006 November; 38(11):1289-97, which are incorporated herein by reference.

Proteins of the nuclear hormone receptor family of transcription factors have structures consisting of a ligand binding domain, an amino-terminal domain, a hinge domain, and a DNA binding domain. The DNA binding domain is largely conserved between the different nuclear hormone receptors, contains two modules of zinc coordinated by four cysteines, and is related to the classical Cys-2-His-2 zinc finger motifs of DNA binding proteins.

Most nuclear hormone response bind as homo- or hetero-dimmers to their respective response elements on DNA at particular gene regulatory sequences for their target genes. The steroid receptor subgroup, including androgen receptor, estrogen receptor, glucocorticoid receptor, progesterone receptor, and mineralocorticoid receptor, each bind typically as homo-dimers. The response elements typically consist of two six base pair sequences, "half-sites," that are separated by an intervening spacer sequence of one to five, usually three, nucleotides. For most nuclear receptor response elements, the first and sixth base pairs are both either A-T or T-A pairs, moving from 5' to 3'. The second and fifth are G-C and C-G, respectively, moving from 5' to 3'. The nucleotides at the third and fourth positions vary depending on the particular receptor, and the particular response element. The ARE and GRE half sites are often of the sequence 5'-TGTTCT-3',5'-NG-WACW-3', or 5'-TGT(G/T/A)CN-3', where W=A or T, and N=A, T, G, or C. The ERE half sites are often of the sequence 5'-NGGTCA-3'. The half sites for the response elements are often oriented as palindromes or semi-palindromes about the intervening spacer sequence. (Khorasanizadeh S, Rastinejad F. Nuclear-receptor interactions on DNA-response elements. Trends Biochem Sci. 2001 June; 26(6):384-90.)

DNA binding polyamides composed of eight heterocyclic rings of imidazole or pyrrole linked by amide linkages can be designed to bind to the six base pair half sites of nuclear receptors. A polyamide could be designed to bind at one or both half sites for a particular response element, or two different polyamides could be designed to bind at each half site for a particular response element, or two or more polyamides could be designed to bind at one or more of the response elements for a nuclear receptor at different loci in the genome.

A DNA binding polyamide that is targeted to bind to an ARE, GRE, or ERE, or another binding site for some other nuclear receptor, includes in its structure an imidazole opposite a pyrrole in the minor groove at the second base pair (a G-C pair) of the six base pair half site such that the exocyclic amine of the guanine can hydrogen bond with the lone pair nitrogen of the imidazole at this position. Additionally, such a polyamide would also include in its structure a pyrrole opposite an imidazole at the fifth base pair (a C-G pair), likewise so that the exocyclic amine of the guanine can hydrogen bond with the lone pair nitrogen of the imidazole at this position. The imidazole or pyrrole content at positions three and four of the six-base pair half site are determined by the particular base pair sequence that is to be targeted such that a G-C pair is presented with an imidazole-pyrrole pair, a C-G pair is presented with a pyrrole-imidazole pair, and either an A-T or T-A is presented with a pyrrole-pyrrole pair. For example, a polyamide targeted to bind an ERE containing a half site of the sequence 5'-AGGTCA-3' would in part comprise an imidazole opposite a pyrrole at the G-C base pair at the third position of the half site. This polyamide would present a pyrrole opposite a pyrrole at the T-A base pair at the fourth position. In another example, a polyamide targeted to an ARE containing a half site of the sequence 5'-TGTGCA-3' would in part comprise a pyrrole opposite a pyrrole at the third position T-A base pair, and an imidazole opposite a pyrrole at the G-C base pair at the fourth position. In another example, a polyamide targeted to a GRE containing the half site of the sequence 5'-TGTTCT-3' would in part comprise a pyrrole opposite a pyrrole at both the T-A base pairs at the third and fourth positions. For polyamides targeted to bind at such half sites, the tail and turn of the polyamide lie over the first and sixth positions of the half site.

As used herein, "subnanomolar affinity" means binding that is characterized by a dissociation constant, $K_d$, of less than 1 nM, as measured by DNase I footprint titration. In certain preferred embodiments, a polyamide of the present invention is characterized by subnanomolar affinity for ARE, GRE and/or ERE. As used herein, the "selectivity" of the binding of a polyamide to an ARE, GRE and/or ERE is the ratio of the dissociation constant, $K_d$, as measured by DNase I footprint titration, when binding the polyamide to a mismatch DNA sequence divided by the corresponding dissociation constant when binding the polyamide to the ARE, GRE and/or ERE. In certain preferred embodiments, polyamides of the present invention are characterized by a selectivity of 5 or greater, or about 5 or greater, or 10 or greater, or about 10 or greater, or 20 or greater, or about 20 or greater, or 50 or greater, or about 50 or greater, or 100 or greater, or about 100 or greater.

In certain preferred embodiments, a polyamide of the invention has at least 5-fold greater affinity for an ARE, GRE and/or ERE than for a site differing from the target site by one, two, or three nucleotides, or at least 10-fold, or at least 20-fold, or at least 50-fold, or at least 100-fold, or at least 200-fold, or at least 500-fold. Preferably, a polyamide of the invention will interact with an ARE, GRE and/or ERE with an affinity, as measured by DNase footprint titration, of less than 100 nM, or preferably less than 50 nM, or preferably less than 25 nM, or preferably less than 15 nM, or preferably less than 10 nM, or preferably less than 5 nM, or preferably less than 1 nM, or preferably less than 0.2 nM, or preferably less than 0.1 nM.

In certain embodiments, a polyamide of the invention has a binding affinity $K_a$ for an ARE, GRE and/or ERE that is greater than $10^8 \text{ M}^{-1}$, or preferably greater than $2\times10^8 \text{ M}^{-1}$, or preferably greater than $5\times10^8 \text{ M}^{-1}$, or preferably greater than $10^9 \text{ M}^{-1}$, or preferably greater than $2\times10^9 \text{ M}^{-1}$, or preferably greater than $5\times10^9 \text{ M}^{-1}$, or preferably greater than $10^{10} \text{ M}^{-1}$, or preferably greater than $2\times10^{10} \text{ M}^{-1}$, or preferably greater than $5\times10^{10} \text{ M}^{-1}$, or preferably greater than $10^{11} \text{ M}^{-1}$. The reduction in affinity of a polyamide of the invention to an ARE, GRE and/or ERE with a mismatch of one, two or three nucleotides, when compared to ARE, GRE and/or ERE without a mismatch, in certain embodiments, is at least 3 fold, at least 5 fold, at least 10 fold, at least 20 fold, at least 50 fold, or at least 100 fold, or more. The affinity of a polynucleotide of the invention to DNA (or another molecule) can be determined by any method known in the art and as discussed herein.

A polyamide of the invention, in certain embodiments, can be examined to determine its affinity for its target DNA sequence and at mismatched and random sites, if desired. The affinity can be determined using DNase footprint analysis, as discussed herein. A polyamide of the invention, in certain embodiments, can also be examined to determine its ability to modulate gene expression, for example, by using an ARE, GRE and/or ERE involved in regulating the expression of a gene. For example, a polyamide may be administered to cells in culture at varying concentrations (e.g., at 0.2 μM, 0.5 μM, 1 μM, 2 μM, 5 μM, 10 μM, and 25 μM) and the expression of a gene that depends on an ARE, GRE and/or ERE may be determined by measuring levels of mRNA (messenger RNA) compared to mRNA levels in the absence of the polyamide. The analysis may be carried out, for example, as discussed in the examples below. An analysis of a polyamide's ability to modulate gene expression may be carried out in different cell types, for example, as described in Edelson et al., 2004, Nucleic Acids Res. 32:2802-2818. Other methods to analyze a polyamide's ability to modulate gene expression include the use of luciferase, protein quantitation, observing morphological and/or phenotypic changes, which are known to those of skill in the art.

Methods for the analysis of polyamides' ability to bind DNA and to modulate gene expression are further discussed, for example, in U.S. Pat. Nos. 7,087,378; 7,049,061; 6,958, 240; 6,673,940; 6,660,255; 6,635,417; 6,559,125; 6,555,692; 6,545,162; 6,506,906; 6,472,537; 6,303,312; 6,143,901; 6,090,947; 5,998,140, and in U.S. Patent Applications Nos. 20060270727; 20060025429; 20060019972; 20060014163; 20050026174, and in references discussed in any one of these patents and patent applications. All of these patents and patent applications, and references discussed therein, are incorporated herein by reference in their entirety.

5.3 Polyamides of the Current Invention as Research Tools

A polyamide of the invention, in certain embodiments, may be used as a research tool. For example, a polyamide of the invention may be used to modulate the expression of genes involved in a disease in cell culture or in an animal, for example, by down-regulating a gene so that the cells or the animal exhibits one or more traits of the disease. Following such modulation, a drug candidate may be tested in the cell culture and/or the animal to determine if the drug candidate is capable of compensating for the effects of gene modulation.

In certain other embodiments, a polyamide may be used to test the effectiveness of analytical techniques in a cell and/or an animal, for example by modulating gene expression and by testing the technique's ability to detect the effects thereof.

5.4 Therapeutic Applications of Polyamides of the Current Invention

A polyamide of the current invention, in certain embodiments, may be used in the treatment or prevention of a disease or condition in humans, animals and/or plants. It is contemplated that these compounds may be used independently or in conjunction with inactive excipients or active ingredients. As used herein, the term "agent" refers to compounds of the invention or compositions thereof comprising active and/or inactive ingredients.

In certain embodiments, polyamides of the invention may be used to modulate the expression of a gene, the expression of which depends at least in part on an ARE, GRE and/or ERE. In certain embodiments, polyamides of the invention may be used to modulate a gene with one, two, three, four, five, six or more AREs, GREs and/or EREs in a regulatory sequence of the gene, for example, in a promoter of the gene or an enhancer of the gene. A regulatory sequence of a gene may be within the gene (for example, in an intron, or in a 5 prime or 3 prime untranslated region), 5 prime (upstream) of the gene (for example, as part of a promoter that is located upstream of, and adjacent to or close to, the transcription initiation site), or 3 prime (downstream) of the gene (for example, 3 prime of the transcription termination site).

In certain embodiments, polyamides of the invention may be used to modulate the expression the PSA gene (prostate specific antigen), the klk2 gene, the tmprss2 gene, the DHCR24 gene, the LOC89944 gene, the NNMT gene, the GSTM1 gene, the UNC13 gene, the BICD1 gene, the ENTPD5 gene, the PFKFB3 gene, the ARL7 gene, the FLJ2378 gene, the ATP2C1 gene, the C20orf167 gene, the SLC37A1 gene, the DOK4 gene, the FLJ14249 gene, the FLJ38482 gene, the TMEPAI gene, the KLK3 gene, the ASAH1 gene, the UNC5H2 gene, any gene listed in Table 3 (see below), any gene listed in Table 4 (see below).

In certain embodiments, polyamides of the invention may be used to modulate the expression of a gene with an ARE, for example, a gene listed in Massie C E et al., New androgen receptor genomic targets show an interaction with the ETS1 transcription factor. EMBO Rep. 2007 September; 8(9):871-8; Bolton E C et al., Cell- and gene-specific regulation of primary target genes by the androgen receptor. Genes Dev. 2007 Aug. 15; 21(16):2005-17, which are incorporated herein by reference for any purpose. In certain embodiments, polyamides of the invention may be used to modulate the expression of a gene with an ERE, for example, a gene listed in Carroll J S et al., Genome-wide analysis of estrogen receptor binding sites. Nat Genet. 2006 November; 38(11):1289-97, which is incorporated herein by reference for any purpose.

In certain embodiments, polyamides of the invention may be used to modulate the expression of a gene that is expressed in a tissue or organ, but that is not expressed in other tissues or organs, or that is expressed in other tissues at significantly lesser levels (for example, less than 20 percent, or less than 10 percent, or less than 5 percent), in other words a tissue-specific gene. A tissue-specific gene may be expressed in the prostate (prostate-specific gene).

In certain embodiments, polyamides of the invention may be used to treat a disease. "Treating" as used herein refers to alleviation of at least one symptom associated with a disease (for example, cancer), or halt of further progression or worsening of such disease, or prevention or prophylaxis of such disease. In certain embodiments, polyamides of the invention may be used to treat cancer, prostate cancer, a prostate-specific disease, hair-loss or alopecia, male-pattern hair loss, breast cancer, inflammatory diseases or diseases involving inflammation, diseases or conditions affecting fertility, ovarian cancer, colorectal cancer, endometrial cancer, osteoporosis, neurodegenerative diseases, cardiovascular disease, insulin resistance, lupus erythematosus, endometriosis, obesity, metabolic diseases, or any other disease involving the expression of a gene that is regulated by an ARE, GRE and/or ERE.

A polyamide of the invention, in certain embodiments, may be delivered to a patient in any way known in the art. The particular delivery mode selected will depend upon the polyamide selected, the condition being treated, the severity of the condition, whether the treatment is therapeutic or prophylactic, and the dosage required for efficacy. Therapeutic delivery of polyamides of the invention may be practiced using any mode of administration that is medically acceptable, meaning any mode that produces effective levels of the active compounds without causing clinically unacceptable adverse effects. Any dosage forms containing effective amounts are well within the bounds of routine experimentation and therefore, well within the scope of the instant invention. A therapeutically effective dose may vary depending upon the route of administration and dosage form. The administration may, for example, be oral, intraperitoneal, intra-cavity such as rectal or vaginal, transdermal, topical, nasal, inhalation, mucosal, interdermal, or parenteral routes. The term "parenteral" includes subcutaneous, intravenous, intramuscular, or infusion. Intravenous or intramuscular routes may not be particularly suitable for long term therapy and prophylaxis. In certain embodiments, however, it may be appropriate to administer the agent in a continuous infusion every several days, or once a week, or every several weeks, or once a month. Intravenous or intramuscular routes may be preferred in emergency situations. Oral administration may be used for prophylactic treatment because of the convenience to the patient as well as the dosing schedule. Likewise, sustained release devices as described herein may be useful in certain embodiments for prophylactic or post surgery treatment, for example.

Direct administration of a polyamide of the present invention to a designated site may be preferred for some methods provided herein. For example, treatment with a polyamide via topical administration in and around affected areas may be performed. In still other embodiments, a polyamide may be delivered by injection directly into the tissue with, for example, a biopsy needle and syringe.

Systemic administration may be preferred in some instances such as, for example, if the subject is known to have or is suspected of having metastases. In this embodiment, all tumor sites, whether primary or secondary, may receive the polyamide. Systemic delivery may be accomplished through for example, oral or parenteral administration. Inhalation may be used in either systemic or local delivery, as described below.

A polyamide of the invention, in certain embodiments, is administered in therapeutically effective amounts. A therapeutically effective amount is an amount sufficient to delay the onset of, inhibit the progression of, or halt altogether the particular condition being treated. The effective amount will vary with the particular condition being treated, the age and physical condition of the subject being treated, the severity of the condition, the duration of the treatment, the nature of the concurrent or combination therapy (if any), the specific route of administration and like factors within the knowledge and expertise of the health practitioner. A therapeutically effective dose results in amelioration of at least one undesirable symptom. It is preferred generally that a maximum dose be used, that is, the highest safe dose according to sound medical judgment. Dosing amounts, dosing schedules, routes of administration and the like can be selected so as to affect bio-activity of the present compounds. Such determinations are routine and well known to one of ordinary skill in the art.

A therapeutically effective amount typically varies from 0.01 mg/kg (weight of polyamide over weight of patient) to about 1000 mg/kg, preferably from about 0.1 mg/kg to about 200 mg/kg, and most preferably from about 0.2 mg/kg to about 20 mg/kg, in one or more dose administrations daily, for one or more days. In some embodiments, a polyamide is administered for more than 7 days, more than 10 days, more than 14 days, or more than 20 days. In still other embodiments, a polyamide is administered over a period of weeks, or months. In still other embodiments, a polyamide is delivered on alternate days. For example, the polyamide is delivered every two days, or every three days, or every four days, or every five days, or every six days, or every week, or every month.

A polyamide of the invention, in certain embodiments, is administered in prophylactically effective amounts. In these embodiments, a polyamide is administered in an amount effective to prevent the development of an abnormal or undesirable condition or disease. For example, in connection with methods directed towards treating subjects having a condition characterized by abnormal mammalian cell proliferation, an effective amount to inhibit proliferation would be an amount sufficient to reduce or halt altogether the abnormal mammalian cell proliferation so as to slow or halt the development of or the progression of a cell mass such as, for example, a tumor. As used in the embodiments, "inhibit" embraces all of the foregoing.

For example, in connection with methods directed to inhibition of mammalian cell proliferation, a therapeutically effective amount will be an amount necessary to extend the dormancy of micrometastases or to stabilize any residual primary tumor cells following surgical or drug therapy.

Compositions presented herein may include DNA-binding polymers of the invention in combination with any standard physiologically and/or pharmaceutically acceptable carrier known in the art. The term "pharmaceutically acceptable carrier" as used herein means one or more compatible solid or liquid fillers, diluents or encapsulating substances which are suitable for administration to a subject. The term "carrier" denotes an organic or inorganic ingredient, natural or synthetic, which with the DNA-binding polymer is combined to facilitate delivery of the composition. The components of the pharmaceutical compositions also are capable of being co-mingled with the molecules of the present invention, and with each other, in a manner so as to not substantially impair the desired pharmaceutical efficacy. Pharmaceutically acceptable further means a non-toxic material that is compatible with a biological system such as a cell, cell culture, tissue, or organism. The particular carrier may vary depending on the route of therapeutic delivery.

Pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsules, syrup, suppositories, injections, emulsions, elixirs, suspensions or solutions. The instant compositions can be formulated for various routes of administration, for example, by oral administration, by intranasal administration, by transmucosal administration, by rectal administration, or subcutaneous administration as well as intrathecal, intravenous, intramuscular, intraperitoneal, intranasal, intraocular or intraventricular injection. The compound or DNA-binding polymers of the instant invention can also be administered in a local rather than a systemic fashion, such as injection as a sustained release formulation. The following dosage forms are given by way of example and should not be construed as limiting the instant invention.

Compositions suitable for parenteral administration conveniently comprise a sterile aqueous preparation of the agent, which is preferably isotonic with the blood of the recipient. This aqueous preparation may be formulated according to known methods using suitable dispersing or wetting compounds and suspending compounds. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found, for example, in "Remington's Pharmaceutical Sciences" Mack Publishing Co., New Jersey (1991), which is incorporated herein by reference.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating compounds, and inert gases and the like. The pharmaceutical compositions may conveniently be presented in unit dosage form and may be prepared by any of the methods well-known in the art of pharmacy.

Compositions suitable for oral administration may be presented as discrete units, such as capsules, tablets, lozenges, each containing a predetermined amount of the agent. Other compositions include suspensions in aqueous liquids or non-aqueous liquids such as a syrup, elixir or an emulsion. Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

Compositions may comprise a biocompatible microparticle or implant that is suitable for implantation. Biocompatible and biodegradable polymeric matrix materials may also be added. The polymeric matrix may be used to achieve sustained release of the agent in a subject. DNA-binding polymers of the invention may be encapsulated or dispersed within a biocompatible and biodegradable polymeric matrix. The polymeric matrix can be in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular or pulmonary surface. The matrix composition also can be selected not to degrade, but rather, to release by diffusion over an extended period of time.

Both non-biodegradable and biodegradable polymeric matrices can be used to deliver the agents of the invention to the subject. Such polymers may be natural or synthetic polymers. Synthetic polymers are preferred. The polymer is selected based on the period of time over which release is desired, generally in the order of a few hours to a year or longer. The polymer optionally is in the form of a hydrogel that can absorb up to about 90% of its weight in water and further, optionally is cross-linked with multi-valent ions or other polymers.

Exemplary synthetic polymers which can be used include: polycarbonates, polyalkylenes, polyalkylene glycols, polyalkylene oxides, polyalkylene terpthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, polyethylene glycol), poly(ethylene oxide), poly(ethylene terephthalate), poly(vinyl alcohols), polyvinyl acetate, poly vinyl chloride, polystyrene and polyvinylpyrrolidone. Examples of non-biodegradable polymers include ethylene vinyl acetate, poly(meth)acrylic acid, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers may also be included in the present compositions. Examples of such bioadhesive polymers include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Compositions of the present invention may be formulated as timed release, delayed release, or sustained release delivery systems. Such systems can avoid the need for repeated administrations of the agent of the invention, increasing convenience to the subject and the physician. Many types of release delivery systems are available and known to those of ordinary skill in the art. They include the above-described polymeric systems, as well as polymer base systems such as poly(lactide-glycolide), polyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,675,189 and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be used in the treatment of chronic conditions, such as the suspected presence of dormant metastases. Long-term release, are used herein, means that the implant is constructed and arranged to deliver therapeutic levels of the active ingredient for at least 30 days, at least 60 days and more preferably for several months. Long-term sustained release implants are well-known to those of ordinary skill in the art and include some of the release systems described above.

For oral, buccal, and sublingual administration, powders, suspensions, granules, tablets, pills, capsules, gelcaps, and caplets are acceptable as solid dosage forms. These can be prepared, for example, by mixing one or more DNA-binding polymers of the instant invention, or pharmaceutically acceptable salts or tautomers thereof, with at least one additive or excipient such as a starch or other additive. Suitable additives or excipients are sucrose, lactose, cellulose, sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents, or perfuming agents. Additionally, dyestuffs or pigments may be added for identification. Tablets and pills may be further treated with suitable coating materials known in the art.

As noted above, suspensions may include oils. Such oils include, but are not limited to, peanut oil, sesame oil, cottonseed oil, corn oil and olive oil. Suspension preparations may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

For intranasal administration (e.g., to deliver compounds to the brain), or administration by inhalation (e.g., to deliver compounds through the lungs), the pharmaceutical formulations may be a solution, a spray, a dry powder, or aerosol containing any appropriate solvents and optionally other compounds such as, but not limited to, stabilizers, antimicrobial agents, antioxidants, pH modifiers, surfactants, bioavailability modifiers and combinations of these. Examples of intranasal formulations and methods of administration can be found in WO 01/41782, WO 00133813, WO 91/97947, U.S. Pat. Nos. 6,180,603, and 5,624,898. A propellant for an aerosol formulation may include compressed air, nitrogen, carbon dioxide, or a hydrocarbon based low boiling solvent. The compound or DNA-binding polymers of the instant invention are conveniently delivered in the form of an aerosol spray presentation from a nebulizer or the like.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or diluents include sterilized water, Ringer's solution, or an isotonic aqueous saline solution. For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers.

For rectal administration, the pharmaceutical formulations may be in the form of a suppository, an ointment, an enema, a tablet or a cream for release of compound in the intestines, sigmoid flexure and/or rectum. Rectal suppositories are prepared by mixing one or more DNA-binding polymers of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils may also be employed in the preparation of formulations of the soft gelatin type and suppositories. Water, saline, aqueous dextrose and related sugar solutions, and glycerols may be employed in the preparation of suspension formulations which may also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

Compositions of the present invention embrace pharmaceutically acceptable salts of DNA-binding polymers of the invention. Pharmaceutically acceptable salts include a salt with an inorganic base, organic base, inorganic acid, organic acid, or basic or acidic amino acid. As salts of inorganic bases, the invention includes, for example, salts of alkali metals (such as sodium or potassium) and alkaline earth metals (such as calcium and magnesium or aluminum, and ammonia). As salts of organic bases, the invention includes, for example, salts of trimethylamine, triethylamine, pyridine, picoline, ethanolamine, diethanolamine, triethanolamine. As salts of inorganic acids, the instant invention includes, for example, salts of hydrochloric acid, hydroboric acid, nitric acid, sulfuric acid, and phosphoric acid. As salts of organic acids, the instant invention includes, for example, salts of formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid.

The present invention is further illustrated by the following examples, which are not intended to be limiting in any way whatsoever.

EXAMPLES

Example 1

1.1 Abstract

Androgen receptor (AR) is essential for the growth and progression of prostate cancer in both hormone-sensitive and hormone-refractory disease. A DNA-binding polyamide that targets the consensus androgen response element binds the prostate-specific antigen (PSA) promoter androgen response element, inhibits androgen-induced expression of PSA and several other AR-regulated genes in cultured prostate cancer cells, and reduces AR occupancy at the PSA promoter and enhancer. Down-regulation of PSA by this polyamide was comparable to that produced by the synthetic antiandrogen bicalutamide (Casodex) at the same concentration. Genome-wide expression analysis reveals that a similar number of transcripts are affected by treatment with the polyamide and with bicalutamide. Direct inhibition of the AR-DNA interface by sequence-specific DNA binding small molecules could offer an alternative approach to antagonizing AR activity.

Abbreviations: AR, androgen receptor; ARE, androgen response element; PSA, prostate-specific antigen; DHT, dihydrotestosterone.

1.2 Introduction

The androgen receptor (AR) is a member of the ligand-activated nuclear receptor family of transcription factors (1). Ligand binding to AR initiates release from the cytoplasm, dimerization, binding to the androgen response elements (ARE) of target genes, and gene activation through interaction with coactivators and the general transcription machinery (2). Functional AREs, consensus sequence 5'-GGTA-CAnnnTGTTCT-3' (SEQ ID NO:1) (FIG. 7A) (3) can occur in proximal promoter sequences or in enhancers located up to several thousand base pairs upstream or downstream of the transcription start site.

The regulation of prostate-specific antigen (PSA) (KLK3) expression by AR has been extensively studied as a model for AR-mediated gene activation (4-7). Androgenic induction of PSA is mediated by AR binding to the proximal promoter ≈170 bp from the transcription start site and to several low-affinity AREs in an enhancer ≈4,000 bp upstream (4-6). AREs in both the promoter and enhancer are important for induction after androgen stimulation. AR occupies both the promoter and enhancer regions and recruits transcriptional coactivators including p160 and p300, TATA-binding protein, mediator, and RNA polymerase II to form the AR transcription complex (7, 8). Chromatin-capture assays suggest that the PSA enhancer is located near the promoter in this complex (8).

AR signaling regulates normal prostate development and contributes to the progression of prostate cancer (9). Surgical or drug therapies that act to limit circulating androgen levels or directly antagonize ligand binding to AR initially slow prostate cancer growth (10, 11). However, nearly all patients treated with antiandrogen therapies will eventually develop hormone-refractory disease (12). Dysregulation of AR activity, together with activation of the PTEN/AKT pathway, is thought to contribute to this transition (13). Up-regulation of AR mRNA was found to occur in all transitions from hormone-sensitive to hormone-refractory disease in a mouse tumor-xenograft model of prostate cancer (14). Additionally, a transgenic mouse with a mutated AR that inappropriately interacts with transcriptional coregulators developed metastatic neoplastic disease (15). Mutations in the AR ligand-binding domain can render antagonists such as bicalutamide or flutamide ineffective or, in some models of hormone-refractory disease, convert them to agonists (14, 16). Given that genotropic AR activity is thought to be necessary throughout prostate cancer progression, direct antagonism of AR-DNA binding could inhibit androgen receptor activity in hormone-refractory conditions where androgen antagonists that target the ligand-binding pocket are ineffective (9).

DNA-binding polyamides represent one approach to inhibiting protein-DNA interactions. Polyamides containing N-methylimidazole (Im) and N-methylpyrrole (Py) comprise a class of programmable DNA-binding ligands capable of binding to a broad repertoire of DNA sequences with affinities and specificities comparable to those of natural DNA-binding proteins (17, 18). Sequence specificity is programmed by side-by-side pairings of the heterocyclic amino acids in the minor groove of DNA: Im/Py distinguishes G•C from C•G; Py/Py binds both A-T and T-A (19, 20). Previously, a hairpin polyamide targeted to the hypoxia response element (HRE) inhibited hypoxia-induced expression of several HIF-1-regulated genes, including VEGF, in cultured cells (21, 22).

In this study, we have designed a cell-permeable polyamide to target the sequence 5'-WGWWCW-3', found in the consensus ARE, with the goal of disrupting AR-mediated gene expression (FIG. 7). We show that this polyamide binds the ARE found in the PSA promoter, inhibits expression of PSA as well as ≈35% of the transcripts that were induced by dihydrotestosterone (DHT) in cultured prostate cancer cells, and reduces AR occupancy at the PSA promoter and enhancer. Down-regulation of PSA by this polyamide was comparable to the effects of the synthetic antiandrogen bicalutamide (Casodex) at the same concentration. A control polyamide targeted to a different sequence had less effect.

1.3 Materials and Methods

1.3.1 Synthesis of Polyamides

Polyamides 1 (structure 39, FIG. 4) and 2 were synthesized by solid-phase methods on Kaiser oxime resin (Nova Biochem, Darmstadt, Germany) according to established protocols (43). Polyamides were cleaved from resin with 3,3'-diamino-N-methyl-dipropylamine and purified by reverse-phase HPLC. Isophthalic acid was activated with PyBOP (Nova Biochem) and conjugated to the polyamides as described (22). Purities and identities of the polyamides were assessed by HPLC, UV-visible spectroscopy, and MALDI-TOF MS.

1.3.2 Determination of DNA-Binding Affinity and Sequence Specificity

Plasmid pAR-PSA was constructed by inserting a 70-bp sequence from the PSA promoter containing the ARE into pUC19 plasmid. Quantitative DNase I footprint titration experiments were used to measure the binding affinities of 1 and 2 on a 5'-$^{32}$P-labeled fragment of pAR-PSA that contains the PSA promoter ARE. Detailed experimental protocols are reported elsewhere (44).

1.3.3 Electrophoretic Mobility Shift Assay

The oligonucleotide 5'-GCATTGC AGAACAGCAAGTGCTAGCTCTCCC-3' (SEQ ID NO:14) containing the PSA promoter ARE (underlined) was end-labeled with $^{32}$P and annealed to its complement. Polyamides 1 and 2 were incubated with the duplex for 3 h in previously optimized buffer conditions (45). Nuclear extract from DHT-treated LNCaP cells (Genetex, San Antonio, Tex.) was then added for an additional 45 min. Complexes were run on a 5% polyacrylamide gel and visualized on a phosphorimager.

1.3.4 Measurement of Androgen-Induced PSA mRNA and Protein

LNCaP cells (ATCC) were plated in 24-well plates at a density of 40-50×10$^3$ cells per well (80-100×10$^3$ cells per ml) in RPMI medium 1640 (ATCC) supplemented with 10% FBS (Irvine Scientific, Santa Ana, Calif.). After 72 h, the medium was replaced with RPMI medium 1640 containing 10% charcoal stripped FBS with or without polyamides at the designated concentrations. Cells were grown for an additional 48 h and then treated with 1 nM DHT for 16 h. When appropriate, bicalutamide was added 2 h before DHT stimulation. Isolation of RNA and cDNA synthesis was performed as described (21). Quantitative real-time RT-PCR was performed with SYBR Green PCR Master Mix (Applied Biosystems, Foster City, Calif.) on an ABI 7300 instrument. PSA mRNA was measured relative to P-glucuronidase as an endogenous control. Primer sequences are available upon request. Cell-culture supernatants were collected for an ELISA (R & D Systems, Minneapolis, Minn.) to measure PSA protein according to the manufacturer's protocol.

1.3.5 Chromatin Immunoprecipitation

LNCaP cells were plated in 15-cm diameter plates at a density of 2×10$^6$ cells per plate. Media, polyamide treatment, time course, and DHT stimulation were the same as described above. After the 16-h DHT treatment, cells were treated with 1% formaldehyde for 10 min. Chromatin was isolated and sheared. Antibodies to AR (AR-20, Santa Cruz Biotechnology, Santa Cruz, Calif.) were used to immunoprecipitate AR-bound DNA fragments. Crosslinks were reversed, and PCRs using primers targeted to the regions of interest were used to assess enrichment of bound fragments as compared with mock-precipitated (no antibody) controls. PCRs were monitored with SYBR Green PCR Master Mix (Applied Biosystems) on an ABI 7300 instrument. Primer sequences and a more detailed experimental protocol are available upon request.

1.3.6 Analysis of Gene Expression with Oligonucleotide Microarrays

LNCaP cells were plated in 12-well plates at a density of 80-1000×10$^3$ cells per well. Media, polyamide treatments, and time courses were the same as described above. Bicalutamide was added 2 h before DHT stimulation. RNA was isolated as described in ref. 21. From this point, experiments were carried out at the Millard and Muriel Jacobs Gene Expression Facility at the California Institute of Technology.

Labeled mRNA was hybridized to Affymetrixhigh-density Human Genome U133 Plus 2.0 arrays according to established protocols. Gene expression was analyzed by using Resolver (Rosetta Biosoftware, Seattle, Wash.). Data were uploaded to the Gene Expression Omnibus repository (accession no. GSE7708).

1.4 Results

1.4.1 Binding Affinities of Polyamides to the ARE of the PSA Promoter

The proximal PSA promoter contains the ARE 5'-AGAA-CAGCAAGTGCT-3' (SEQ ID NO:15) (FIG. 8A). The DNA binding of polyamides 1 and 2 on this sequence was measured by quantitative DNase I footprint titrations using a 5'-$^{32}$P-labeled PCR fragment of pAR-PSA, which contains the PSA ARE. Polyamide 1 has a $K_a=8.3\pm1.7\times10^9$ $M^{-1}$ for the ARE consensus half-site 5'-AGAACA-3' (FIG. 8B). Binding of polyamide 2, which targets the sequence 5'-WGWCGW-3', to the ARE is not measurable by these methods ($K_a<1\times10^7$) (FIG. 8C). Minimal binding of polyamide 1 is observed at the other half-site of the ARE: 5'-AGTGCT-3', which is formally a single base pair mismatch site for 1. However, 1 is observed to bind the sequence 5'-AGATCA-3' ≈12 bp 5' to the ARE, which is an expected binding site for this molecule.

1.4.2 Electrophoretic Mobility Shift Assay

The effects of polyamides 1 and 2 on the binding of factors present in the nuclear extract isolated from DHT-stimulated LNCaP cells to the ARE site in the PSA promoter was measured by an electrophoretic mobility shift assay (FIG. 8D). Polyamide 1 inhibits binding to the 5'-$^{32}$P-labeled duplex at concentrations as low as 10 nM. Polyamide 2 has minimal effect at the same concentrations.

1.4.3 Inhibition of Androgen-Inducted PSA Expression

Induction of PSA mRNA by DHT in the presence of polyamides 1 and 2 and bicalutamide in LNCaP cells was measured by quantitative real-time RT-PCR. Bicalutamide and polyamide 1 inhibit the expression of DHT-induced PSA in a dose-dependent manner up to p70% at 10 μM, as measured in this assay (FIG. 9A). Polyamide 2 has a more modest effect. Secretion of PSA protein after DHT stimulation of LNCaP cells in the presence of 1 and 2 was measured by ELISA (FIG. 9B). Supernatant concentrations of PSA protein are reduced in cells pretreated with 1 as compared with 2 or an untreated control. AR occupancy at the PSA promoter and enhancer was assessed by chromatin immunoprecipitation (FIG. 9C). Chromatin immunoprecipitation assays with anti-AR antibody treatment indicate decreased occupancy of AR at the PSA promoter and enhancer in the presence of 10 μM 1. Polyamide 2 has minimal effect. Polyamides 1 and 2 display no obvious detrimental effects on cell growth over the course of the experiment. AR mRNA is minimally affected by 1 (FIG. 11).

1.4.4 Inhibition of Androgen-Induced FKBP5 Expression

Recent studies have identified FKBP5 as one of the most strongly induced genes in androgen-stimulated prostate cancer cells (23). Two functional AREs with the sequences 5'-AGCACATCGAGTTCA-3' (SEQ ID NO:16) and 5'-AGAACAGGGTGTTCT-3' (SEQ ID NO:17) have been mapped to an enhancer within the fifth intron (24). Polyamide 1 inhibits DHT-induced expression of FKBP5 by ≈60% (FIG. 9D). Bicalutamide was more potent, however, inhibiting expression by almost 95%. Polyamide 2 has minimal effect on FKBP5 expression. Chromatin immunoprecipitation assays indicate decreased occupancy of AR at the FKBP5 intronic enhancer in the presence of 10 μM 1 (FIG. 9E), whereas polyamide 2 has no measurable effect.

1.4.5 Global Effects on Androgen-Induced Gene Expression

Figure 10A:
FIG. 10: Global effects on transcripts interrogated using Affymetrix high-density Human Genome U133 Plus 2.0 Arrays. (A) Divisive clustering of all measured transcripts under the four specified conditions: no treatment control; B, bicalutamide (10 μM); 1 (10 μM); 2 (10 μM). Clustering was based on an error weighted Pearson correlation of intensity ratios for each treatment as compared to DHT-induced controls. (B) Ven diagrams representing transcripts down- and up-regulated (|fold-change|μ2.0, p μ10.01) by bicalutamide and 1. Numbers inside the intersections represent transcripts affected by both treatments. Of the 122 transcripts down-regulated by both bicalutamide and 1, 117 are also observed to be induced by DHT at the same thresholds. (C) Agglomerative clustering of expression changes of the 199 transcripts induced or repressed 4-fold (p≤0.01) or more by 1 nM DHT under the designated treatment conditions. Of the DHT-induced set, 70 were inhibited by polyamide 1, 20 were inhibited by 2, and 186 by bicalutamide (|fold-change|≥2.0, p≤0.01). Clustering parameters were the same as in (A). Treatments reported are an error-weighted average from three experiments, except the non-induced control which was an average from two experiments.

Global effects of polyamides 1 and 2 and bicalutamide on gene expression in DHT-stimulated LNCaP cells were monitored with Affymetrix (Santa Clara, Calif.) high-density Human Genome U133 Plus 2.0 arrays, which interrogate >50,000 transcripts. As compared with DHT-induced controls, polyamide 1 (10 μM) affected the expression of 1,053 transcripts by at least 2-fold (P≤0.01) (Table 1), which represents less than 2% of interrogated transcripts. Of this total, 706 were down-regulated. At the same threshold, bicalutamide (10 μM) affected the expression of 1,213 transcripts, with 602 of these being down-regulated. Polyamide 2 (10 μM) affected the expression of 379 transcripts, which represents <1% of interrogated transcripts. A divisive clustering analysis over all interrogated transcripts suggests that the expression profiles of cells treated with bicalutamide, 1, and 2 are largely distinct (FIG. 10A). Analysis of transcripts affected by both bicalutamide and 1 shows that 122 and 90 transcripts are commonly down- and up-regulated, respectively, at least 2-fold (P≤0.01) (FIG. 10B). Of the 122 transcripts down-regulated by both bicalutamide and 1, 117 are also observed to be induced by DHT at the same thresholds. Of the 90 up-regulated transcripts, 59 are observed to be repressed by DHT.

TABLE 1

| Number of transcripts affected relative to DHT-induced controls. (p ≤ 0.01) | | | | |
|---|---|---|---|---|
| | Treatment | | | |
| | — | B | 1 | 2 |
| | DHT | | | |
| | − | + | + | + |
| up-regulated (fold change ≥2.0) | 486 | 611 | 347 | 95 |
| down-regulated (fold change ≤−2.0) | 782 | 602 | 706 | 284 |
| up-regulatd (fold change ≥4.0) | 88 | 96 | 42 | 11 |
| down-regulated (fold change ≤−4.0) | 199 | 133 | 126 | 32 |

Figure 10C:

The response of cultured prostate cancer cells to androgen has been extensively studied (23, 25). We find that DHT induced the expression of a set of 199 transcripts by at least 4-fold (P≤0.01). Of this set, 70 were also inhibited by polyamide 1 by at least 2-fold (P≤0.01). For comparison, polyamide 2 inhibited 20, and bicalutamide inhibited 186, of the 199 DHT-induced transcripts with the same thresholds (FIG. 10C). DHT repressed the expression of a set of 88 transcripts by at least 4-fold (P≤0.01). Of this set, eight were also derepressed, as compared with DHT-treated controls, by polyamide 1 by at least 2-fold (P<0.01). For comparison, polyamide 2 derepressed 3, and bicalutamide derepressed 87, of the 88 transcripts repressed by DHT with the same thresholds (FIG. 10C). A complete list of the DHT-induced transcripts and those affected by 1 is provided in Tables 3 and 4. It is not known what proportions of these genes are direct targets of AR. Table 2 displays the effects of each treatment on the expression of a few selected genes that were observed to be induced by DHT and are known to be targets of AR (26, 27). Effects on the expression of KLK2 and TMPRSS2 were verified by quantitative real-time RT-PCR (FIG. 11).

TABLE 2

Fold-changes of selected AR-target genes relative to DHT-induced controls.

| Gene | — | B | 1 | 2 |
|---|---|---|---|---|
| | | DHT | | |
| | − | + | + | + |
| KLK2 | −23.0 | −14.7 | −2.4 | −1.1 |
| KLK3 (PSA) | −6.1 | −3.2 | −3.3 | −1.4 |
| TMPRSS2 | −6.2 | −4.1 | −2.3 | −1.4 |
| FKBP5 | −42.9 | −36.4 | −3.1 | 1.5 |

TABLE 3

Transcripts induced at least 4-fold (p ≤ 0.01) by dihydrotestosterone. Fold change is expressed as DHT non-induced compared to DHT-induced.

| Name | Accession # | Fold Change | P-value |
|---|---|---|---|
| FLJ23153 | AA650281 | −100.0 | 0.000 |
| ORM1 | NM_000607 | −95.9 | 0.000 |
| ORM1 | NM_000607 | −43.4 | 0.000 |
| FKBP5 | NM_004117 | −42.9 | 0.000 |
| FLJ39502 | NM_173648.1 | −35.5 | 0.000 |
| HPGD | AL574184 | −27.2 | 0.000 |
| MAK | NM_005906 | −24.0 | 0.000 |
| KLK2 | AF188747 | −23.0 | 0.000 |
| HPGD | J05594 | −21.3 | 0.000 |
| DKFZp761P0423 | BF739767 | −21.0 | 0.000 |
| MAF | NM_005360 | −19.4 | 0.000 |
| ORM2 | NM_000608 | −18.4 | 0.000 |
| FLJ11937 | NM_022765 | −17.2 | 0.000 |
| FKBP5 | W86302 | −17.2 | 0.000 |
| FLJ11264 | NM_018371 | −15.4 | 0.000 |
| AKAP12 | AB003476 | −15.4 | 0.000 |
| WBSCR5 | AF257135 | −14.7 | 0.000 |
| SLC41A1 | AW439816 | −14.6 | 0.000 |
| SLC15A2 | BF223679 | −13.9 | 0.000 |
| PIK3AP1 | AW575754 | −13.6 | 0.000 |
| FKBP5 | AI753747 | −13.6 | 0.000 |
| SLUG | AI572079 | −13.4 | 0.000 |
| SLC26A3 | NM_000111 | −13.1 | 0.000 |
| KLK2 | BC005196 | −13.0 | 0.000 |
| SLC2A3 | NM_006931 | −13.0 | 0.000 |
| KLK2 | AA595465 | −12.7 | 0.000 |
| BM040 | NM_018456 | −12.7 | 0.000 |
| SGK | NM_005627 | −12.7 | 0.000 |
| 230577_at | AW014022 | −12.4 | 0.000 |
| 242391_at | AW052176 | −11.8 | 0.000 |
| HPGD | NM_000860 | −11.4 | 0.000 |
| CEP3 | AI754416 | −11.3 | 0.000 |
| MAF | AF055376 | −10.9 | 0.000 |
| KIAA0056 | AI796581 | −10.2 | 0.000 |
| SPOCK | AF231124 | −10.1 | 0.000 |
| MYBPC1 | BF593509 | −10.0 | 0.000 |
| EMP1 | NM_001423 | −9.8 | 0.000 |
| TRG@ | M27331 | −9.8 | 0.000 |
| GNMT | AF101477 | −9.6 | 0.000 |
| HSY11339 | Y11339 | −9.5 | 0.000 |
| MAF | BE674528 | −9.4 | 0.000 |
| KIAA1145 | BG177562 | −9.4 | 0.000 |
| 244650_at | AA581439 | −9.2 | 0.000 |
| TRG@ | M16768 | −9.1 | 0.000 |
| F5 | NM_000130 | −9.1 | 0.000 |
| HPGD | U63296 | −9.0 | 0.000 |
| TRGC2 | M13231 | −8.9 | 0.000 |
| IGF1R | H05812 | −8.8 | 0.001 |
| NAT3 | NM_018018 | −8.6 | 0.000 |
| PNLIP | NM_000936 | −8.5 | 0.000 |
| PLEC1 | NM_000445 | −8.5 | 0.003 |
| KIAA0869 | AK001727 | −8.5 | 0.000 |
| MGC18216 | AL044092 | −8.4 | 0.000 |
| LIFR | AW592684 | −8.3 | 0.000 |
| NDRG1 | NM_006096 | −8.2 | 0.000 |
| FAM105A | AF052146 | −8.0 | 0.000 |
| LIFR | NM_002310 | −7.8 | 0.000 |
| ERN1 | AW194689 | −7.6 | 0.000 |
| FLJ11127 | NM_019018 | −7.5 | 0.000 |
| MOGAT2 | AK000245 | −7.4 | 0.000 |
| CEP3 | AI801777 | −7.2 | 0.000 |
| TMCC3 | N51717 | −7.1 | 0.000 |
| DKFZP434B0335 | BF513674 | −7.1 | 0.000 |
| LIFR | AI680541 | −7.0 | 0.000 |
| LAMA1 | AI990816 | −6.9 | 0.000 |
| 228559_at | BF111626 | −6.9 | 0.000 |
| BCAP29 | N57499 | −6.9 | 0.000 |
| NNT | U40490 | −6.9 | 0.000 |
| PTPRN2 | NM_002847 | −6.8 | 0.000 |
| CTNNA2 | NM_004389 | −6.8 | 0.000 |
| LRRFIP2 | AW137053 | −6.8 | 0.000 |
| FLJ11278 | NM_018378 | −6.7 | 0.000 |
| AFF3 | AW085505 | −6.7 | 0.000 |
| MGC13102 | BC005094 | −6.7 | 0.000 |
| PDEF | AI435670 | −6.6 | 0.000 |
| TRG@ | M30894 | −6.6 | 0.000 |
| CECR6 | AF307451 | −6.6 | 0.000 |
| TMEPAI | AL035541 | −6.6 | 0.000 |
| FLJ10055 | NM_017983 | −6.5 | 0.000 |
| LOC401623 | AI743452 | −6.5 | 0.000 |
| SLC2A3 | AI631159 | −6.5 | 0.001 |
| 235445_at | BF965166 | −6.4 | 0.000 |
| KIAA1330 | AB037751 | −6.4 | 0.001 |
| PCDH1 | NM_002587 | −6.4 | 0.000 |
| STATI2 | NM_003877 | −6.3 | 0.000 |
| TMPRSS2 | AI660243 | −6.2 | 0.000 |
| FER1L3 | NM_013451 | −6.2 | 0.000 |
| PRKCA | AI471375 | −6.1 | 0.000 |
| KLK3 | U17040 | −6.1 | 0.000 |
| SMPD2 | NM_003080 | −6.1 | 0.009 |
| MPHOSPH9 | X98258 | −6.0 | 0.000 |
| TBX15 | AI039005 | −6.0 | 0.000 |
| IGF1R | AI830698 | −5.9 | 0.000 |
| ELL2 | NM_012081 | −5.9 | 0.000 |
| TRPM8 | AI272941 | −5.9 | 0.000 |
| DSC1 | NM_004948 | −5.9 | 0.000 |
| CRIP2 | U36190 | −5.8 | 0.000 |
| TMEPAI | NM_020182 | −5.8 | 0.000 |
| FLJ23563 | AW138767 | −5.8 | 0.000 |
| KIAA1001 | AW052084 | −5.7 | 0.000 |
| BM039 | AK023669 | −5.7 | 0.000 |
| STATI2 | AB004903 | −5.7 | 0.000 |
| TMEPAI | AL035541 | −5.6 | 0.000 |
| KLK3 | NM_001648 | −5.6 | 0.000 |
| POV1 | NM_003627 | −5.5 | 0.000 |
| CNKSR2 | AI670947 | −5.5 | 0.000 |
| STK17B | N51102 | −5.5 | 0.000 |
| 232397_at | R14890 | −5.5 | 0.000 |
| ATRNL1 | BC035157.1 | −5.5 | 0.001 |
| HAK | AI741514 | −5.4 | 0.003 |
| ANKH | NM_019847 | −5.4 | 0.000 |
| LOC144481 | AK054607 | −5.4 | 0.000 |
| FER1L3 | AF207990 | −5.3 | 0.000 |
| ANK1 | NM_020479 | −5.3 | 0.001 |
| FLJ23153 | NM_024636 | −5.2 | 0.000 |
| PER1 | NM_002616 | −5.2 | 0.000 |
| 230782_at | AV699883 | −5.2 | 0.000 |
| ALAS2 | Z83821 | −5.1 | 0.000 |
| FLJ20624 | NM_017906 | −5.1 | 0.000 |
| TMPRSS2 | AF270487 | −5.1 | 0.000 |
| RAB3B | BC005035 | −5.0 | 0.000 |
| dJ646B12.1, dJ646B12.2 | AL096776 | −5.0 | 0.000 |
| 238975_at | AI671390 | −5.0 | 0.006 |
| PPFIBP2 | AI692180 | −4.9 | 0.000 |
| MAP3K10 | NM_002446 | −4.9 | 0.002 |
| LIFR | AA701657 | −4.9 | 0.000 |

TABLE 3-continued

Transcripts induced at least 4-fold (p ≤ 0.01) by dihydrotestosterone. Fold change is expressed as DHT non-induced compared to DHT-induced.

| Name | Accession # | Fold Change | P-value |
|---|---|---|---|
| PHLDB2 | AK025444 | −4.9 | 0.000 |
| KRT19 | NM_002276 | −4.9 | 0.000 |
| MAF | BF508646 | −4.9 | 0.001 |
| C1orf21 | NM_030806 | −4.8 | 0.000 |
| KRT8 | AL024458 | −4.8 | 0.000 |
| MGC4827 | NM_024114 | −4.8 | 0.000 |
| PTGER4 | AA897516 | −4.8 | 0.000 |
| 230710_at | W05495 | −4.7 | 0.000 |
| 1556185_a_at | BC035072.1 | −4.7 | 0.000 |
| DKFZP434B044 | AL136861 | −4.7 | 0.000 |
| TBC1D1 | BC028196.1 | −4.7 | 0.000 |
| ALDH4A1 | NM_003748 | −4.7 | 0.000 |
| DGCR14 | AL137713 | −4.7 | 0.003 |
| CSRP2 | NM_001321 | −4.7 | 0.000 |
| KIAA0194 | D83778 | −4.6 | 0.000 |
| FLJ11200 | AA886870 | −4.6 | 0.000 |
| GG2-1 | BC005352 | −4.6 | 0.000 |
| GG2-1 | NM_014350 | −4.6 | 0.000 |
| TMPRSS2 | NM_005656 | −4.6 | 0.000 |
| ABCC1 | NM_004996 | −4.5 | 0.000 |
| C1orf21 | AI159874 | −4.5 | 0.000 |
| ABCC4 | NM_005845 | −4.5 | 0.000 |
| IGF1 | AI972496 | −4.5 | 0.000 |
| BMPR1B | D89675 | −4.5 | 0.004 |
| ADH1C | NM_000669 | −4.5 | 0.004 |
| SLC16A6, LOC440459 | AI873273 | −4.5 | 0.000 |
| RAB3B | AU156710 | −4.5 | 0.000 |
| PIG11 | NM_006034 | −4.5 | 0.002 |
| KIAA0575 | NM_014668 | −4.5 | 0.000 |
| 241950_at | BG034847 | −4.4 | 0.007 |
| LOC221981 | R33964 | −4.4 | 0.001 |
| KCNMA1 | AI129381 | −4.4 | 0.000 |
| CAMKK2 | AA181179 | −4.4 | 0.000 |
| SEC14L2 | NM_012429 | −4.4 | 0.000 |
| FZD5 | NM_003468 | −4.4 | 0.010 |
| OACT2 | AI761250 | −4.4 | 0.000 |
| LIG1 | AB050468 | −4.4 | 0.000 |
| F5 | AA910306 | −4.4 | 0.004 |
| LOC90268 | AA723152 | −4.4 | 0.000 |
| bK215D11.1, bK215D11.2, bK215D11.3 | AL034417 | −4.4 | 0.000 |
| ABCC4 | AI248055 | −4.4 | 0.000 |
| FACL3 | D89053 | −4.4 | 0.000 |
| KIAA1921 | BE465475 | −4.3 | 0.000 |
| PDEF | NM_012391 | −4.3 | 0.000 |
| ELL2 | AI745624 | −4.3 | 0.000 |
| WRCH-1 | AB051826 | −4.2 | 0.000 |
| C1orf21 | AL563236 | −4.2 | 0.000 |
| RFXDC1 | NM_173560.1 | −4.2 | 0.000 |
| KCNMA1 | U11058 | −4.2 | 0.000 |
| KLF5 | AF132818 | −4.2 | 0.000 |
| ZNF145 | NM_006006 | −4.2 | 0.000 |
| ELL2 | AI924426 | −4.2 | 0.000 |
| CXCR4 | AJ224869 | −4.2 | 0.000 |
| MGC13102 | AW090182 | −4.2 | 0.000 |
| LIN-7B | NM_022165 | −4.1 | 0.000 |
| DKFZP434E2135 | NM_030804 | −4.1 | 0.000 |
| ACY1L2 | AI654133 | −4.1 | 0.001 |
| PGC | NM_002630 | −4.1 | 0.000 |
| HOMER-2B | Y19026 | −4.1 | 0.000 |
| SLC2A3 | BE550486 | −4.1 | 0.000 |
| UCHL1 | NM_004181 | −4.1 | 0.001 |
| OACT2 | W63676 | −4.1 | 0.000 |
| FACL3 | NM_004457 | −4.1 | 0.000 |
| MAF | AA442149 | −4.1 | 0.006 |
| SEC14L2 | R49343 | −4.1 | 0.002 |
| 229814_at | BG149337 | −4.0 | 0.000 |
| ABHD2 | AI832249 | −4.0 | 0.002 |
| FAM13C1 | BC036453.1 | −4.0 | 0.000 |
| TBC1D1 | BE882538 | −4.0 | 0.000 |
| NAT3 | AF193836 | −4.0 | 0.000 |
| FLJ10350 | NM_018067 | −4.0 | 0.000 |
| CEP2 | W81196 | −4.0 | 0.003 |
| AZGP1 | D90427 | −4.0 | 0.000 |

TABLE 4

Transcripts inhibited at least 2-fold (p ≤ 0.01) by polyamide 1 that are also induced at least 4-fold (p ≤ 0.01) by dihydrotestosterone.

| Name | Accession # | Fold Change | P-value |
|---|---|---|---|
| ANKH | NM_019847 | −7.3 | 0.000 |
| FLJ11264 | NM_018371 | −6.6 | 0.000 |
| KCNMA1 | U11058 | −6.3 | 0.000 |
| FER1L3 | NM_013451 | −6.2 | 0.000 |
| AKAP12 | AB003476 | −5.7 | 0.000 |
| ORM2 | NM_000608 | −5.6 | 0.000 |
| TMCC3 | N51717 | −5.4 | 0.000 |
| FER1L3 | AF207990 | −5.2 | 0.000 |
| KCNMA1 | AI129381 | −5.1 | 0.000 |
| PRKCA | AI471375 | −5.1 | 0.000 |
| LOC144481 | AK054607 | −5.1 | 0.000 |
| PTPRN2 | NM_002847 | −4.8 | 0.000 |
| AFF3 | AW085505 | −4.8 | 0.000 |
| ORM1 | NM_000607 | −4.5 | 0.000 |
| SPOCK | AF231124 | −4.4 | 0.000 |
| BMPR1B | D89675 | −4.3 | 0.001 |
| TRG@ | M16768 | −4.2 | 0.000 |
| C1orf21 | NM_030806 | −4.2 | 0.000 |
| TRGC2 | M13231 | −4.1 | 0.000 |
| LOC221981 | R33964 | −3.9 | 0.000 |
| TRG@ | M27331 | −3.8 | 0.000 |
| RFXDC1 | NM_173560.1 | −3.8 | 0.000 |
| CRIP2 | U36190 | −3.8 | 0.000 |
| ORM1 | NM_000607 | −3.7 | 0.000 |
| ANK1 | NM_020479 | −3.5 | 0.010 |
| C1orf21 | AI159874 | −3.5 | 0.000 |
| KLK3 | NM_001648 | −3.5 | 0.000 |
| KLK3 | U17040 | −3.3 | 0.000 |
| MGC18216 | AL044092 | −3.3 | 0.000 |
| FLJ23153 | AA650281 | −3.3 | 0.000 |
| 230710_at | W05495 | −3.1 | 0.000 |
| TRG@ | M30894 | −3.1 | 0.000 |
| C1orf21 | AL563236 | −3.1 | 0.000 |
| KIAA0869 | AK001727 | −3.1 | 0.000 |
| ABCC4 | AI248055 | −3.0 | 0.000 |
| DKFZP434B044 | AL136861 | −2.9 | 0.000 |
| KIAA1145 | BG177562 | −2.9 | 0.000 |
| 242391_at | AW052176 | −2.8 | 0.000 |
| STAT1 | NM_003877 | −2.8 | 0.000 |
| ELL2 | AI745624 | −2.7 | 0.000 |
| FAM13C1 | BC036453.1 | −2.7 | 0.000 |
| KIAA1921 | BE465475 | −2.7 | 0.000 |
| NDRG1 | NM_006096 | −2.7 | 0.000 |
| SLC26A3 | NM_000111 | −2.6 | 0.000 |
| TRPM8 | AI272941 | −2.6 | 0.000 |
| STAT2 | AB004903 | −2.5 | 0.000 |
| MAK | NM_005906 | −2.5 | 0.000 |
| MGC4827 | NM_024114 | −2.5 | 0.000 |
| PHLDB2 | AK025444 | −2.5 | 0.000 |
| 1556185_a_at | BC035072.1 | −2.4 | 0.000 |
| KLK2 | AF188747 | −2.4 | 0.000 |
| RAB3B | AU156710 | −2.4 | 0.000 |
| CNKSR2 | AI670947 | −2.4 | 0.002 |
| TMPRSS2 | AI660243 | −2.3 | 0.000 |
| 230782_at | AV699883 | −2.3 | 0.000 |
| TMPRSS2 | AF270487 | −2.3 | 0.000 |
| KLK2 | BC005196 | −2.3 | 0.000 |
| LIN-7B | NM_022165 | −2.3 | 0.000 |
| SLC15A2 | BF223679 | −2.3 | 0.000 |
| MPHOSPH9 | X98258 | −2.2 | 0.000 |

TABLE 4-continued

Transcripts inhibited at least 2-fold (p ≤ 0.01) by polyamide 1 that are also induced at least 4-fold (p ≤ 0.01) by dihydrotestosterone.

| Name | Accession # | Fold Change | P-value |
|---|---|---|---|
| KLK2 | AA595465 | −2.2 | 0.000 |
| LIFR | AI680541 | −2.2 | 0.000 |
| TMPRSS2 | NM_005656 | −2.2 | 0.000 |
| TBX15 | AI039005 | −2.1 | 0.000 |
| DKFZP434B0335 | BF513674 | −2.1 | 0.000 |
| SLC41A1 | AW439816 | −2.1 | 0.000 |
| FAM105A | AF052146 | −2.1 | 0.001 |
| AZGP1 | D90427 | −2.1 | 0.000 |
| MAF | NM_005360 | −2.1 | 0.000 |
| STK17B | N51102 | −2.0 | 0.000 |

Figure 13A:
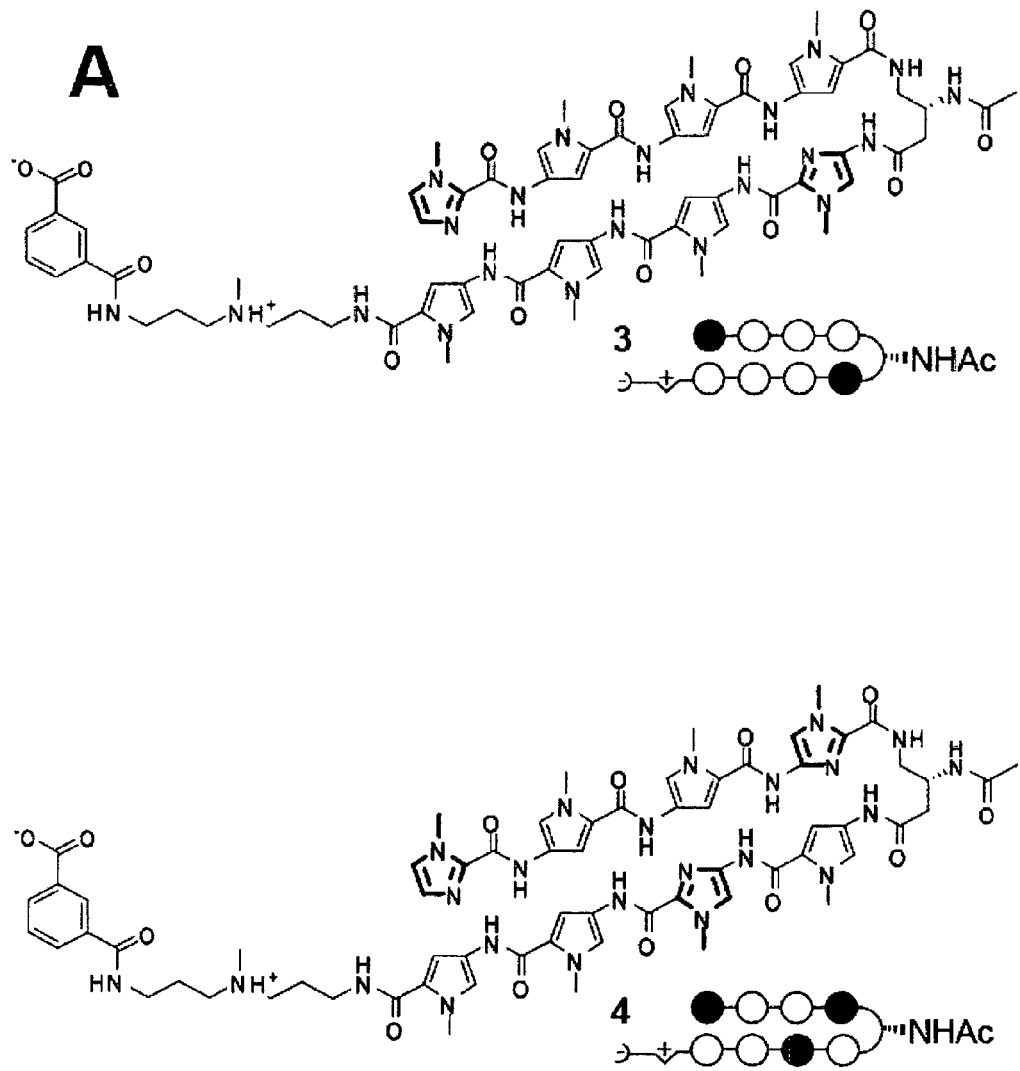
FIG. 13. Representative isotherms depicting the effects of polyamide 3 that targets the ARE (square), and control polyamide 4 (circle), and bicalutamide (triangle) on PSA mRNA expression. (A) Structures of 3 and 4. (B) Inhibition of DHT-induced PSA mRNA expression in LNCaP cells by 3 and Bic. (C) Inhibition of DHT-induced PSA mRNA expression in LNAR cells by 3. (D) Inhibition of basal PSA mRNA expression (no DHT) by 3 and induction by bicalutamide.
Figure 13D:
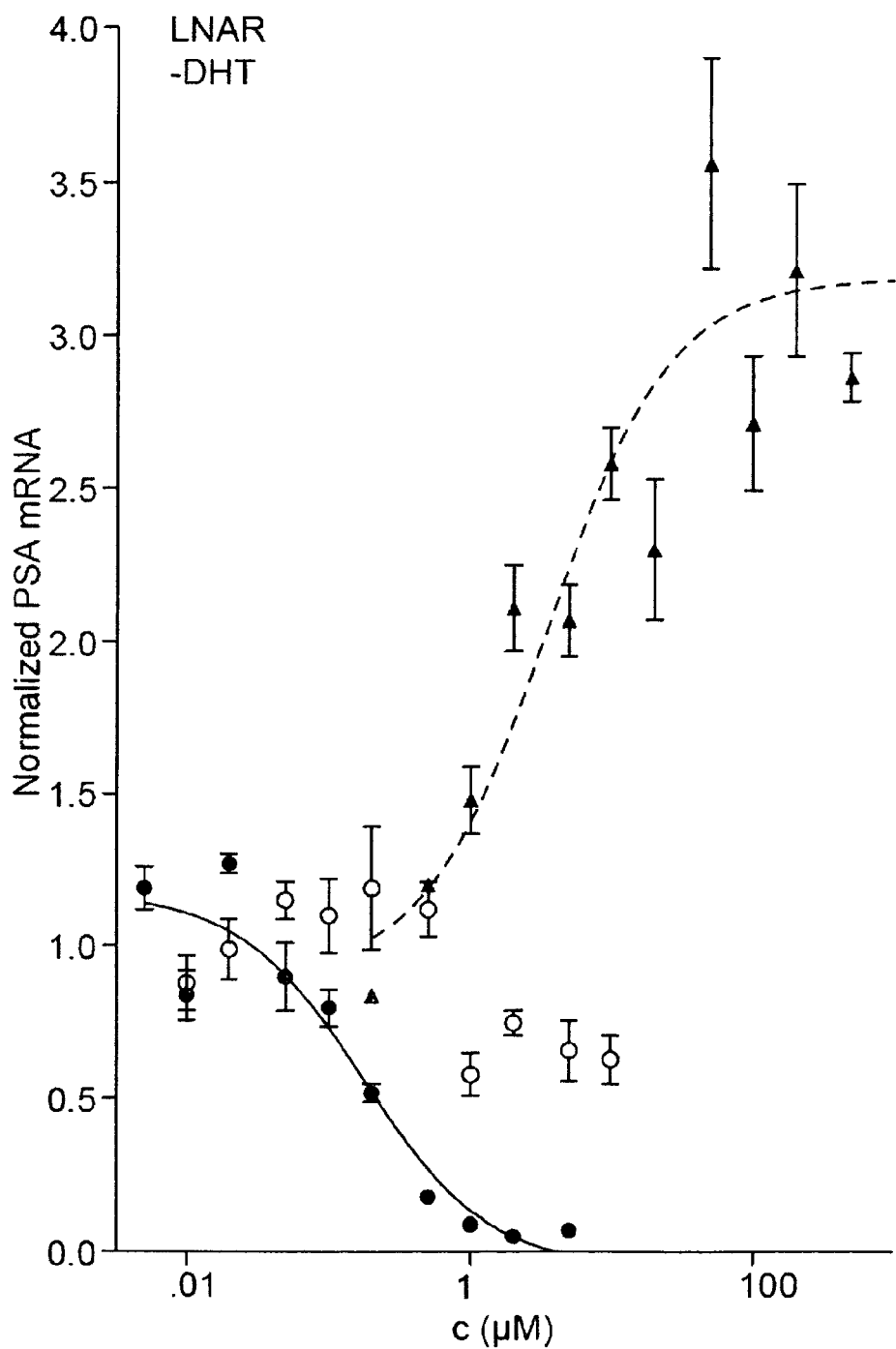
Figure 14:
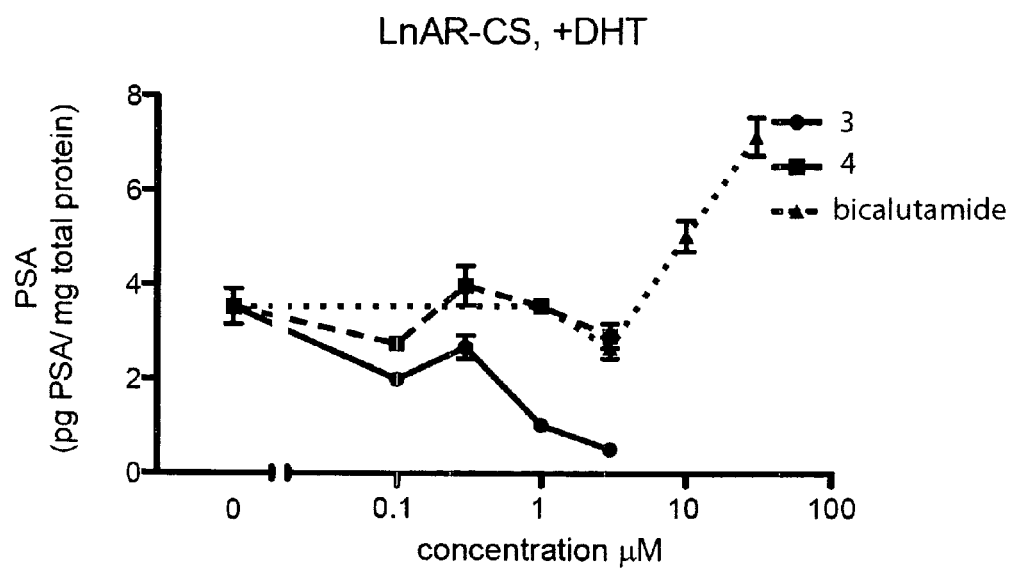
FIG. 14. Effects of polyamides on PSA secretion in hormone refractory LNAR-CS cells. Polyamide 3 inhibits secretion of PSA in hormone refractory prostate cancer cells. Polyamide 4 (control) has minimal effect. Bicalutamide fails to inhibit PSA secretion, further induces PSA expression upon DHT-stimulation.

PSA mRNA expression (no DHT) is inhibited by polyamide 3 and inducted by bicalutamide (FIG. 13 D). Table 5 shows the IC50 values for inhibition of PSA mRNA expression by polyamides 3 and 4 and bicalutamide (Bicalutamide induces PSA mRNA in LNAR cells). The effects on secreted PSA protein mirror the effects on mRNA; polyamide 3 inhibits secretion of PSA in hormone refractory LNAR prostate cancer cells. Polyamide 4 (control) has minimal effect. Bicalutamide fails to inhibit PSA secretion, and further induces PSA expression upon DHT-stimulation (FIG. 14).

1.5 Discussion

Because numerous signaling pathways converge on a smaller number of transcription factors to exert their effects on gene expression, it has been proposed that transcription

TABLE 5

IC50 values for inhibition of PSA mRNA expression

| Compound | | LNCaP +DHT | LNAR +DHT | LNAR −DHT |
|---|---|---|---|---|
| 3 | Match | 500 ± 100 nM | 300 ± 30 nM | 120 ± 30 nM |
| 4 | Mismatch | >10 μM | >10 μM | >10 μM |
| Bic | | 900 nM | >1 mM | (3.5 μM) | factors could be among the most appropriate drug targets in oncology (28, 29). This possibility has underscored the challenge to design small molecules capable of selectively disrupting protein-protein interactions between coactivators as well as protein-DNA interactions between transcription factors and their target sites in gene regulatory sequences.

Prostate cancer cells depend on stimulation by circulating androgens that exert their effects through the AR signaling axis. Hormone therapies that block AR activity by starving it of androgens or inhibiting ligand binding are initially successful but ultimately fail to control disease (12). This failure can occur through up-regulation of AR, mutations in the ligand-binding pocket, and ligand-independent activation from upstream signaling proteins (13, 30, 31). It is thought, however, that intact activity of AR signaling is necessary for disease progression (9). Inhibition of the AR-DNA interaction by a sequence-specific DNA-binding molecule could be expected to interfere with AR signaling under both hormone-sensitive and hormone-refractory conditions.

Figure 12A:
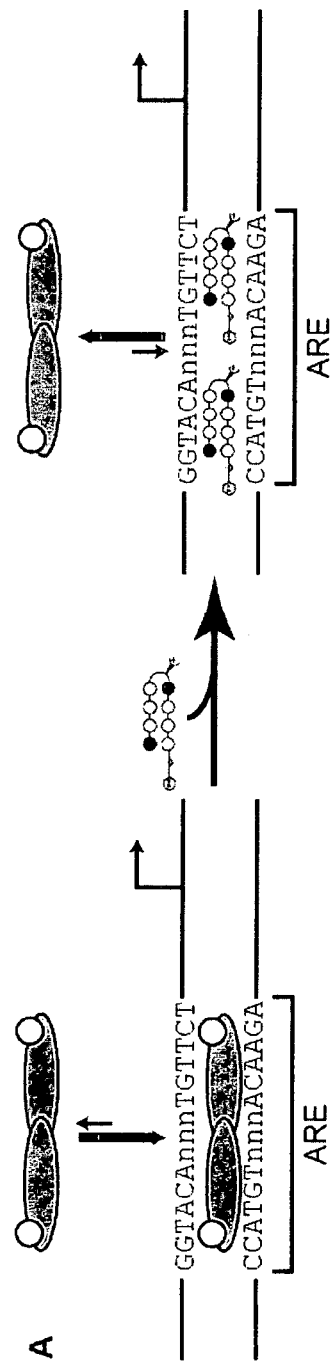
FIG. 12. Disrupting the AR/ARE interface in hormone refractory prostate cancer cells, LNAR-CS. LNAR-CS cells over-express AR, and form hormone refractory tumors when xenografted in mice. AR regulated genes in LNAR-CS cells are not inhibited by anti-androgens such as bicalutamide. (A) Upregulation of androgen receptor defeats many synthetic anti-androgens targeted to the ligand-binding pocket. Addition of a DNA-binding polyamide targeting the ARE consensus sequence (SEQ ID NOS:1, 2) disrupts the AR/ARE interface and offers an alternative anti-androgen strategy that maintains efficacy in hormone refractory cells such as LNAR-CS. (B) Inhibition of DHT-induced PSA in LNAR-CS cells by 1 and 2 and basal PSA expression (no DHT) by 1 and 2 (C). Bicalutamide induces expression of PSA in LNAR-CS cells.

Polyamide 1 binds to a half-site of the ARE of the PSA promoter with a subnanomolar $K_d$ and inhibits expression of ≈35% of transcripts that are observed to be induced at least 4-fold by DHT in LNCaP cells. Down-regulation of PSA by this polyamide is comparable to that produced by the synthetic antiandrogen bicalutamide at the same concentration. Control polyamide 2, which targets a different DNA sequence, 5'-WGWCGW-3', had significantly less effect on Polyamide 1 was tested for its ability to inhibit AR binding and expression of AR regulated genes in a cell line model of hormone refractory prostate cancer. The cell line LNAR was used, which has been engineered to over-express AR (14). LNAR cells over-express AR and form hormone refractory tumors when xenografted in mice (14). AR regulated genes in LNAR-CS cells are not inhibited by anti-androgens such as bicalutamide (14). Upregulation of androgen receptor defeats many synthetic anti-androgens targeted to the ligand-binding pocket. Polyamide 1 disrupts the AR/ARE interface and maintains efficacy in hormone refractory cells such as LNAR. Inhibition of DHT-induced PSA in LNAR cells by 1 and 2 and basal PSA expression (no DHT) by 1 and 2 is shown (FIGS. 12 B and C). Bicalutamide induces expression of PSA in LNAR-CS cells (FIG. 12 C).

Polyamide 3, an analog of polyamide 1 that differs only at the "turn," also inhibits PSA mRNA expression in DHT-induced LNCaP and LNAR cells, as well as basal expression of PSA mRNA in LNAR cells. Polyamide 4 is a corresponding analog of polyamide 2 and has little effect on PSA expression under these conditions. The structures of 3 and 4 are depicted in FIG. 13 A. Representative isotherms are shown depicting the effects of polyamide 3 that targets the ARE (square), and control polyamide 4 (circle), and bicalutamide (triangle) on PSA mRNA expression in LNCaP cells (FIG. 13 B) and LNAR cells (FIG. 13 C). Bicalutamide does not inhibit PSA mRNA expression in LNAR cells (FIG. 13 C). Basal androgen-induced gene expression. Expression of PSA (KLK3), KLK2, TMPRSS2, and FKBP5, which are direct AR targets, were all affected by 1. TMPRSS2 encodes a transmembrane protease and can undergo a chromosomal deletion in which a member of the ETS transcription factor family is placed under control of the strongly androgen-responsive TMPRSS2 5' regulatory region (27, 32).

At the same concentration, polyamide 1 and bicalutamide affected a comparable number of transcripts, whereas polyamide 2 affected significantly fewer. When using bicalutamide as a point of reference, the overall effects on genomic transcription by 1 and 2 are relatively modest. Although it is difficult to compare across experimental conditions, the observation that a limited number of genes are affected by each polyamide in this study is consistent with previous reports (21). A comparison of the expression data for cells treated with polyamide 1 or 2 reveal that some transcripts are similarly affected, but many are differentially affected by the two polyamides (FIG. 10A), which is consistent with previous comparisons of gene expression profiles of cells treated with polyamides of different target sequence (21, 33).

Polyamide 1, as well as related polyamide 3 which targets the same DNA sequence, retains its antagonism of AR in the hormone-refractory model cell line LNAR that over-expresses AR. In this cell line bicalutamide loses all activity as an antagonist and displays weak agonist activity.

The AR, glucocorticoid receptor, and estrogen receptor share a highly conserved DNA-binding domain (34-36). This domain, related to the classical Cys-2-His-2 zinc finger motifs (37), contains two modules of zinc coordinated by four cysteines. Previously, a polyamide targeted to the estrogen receptor response element inhibited binding of estrogen receptors α and β in gel-shift assays (38). In separate in vitro experiments, minor groove-binding polyamides have been shown to inhibit the major groove binding of Zif268 and other zinc finger proteins to their target sites on DNA by an allosteric mechanism (39). In light of this observation, it is not unexpected that a polyamide targeted to the ARE would inhibit AR binding.

The ARE is sufficiently degenerate such that a single polyamide is not likely to affect all AR-regulated genes simultaneously. The identities of the particular AR target genes involved in prostate cancer progression are not fully known. In the absence of this knowledge, it was our goal to target the ARE broadly to maximize the number of AR target genes affected by using a single polyamide. However, the programmability of polyamides might allow selective inhibition of a predetermined subset of AR target genes by one or a small mixture of tailored polyamide molecules. The utility of disrupting the AR-ARE interface with DNA-binding small molecules will depend on continued experimentation in small animal models of hormone refractory prostate cancer and AR-regulated gene expression (40-42).

Example 2

2.1 Abstract

Glucocorticoid receptor (GR) regulates expression of genes involved in many biological processes including inflammation. A DNA-binding polyamide that targets the consensus glucocorticoid response element binds the glucocorticoid-induced leucine zipper glucocorticoid response element (GRE), inhibits dexamethasone-induced expression of GILZ in cultured lung cancer cells, and reduces GR occupancy at the GILZ enhancer. Direct inhibition of the GR-DNA interface by sequence-specific DNA binding small molecules could offer an alternative approach to modulating GR activity.

Abbreviations: GR, glucocorticoid receptor; GRE, glucocorticoid response element; GILZ, glucocorticoid induced leucine zipper.

2.2 Introduction

Because polyamide 1, which is expected to bind to most AREs, inhibited the expression of DHT-induced AR regulated genes in LNCaP cells, it was hypothesized that the polyamide 1 might also inhibit the expression of dexamethasone-induced GR regulated genes, since the sequence preferences of AR and GR are very similar as are the amino acid sequences of their respective DNA binding domains. The glucocorticoid receptor (GR) is also a member of the ligand-activated nuclear receptor family of transcription factors (46, 47). Like AR, ligand binding to GR initiates release from the cytoplasm, dimerization, binding to the glucocorticoid response elements (GRE) of target genes, and gene activation through interaction with co-activators and the general transcription machinery. The GREs, consensus 5'-GGTACAnnnTGTTCT-3' (SEQ ID NO:1), can occur near transcription start sites or in enhancers that are several thousand base pairs up or down stream. GR interacts with co-activator proteins to up- or down-regulate specific target genes in a cell-type specific manner (46, 47). Target genes are involved in a large array of biological processes including the immune response. In addition to direct effects on gene transcription through interaction with GREs, GR mediates non-genotropic effects through interaction with cytoplasmic signaling proteins.

DNA-binding polyamides represent one approach to inhibiting protein-DNA interactions. Polyamides containing N-methylimidazole (Im) and N-methylpyrrole (Py) comprise a class of programmable DNA-binding ligands capable of binding to a broad repertoire of DNA sequences with affinities and specificities comparable to those of natural DNA-binding proteins (17, 18). Sequence specificity is programmed by side-by-side pairings of the heterocyclic amino acids in the minor groove of DNA: Im/Py distinguishes G•C from C•G; Py/Py binds both A•T and T•A (19, 20). Previously, a hairpin polyamide targeted to the hypoxia response element (HRE) inhibited hypoxia-induced expression of several HIF-1-regulated genes, including VEGF, in cultured cells (21, 22).

A polyamide that targets the sequence 5'-WGWWCW-3', might be expected antagonize GR-mediated gene expression through interaction with GREs at the regulatory sequences of GR-target genes (FIG. 15A). We show that such a polyamide binds two GREs found in the GILZ enhancer, inhibits expression of GILZ, and reduces GR occupancy at the GILZ enhancer. A control polyamide targeted to a different sequence had less effect. The modulation of GR activity at the level of DNA binding could have implications for selectively antagonizing genotropic GR activity while leaving non-genotropic activity unaffected. This separation of activity of GR might have useful applications in modulating the effects from glucocorticoid treatment, and is likely not possible using drugs or other molecules currently available.

2.2 Materials and Methods 2.2.1 Synthesis of Polyamides

Polyamides 1 and 2 were synthesized by solid-phase methods on Kaiser oxime resin (Nova Biochem, Darmstadt, Germany) according to established protocols (43).

2.2.2 Determination of DNA-Binding Affinity and Sequence Specificity

Quantitative DNase I footprint titration experiments were used to measure the binding affinities of 1 and 2 on a 5'-$^{32}$P- labeled fragment of plasmid pKAM5 that contains the GILZ enhancer GREs. Detailed experimental protocols are reported elsewhere (44).

2.2.3 Electrophoretic Mobility Shift Assay

Polyamides 1 and 2 were incubated with a 5'-$^{32}$P labeled duplex containing the GILZ GREs, and GR protein was added. Complexes were run on a polyacrylamide gel and visualized on a phosphorimager.

2.2.4 Measurement of Androgen-Induced PSA mRNA and Protein

A549 cells (ATCC) were plated in 24-well plates. After 48 h, the medium was replaced and polyamides added at the designated concentrations. Cells were grown for an additional 48 h and then treated with 100 nM dexamethasone. Isolation of RNA and cDNA synthesis was performed as described (21). Quantitative real-time RT-PCR was performed with SYBR Green PCR Master Mix (Applied Biosystems, Foster City, Calif.) on an ABI 7300 instrument. PSA mRNA was measured relative to β-glucuronidase as an endogenous control. Primer sequences are available upon request.\

2.3.5 Chromatin Immunoprecipitation

A549 cells were plated in 15-cm diameter plates. Media, polyamide treatment, time course, and DHT stimulation were the same as described above. After dexamethasone treatment, cells were treated with 1% formaldehyde for 10 min. Chromatin was isolated and sheared. Antibodies to GR (graciously gifted by Keith Yamamoto) were used to immunoprecipitate GR-bound DNA fragments. Crosslinks were reversed, and PCRs using primers targeted to the regions of interest were used to assess enrichment of bound fragments as compared with mock-precipitated (no antibody) controls. PCRs were monitored with SYBR Green PCR Master Mix (Applied Biosystems) on an ABI 7300 instrument. Primer sequences and a more detailed experimental protocol are available upon request.

2.4 Results 2.4.1 Binding Affinities of Polyamides to the GREs of the GILZ Enhancer The GILZ enhancer contains two GREs separated by 22 base pairs (46). GRE 1 is 5'-GCCTGCACTTTGTTCT=3' (SEQ ID NO:5) and GRE 2 is GCAAACACCGTGTTCA-3' (SEQ ID NO:7). The DNA binding of polyamides 1 and 2 on these sequences was measured by quantitative DNase I footprint. Polyamide 1 has a $K_a=1.9\pm0.8\times10^{10}$ for GRE1 and $K_a=8.8\pm1.8\times10^9$ for GRE2 (FIG. 16 A-C). Polyamide 1 has a $K_a=1.9\pm0.8\times10^{10}$ for GRE1 and $K_a=8.8\pm1.8\times10^9$ for GRE2 (FIG. 16 A-C).

2.4.3 Inhibition of Dexamethasone-Inducted GILZ Expression

Induction of GILZ mRNA by dexamethasone in the presence of polyamides 1 and 2 in A549 cells was measured by quantitative real-time RT-PCR. Polyamide 1 inhibits the expression of DHT-induced PSA in a dose-dependent manner up to ≈60% at 10 μM, as measured in this assay (FIG. 17A). Polyamide 2 has a more modest effect. GR occupancy at the GILZ enhancer was assessed by chromatin immunoprecipitation (FIG. 17B). Chromatin immunoprecipitation assays with anti-GR antibody treatment indicate decreased occupancy of GR at the GILZ enhancer in the presence of 10 μM 1.

Example 3

3.1 Overview

It is possible to inhibit the protein-DNA interactions AR-ARE and GR-GRE using polyamides targeted to sequences found in the consensus ARE and GRE. A cell permeable polyamide targeted to these sequences that can access chromatin in cells, bind target sequences, and prevent or displace the binding of the AR or GR, was able to affect the expression of genes regulated by AR or GR.

Because the DNA binding domains of androgen receptor, glucocorticoid receptor, and estrogen receptor are similar in structure, it is here hypothesized that a polyamide targeted to bind at estrogen response elements, EREs, could be expected to antagonize estrogen receptor (ER) activity in cells. Two forms of ER, ER-alpha and ER-beta, exist. These receptors are also members of the ligand-activated nuclear receptor family of transcription factors (48). Like AR and GR, ligand binding to ER initiates release from the cytoplasm, dimerization, binding to the estrogen response elements (ERE) of target genes, and gene activation through interaction with co-activators and the general transcription machinery. The EREs, consensus 5'-AGGTCAnnnTGACCT-3' (SEQ ID NO:11), can occur near transcription start sites or in enhancers that are several thousand base pairs up or down stream. ER interacts with co-activator proteins to up- or down-regulate specific target genes.

Significantly, ER plays an important role in the growth of breast cancer. Close to two-thirds of breast cancers express either or both of the ER subtypes. Such cancers can be treated hormonally with selective estrogen receptor modulators, such as tamoxifen, or aromatase inhibitors, such as letrozole. However, breast cancers that are initially sensitive to these treatments can become resistant to these treatments over time. This resistance is thought to involve cellular adaptations to low levels of estrogen in which other signaling pathways, that activate the estrogen receptors at extremely low levels of ligand or even in its absence (49, 50). Inhibiting the ER-ERE interaction with a DNA binding molecules could be expected to retain activity under cellular conditions in which tamoxifen or aromatase inhibitors are inactive. Therefore, cell permeable molecules that can bind to EREs and inhibit the binding of or displace ER, for example a DNA binding polyamide targeted to bind the sequence 5'-WGGWCW-3', could be useful for the treatment of breast cancer. Because estrogen receptors play a role in regulating fertility, such molecules could also be useful for treatment of conditions characterized by infertility. Some breast cancers express progesterone receptor (PR), which is also a member of the steroid hormone receptor family of transcription factors.

FIG. 18 depicts an approach to inhibiting the ER-ERE protein-DNA interaction using DNA-binding Py-Im-polyamides. A polyamide targeted to bind the sequence 5'-WGG-WCW-3' is expected to bind many possible EREs and inhibit the binding of ER to these sequences in cells, antagonizing the activity of ER at genes regulated by these EREs.

REFERENCES FOR EXAMPLES 1-3

1. Tsai, M J & Omalley, B W. (1994) *Annu Rev Biochem* 63, 451-486.
2. Tyagi, R K, Lavrovsky, Y, Ahn, S C, Song, C S, Chatterjee, B & Roy, A K. (2000) *Mol Endocrinol* 14, 1162-1174.
3. Roche, P J, Hoare, S A & Parker, M G. (1992) *Mol Endocrinol* 6, 2229-2235.
4. Cleutjens, K B, van der Korput, H A, van Eekelen, C C, van Rooij, H C, Faber, P W & Trapman, J. (1997) *Mol Endocrinol* 11, 148-161.

5. Cleutjens, K B, van Eekelen, C C, van der Korput, H A, Brinkmann, A O & Trapman, J. (1996) *J Biol Chem* 271, 6379-6388.
6. Huang, W B, Shostak, Y, Tarr, P, Sawyers, C & Carey, M. (1999) *J Biol Chem* 274, 25756-25768.
7. Shang, Y F, Myers, M & Brown, M. (2002) *Mol Cell* 9, 601-610.
8. Wang, Q B, Carroll, J S & Brown, M. (2005) *Mol Cell* 19, 631-642.
9. Scher, H I & Sawyers, C L. (2005) *J Clin Oncol* 23, 8253-8261.
10. Huggins, C & Hodges, C V. (1941) *Cancer Res* 1, 293-297.
11. Huggins, C, Stevens, R E & Hodges, C V. (1941) *Arch Surg* (Chicago) 43, 209-223.
12. Oefelein, M G, Agarwal, P K & Resnick, M I. (2004) *J Urol* 171, 1525-1528.
13. Xin, L, Teitell, M A, Lawson, D A, Kwon, A, Mellinghoff, I K & Witte, O N. (2006) *Proc Natl Acad Sci USA* 103, 7789-7794.
14. Chen, C D, Welsbie, D S, Tran, C, Baek, S H, Chen, R, Vessella, R, Rosenfeld, M G & Sawyers, C L. (2004) *Nat Med* 10, 33-39.
15. Han, G Z, Buchanan, G, Ittmann, M, Harris, J M, Yu, X Q, DeMayo, F J, Tilley, W & Greenberg, N M. (2005) *Proc Natl Acad Sci USA* 102, 1151-1156.
16. Bohl, C E, Gao, W Q, Miller, D D, Bell, C E & Dalton, J T. (2005) *Proc Natl Acad Sci USA* 102, 6201-6206.
17. Hsu, C F, Phillips, J W, Trauger, J W, Farkas, M E, Belitsky, J M, Heckel, A, Olenyuk, B Z, Puckett, J W, Wang, C C C & Dervan, P B. (2007) *Tetrahedron* 10.1016/j.tet.2007.03.041.
18. Dervan, P B & Edelson, B S. (2003) *Curr Opin Struct Biol* 13, 284-299.
19. Kielkopf, C L, Baird, E E, Dervan, P D & Rees, D C. (1998) *Nat Struct Biol* 5, 104-109.
20. White, S, Szewczyk, J W, Turner, J M, Baird, E E & Dervan, P B. (1998) *Nature* 391, 468-471.
21. Olenyuk, B Z, Zhang, G J, Klco, J M, Nickols, N G, Kaelin, W G & Dervan, P B. (2004) *Proc Natl Acad Sci USA* 101, 16768-16773.
22. Nickols, N G, Jacobs, C S, Farkas, M E & Dervan, P B. (2007) *Nucleic Acids Res* 35, 363-370.
23. DePrimo, S E, Diehn, M, Nelson, J B, Reiter, R E, Matese, J, Fero, M, Tibshirani, R, Brown, P O & Brooks, J D. (2002) *Genome Biol* 3, research0032.1-research0032.12.
24. Magee, J A, Chang, L W, Stormo, G D & Milbrandt, J. (2006) *Endocrinology* 147, 590-598.
25. Nelson, P S, Clegg, N, Arnold, H, Ferguson, C, Bonham, M, White, J, Hood, L & Lin, B Y. (2002) *Proc Natl Acad Sci USA* 99, 11890-11895.
26. Mitchell, S H, Murtha, P E, Zhang, S B, Zhu, W & Young, C Y F. (2000) *Mol Cell Endocrinol* 168, 89-99.
27. Tomlins, S A, Rhodes, D R, Perner, S, Dhanasekaran, S M, Mehra, R, Sun, X W, Varambally, S, Cao, X H, Tchinda, J & Kuefer, R, et al. (2005) *Science* 310, 644-648.
28. Darnell, J E. (2002) *Nat Rev Cancer* 2, 740-749.
29. Pandolfi, P P. (2001) *Oncogene* 20, 3116-3127.
30. Mellinghoff, I K, Vivanco, I, Kwon, A, Tran, C, Wongvipat, J & Sawyers, C L. (2004) *Cancer Cell* 6, 517-527.
31. Chen, T S, Wang, L H & Farrar, W L. (2000) *Cancer Res* 60, 2132-2135.
32. Tomlins, S A, Mehra, R, Rhodes, D R, Smith, L R, Roulston, D, Helgesson, B E, Cao, X H, Wei, J T, Rubin, M A & Shah, R B, et al. (2006) *Cancer Res* 66, 3396-3400.
33. Burnett, R, Melander, C, Puckett, J W, Son, L S, Wells, R D, Dervan, P B & Gottesfeld, J M. (2006) *Proc Natl Acad Sci USA* 103, 11497-11502.
34. Shaffer, P L, Jivan, A, Dollins, D E, Claessens, F & Gewirth, D T. (2004) *Proc Natl Acad Sci USA* 101, 4758-4763.
35. Luisi, B F, Xu, W X, Otwinowski, Z, Freedman, L P, Yamamoto, K R & Sigler, P B. (1991) *Nature* 352, 497-505.
36. Schwabe, J W R, Chapman, L, Finch, J T & Rhodes, D. (1993) *Cell* 75, 567-578.
37. Pavletich, N P & Pabo, C O. (1991) *Science* 252, 809-817.
38. Gearhart, M D, Dickinson, L, Ehley, J, Melander, C, Dervan, P B, Wright, P E & Gottesfeld, J M. (2005) *Biochemistry* 44, 4196-4203.
39. Nguyen-Hackley, D H, Ramm, E, Taylor, C M, Joung, J K, Dervan, P B & Pabo, C O. (2004) *Biochemistry* 43, 3880-3890.
40. Klein, K A, Reiter, R E, Redula, J, Morad, H, Zhu, X L, Brothman, A R, Lamb, D J, Marcelli, M, Belldegrun, A & Witte, O N, et al. (1997) *Nat Med* 3, 402-408.
41. Ellwood-Yen, K, Wongvipat, J & Sawyers, C. (2006) *Cancer Res* 66, 10513-10516.
42. Iyer, M, Salazar, F B, Lewis, X, Zhang, L, Wu, L, Carey, M & Gambhir, S S. (2005) *Transgenic Res* 14, 47-55.
43. Belitsky, J M, Nguyen, D H, Wurtz, N R & Dervan, P B. (2002) *Bioorg Med Chem* 10, 2767-2774.
44. Trauger, J W & Dervan, P B. (2001) *Methods Enzymol* 340, 450-466.
45. Zhang, J Y, Zhang, S B, Murtha, P E, Zhu, W, Hou, S S M & Young, C Y F. (1997) *Nucleic Acids Res* 25, 3143-3150.
46. Wang J C, Derynck M K, Nonaka D F, Khodabakhsh D B, Haqq C, Yamamoto K R. (2004) *Proc Natl Acad Sci USA.* 44, 15603-15608.
47. So A Y, Chaivorapol C, Bolton E C, Li H, Yamamoto K R. (2007) *PLoS Genet* 6. e94.
48. Kumar V, Green S, Stack G, Berry M, Jin J R, Chambon P. (1987) *Cell.* 51, 941-51.
49. Sabnis G J, Jelovac D, Long B, Brodie A. (2005) *Cancer Res.* 65, 3903-10.
50. Moy B, Goss P E. (2006) *Clin Cancer Res.* 12, 4790-3.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Such modifications are intended to fall within the scope of the appended claims. All publications, including patent documents and scientific articles, referred to in this application and the bibliography and attachments are incorporated by reference in their entirety for all purposes to the same extent as if each individual publication were individually incorporated by reference. The article "a" as used herein means one or more unless indicated otherwise. All headings are for the convenience of the reader and should not be used to limit the meaning of the text that follows the heading, unless so specified.

What is claimed is:

1. A polyamide of structure 1 as follows:

wherein each X is CH; and wherein each $R_2$ is a $C_1$ alkyl; and wherein $R_3$ is linked to $R_4$ through a turn of structure 4 as follows:

wherein $R_7$ is H; and wherein $R_8$ is selected from structures 7-9 as follows:

and wherein $R_1$ has structure 46 as follows:

wherein $R_5$ is H; wherein y has structure 55 as follows:

and wherein p next to $R_3$ is 1 and p next to $R_5$ is 0.

2. The composition of claim 1, wherein $R_8$ has structure 7 as follows:

3. The composition of claim 1, wherein $R_8$ has structure 8 as follows:

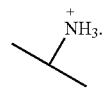

4. The composition of claim 1, wherein $R_8$ has structure 9 as follows:

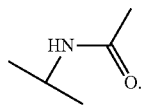

5. The composition of claim 1, wherein said composition further comprises a pharmaceutically acceptable carrier.

6. The composition of claim 2, wherein said composition further comprises a pharmaceutically acceptable carrier.

7. The composition of claim 3, wherein said composition further comprises a pharmaceutically acceptable carrier.

8. The composition of claim 4, wherein said composition further comprises a pharmaceutically acceptable carrier.

* * * * *

SEQUENCE LISTING

```
<160> NUMBER OF SEQ ID NOS: 17

<210> SEQ ID NO 1
<211> LENGTH: 15
<212> TYPE: DNA
<213> ORGANISM: human
<220> FEATURE:
<221> NAME/KEY: misc_feature
<222> LOCATION: 7, 8, 9
<223> OTHER INFORMATION: n = A,T,C or G

<400> SEQUENCE: 1
ggtacannnt gttct                                                      15

<210> SEQ ID NO 2
<211> LENGTH: 15
<212> TYPE: DNA
<213> ORGANISM: human
<220> FEATURE:
<221> NAME/KEY: misc_feature
<222> LOCATION: 7, 8, 9
<223> OTHER INFORMATION: n = A,T,C or G

<400> SEQUENCE: 2
agaacannnt gtacc                                                      15

<210> SEQ ID NO 3
<211> LENGTH: 48
<212> TYPE: DNA
<213> ORGANISM: human

<400> SEQUENCE: 3
gggtgatcta gtaattgcag aacagcaagt gctagctctc cctcccct                  48

<210> SEQ ID NO 4
<211> LENGTH: 48
<212> TYPE: DNA
<213> ORGANISM: human

<400> SEQUENCE: 4
aggggaggga gagctagcac ttgctgttct gcaattacta gatcaccc                  48

<210> SEQ ID NO 5
<211> LENGTH: 16
<212> TYPE: DNA
<213> ORGANISM: human

<400> SEQUENCE: 5
gcctgcactt tgttct                                                     16

<210> SEQ ID NO 6
<211> LENGTH: 16
<212> TYPE: DNA
<213> ORGANISM: human

<400> SEQUENCE: 6
agaacaaagt gcaggc                                                     16

<210> SEQ ID NO 7
<211> LENGTH: 16
<212> TYPE: DNA
<213> ORGANISM: human

<400> SEQUENCE: 7
gcaaacaccg tgttca                                                     16
```

```
<210> SEQ ID NO 8
<211> LENGTH: 16
<212> TYPE: DNA
<213> ORGANISM: human

<400> SEQUENCE: 8
tgaacacggt gtttgc                                                    16

<210> SEQ ID NO 9
<211> LENGTH: 57
<212> TYPE: DNA
<213> ORGANISM: human

<400> SEQUENCE: 9
tagcctgcac tttgttctgt ctactacaca tgtcttagtg caaacaccgt gttcaga       57

<210> SEQ ID NO 10
<211> LENGTH: 57
<212> TYPE: DNA
<213> ORGANISM: human

<400> SEQUENCE: 10
tctgaacacg gtgtttgcac taagacatgt gtagtagaca gaacaaagtg caggcta       57

<210> SEQ ID NO 11
<211> LENGTH: 15
<212> TYPE: DNA
<213> ORGANISM: human
<220> FEATURE:
<221> NAME/KEY: misc_feature
<222> LOCATION: 7, 8, 9
<223> OTHER INFORMATION: n = A,T,C or G

<400> SEQUENCE: 11
aggtcannnt gacct                                                     15

<210> SEQ ID NO 12
<211> LENGTH: 15
<212> TYPE: DNA
<213> ORGANISM: human
<220> FEATURE:
<221> NAME/KEY: misc_feature
<222> LOCATION: 7, 8, 9
<223> OTHER INFORMATION: n = A,T,C or G

<400> SEQUENCE: 12
ggwacannnt gttct                                                     15

<210> SEQ ID NO 13
<211> LENGTH: 15
<212> TYPE: DNA
<213> ORGANISM: human
<220> FEATURE:
<221> NAME/KEY: misc_feature
<222> LOCATION: 1, 7, 8, 9, 15
<223> OTHER INFORMATION: n = A,T,C or G

<400> SEQUENCE: 13
ngwacwnnnt gtycn                                                     15

<210> SEQ ID NO 14
<211> LENGTH: 31
<212> TYPE: DNA
<213> ORGANISM: human
```

```
<400> SEQUENCE: 14
gcattgcaga acagcaagtg ctagctctcc c                            31

<210> SEQ ID NO 15
<211> LENGTH: 15
<212> TYPE: DNA
<213> ORGANISM: human

<400> SEQUENCE: 15
agaacagcaa gtgct                                              15

<210> SEQ ID NO 16
<211> LENGTH: 15
<212> TYPE: DNA
<213> ORGANISM: human

<400> SEQUENCE: 16
agcacatcga gttca                                              15

<210> SEQ ID NO 17
<211> LENGTH: 15
<212> TYPE: DNA
<213> ORGANISM: human

<400> SEQUENCE: 17
agaacagggt gttct                                              15
```